US012788630B1

(12) United States Patent
Sekhavat et al.

(10) Patent No.: US 12,788,630 B1
(45) Date of Patent: Nov. 10, 2026

(54) DEVICE, METHODS AND SYSTEM FOR PERFORMING INCISIONS OR EXCISIONS IN THE TRABECULAR MESHWORK

(71) Applicant: Hexiris Inc., Dieppe (CA)

(72) Inventors: Houfar Sekhavat, Dieppe (CA); Kenneth Dale Johannaber, Reno, NV (US)

(73) Assignee: Hexiris Inc., Dieppe (CA)

( * ) Notice: Subject to any disclaimer, the term of this patent is extended or adjusted under 35 U.S.C. 154(b) by 0 days.

(21) Appl. No.: 19/572,645

(22) Filed: Mar. 19, 2026

Related U.S. Application Data

(63) Continuation of application No. PCT/CA2026/050420, filed on Mar. 18, 2026.

(30) Foreign Application Priority Data

Jun. 27, 2025 (GB) ..................................... 2510313

(51) Int. Cl.
*A61F 9/007* (2006.01)
*A61F 9/013* (2006.01)

(52) U.S. Cl.
CPC ...... *A61F 9/00736* (2013.01); *A61F 9/00781* (2013.01); *A61F 9/0133* (2013.01)

(58) Field of Classification Search
CPC .............. A61F 9/00709; A61F 9/00736; A61F 9/00781; A61F 9/0133; A61F 9/00754; A61F 9/00763
See application file for complete search history.

(56) References Cited

U.S. PATENT DOCUMENTS 5,713,915 A * 2/1998 Van Heugten ........ A61F 9/0133 606/166
6,139,559 A * 10/2000 Nordan ................. A61F 9/0133 606/166
12,575,849 B2 * 3/2026 Messerly ....... A61B 17/320068
2002/0026205 A1 * 2/2002 Matsutani ............ A61F 9/0133 606/167
2007/0060926 A1 * 3/2007 Escaf .................. A61F 9/00745 606/107
2021/0113376 A1 * 4/2021 Grueebler ............... B26B 29/02
2021/0315738 A1 * 10/2021 Phillips ................. A61F 9/0017
2021/0330498 A1 * 10/2021 Gooi ................ A61B 17/00234
2021/0330502 A1 * 10/2021 Tazawa ................. A61F 9/0133
2022/0265471 A1 * 8/2022 Kuo .................... A61F 9/00736
2022/0346943 A1 * 11/2022 Kahook ................ A61F 2/1648
2025/0073069 A1 * 3/2025 Ichikawa ............ A61F 9/00736

* cited by examiner

*Primary Examiner* — Phong Son H Dang
(74) *Attorney, Agent, or Firm* — MARSHALL, GERSTEIN & BORUN LLP

(57) ABSTRACT

An ophthalmic surgical device for trabecular meshwork incision or excision includes a blade with adjustable penetration depth, a tissue reference surface for contacting the sclera, and a depth control system. The depth control system has a depth-limiting mechanism with selectable depth presets corresponding to predetermined blade extension distances. A bidirectional cutting geometry of the blade enables incision or excision in opposing circumferential directions while the device remains in the eye. A method includes selecting a depth preset, positioning the tissue reference surface against the eye, extending the blade to the selected depth, and incising trabecular meshwork in opposing directions.

16 Claims, 30 Drawing Sheets

FIG. 23A
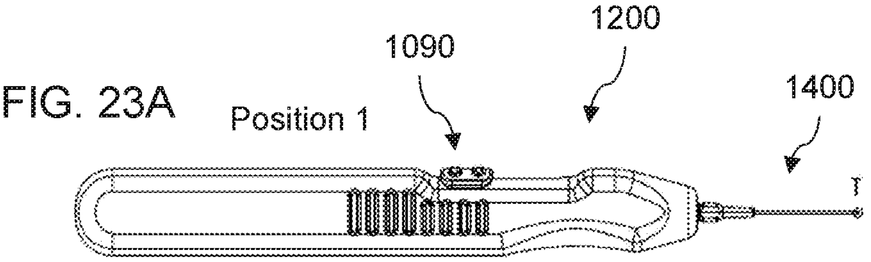
FIG. 23B
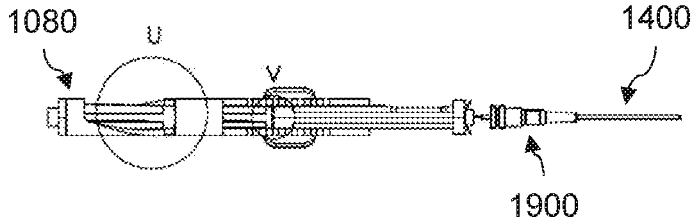
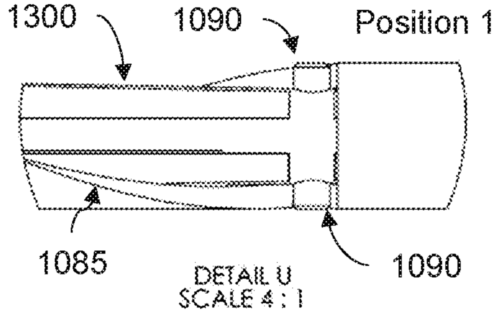
FIG. 23C
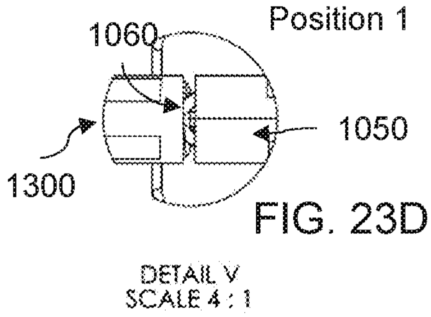
FIG. 23D
FIG. 23E
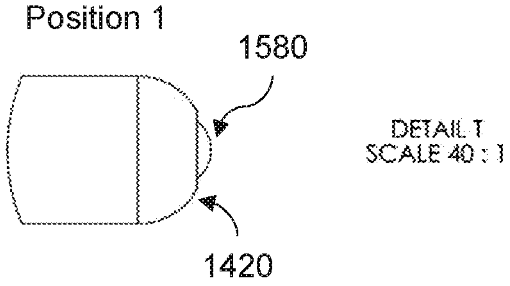

FIG. 24A
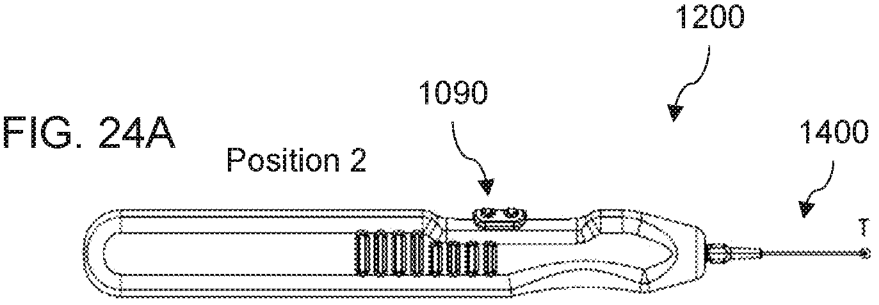
FIG. 24B
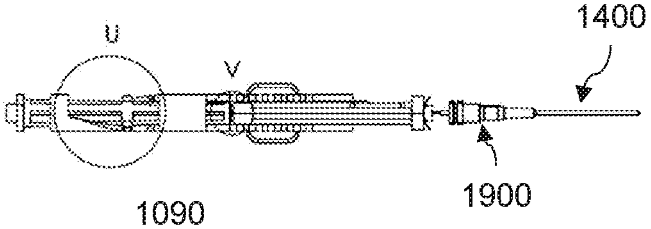
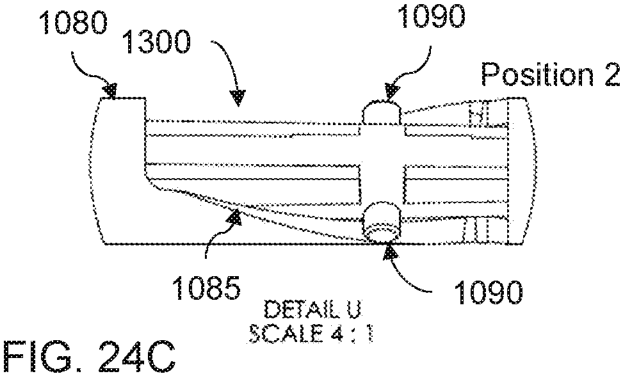
FIG. 24C
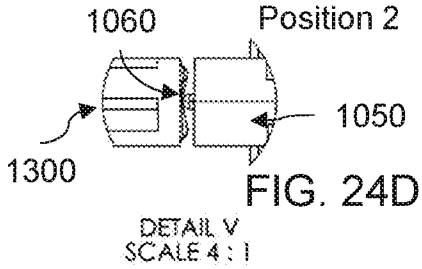
FIG. 24D
FIG. 24E
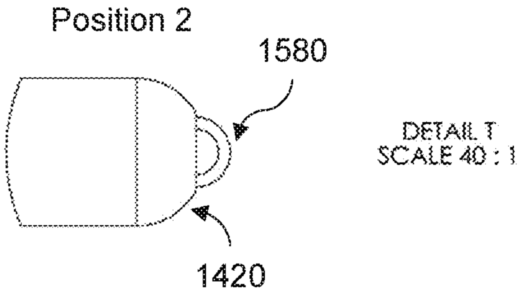

FIG. 25A
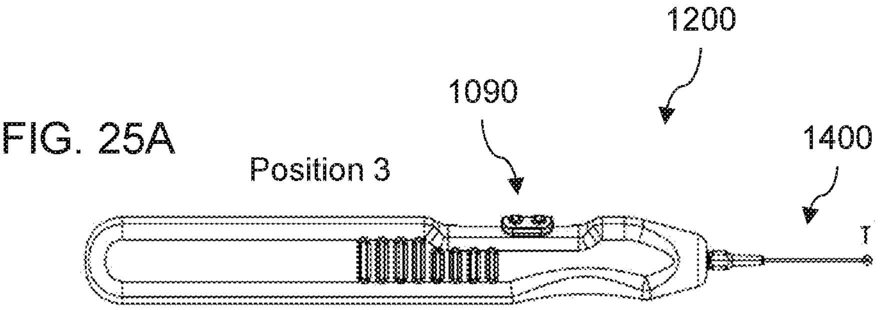
FIG. 25B
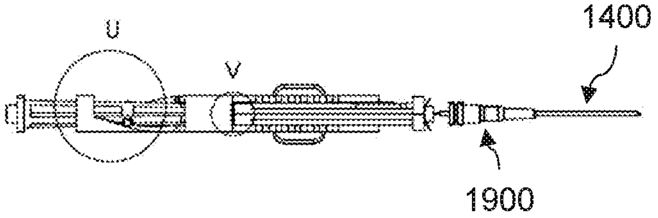
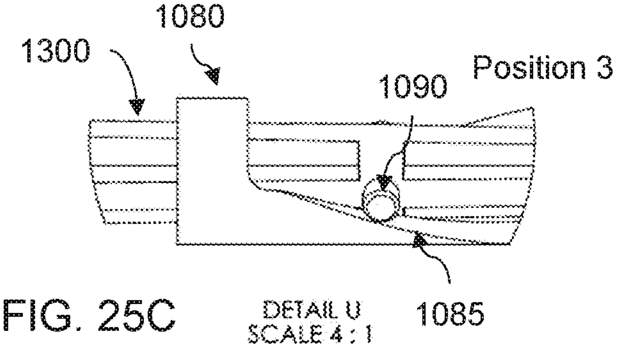
FIG. 25C
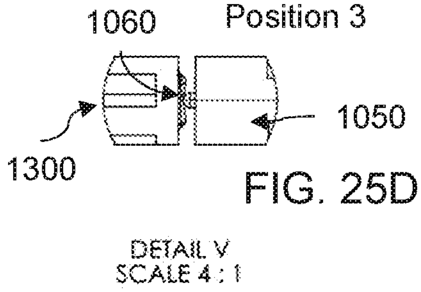
FIG. 25D
FIG. 25E
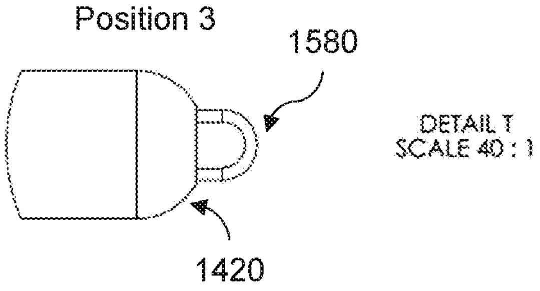

FIG. 26A
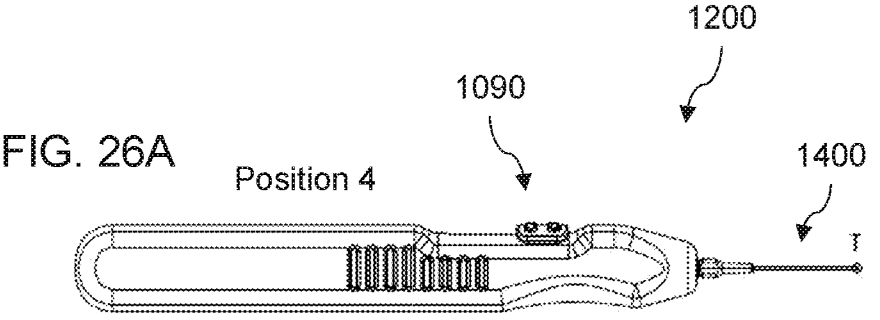
FIG. 26B
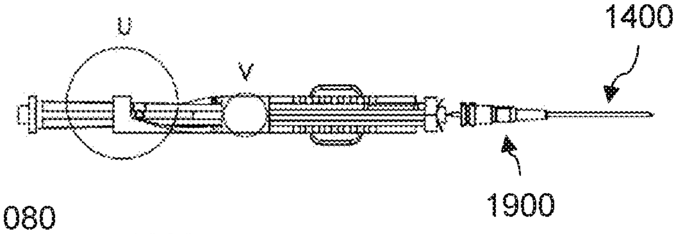
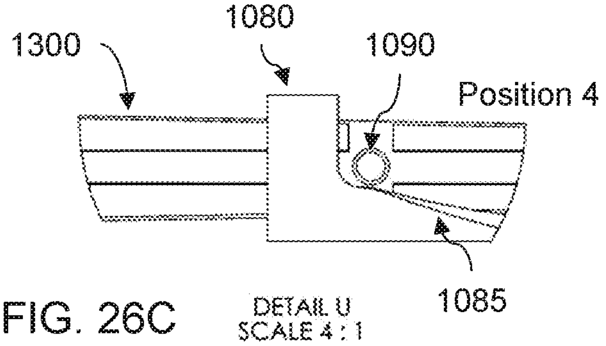
FIG. 26C
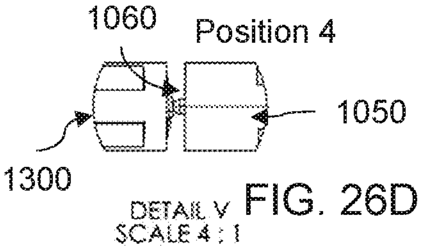
FIG. 26D
FIG. 26E
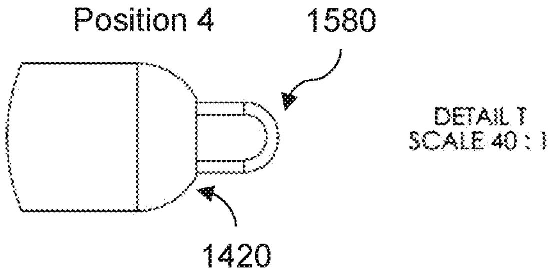

DEVICE, METHODS AND SYSTEM FOR PERFORMING INCISIONS OR EXCISIONS IN THE TRABECULAR MESHWORK

CROSS-REFERENCE TO RELATED APPLICATIONS

The present application is a continuation of International patent application No. PCT/CA2026/050420, filed Mar. 18, 2026, which claims the benefit of priority to Great Britain Patent Application Serial Number 2510313.6, filed Jun. 27, 2025, the entire contents of each of which is incorporated herein by reference.

TECHNICAL FIELD

The present disclosure relates generally to the field of ophthalmic devices and, more specifically, to medical devices, methods, and systems for performing incisions or excisions in the trabecular meshwork.

BACKGROUND

Glaucoma is a progressive optic neuropathy and a leading cause of irreversible blindness worldwide. The trabecular meshwork ("TM") is a porous tissue network overlying Schlemm's canal ("SC"), through which aqueous humor drains from the anterior chamber via collector channels. In glaucoma, elevated flow resistance through the TM, particularly through the juxtacanalicular tissue ("JCT") and inner wall of SC, impairs aqueous outflow and increases intraocular pressure ("IOP").

In recent years, there has been an increasing focus on advancements in minimally invasive techniques for the surgical treatment of glaucoma. This shift has largely been driven by the limitations and risks associated with conventional incisional procedures such as trabeculectomy and tube shunt implantation, despite their well-documented long-term effectiveness. Traditional surgical approaches often present challenges, including variable IOP reduction, extended visual recovery periods, heightened risk of post-operative infection and vision loss, frequent follow-up requirements, and potential for long-term surgical failure.

In response to these issues, various minimally invasive glaucoma surgery (MIGS) techniques have been developed to reduce surgical trauma and mitigate complications associated with full-thickness procedures. Methods such as endoscopic cyclophotocoagulation, ab interno trabeculectomy, and canaloplasty utilizing an illuminated microcatheter have emerged as alternatives, primarily aiming to eliminate the need for a filtering bleb. However, these approaches are not without drawbacks. A key concern is the substantial cost associated with the specialized equipment required for these procedures, which can present a financial burden to healthcare providers, hospitals, and surgical centers. Furthermore, certain techniques involve a steep learning curve, potentially limiting widespread adoption.

WO 2013/163034 (Kahook), which underlies the commercial Kahook Dual Blade (KDB), discloses a dual-blade device for cutting trabecular meshwork tissue. The device includes a handle, a tool shaft, a beveled platform with an insertion blade tip, and first and second lateral blades along the sides of the platform. While effective in creating a direct outflow pathway, the KDB procedure is limited by its reliance on manual control, which may lead to variability in the depth and extent of the incision due to physiological hand tremors (i.e., averages of 50-100 μm have been reported in displacement amplitude). Additionally, the KDB requires blade reorientation and repositioning mid-procedure to access both the nasal and temporal trabecular segments, introducing a gonioscopic recentration step with associated tremor, time cost, and risk of tissue damage.

Therefore, there remains a need for improved surgical instruments that are simple, cost-effective, and precise.

SUMMARY

The following Summary provides an overview of certain embodiments of the invention and is not intended to limit the scope of the appended claims. This Summary is not intended to identify key aspects or essential aspects of the claimed subject matter, nor is it intended to be used to determine the scope of the claimed subject matter. The full scope of the invention is defined by the claims appended hereto.

As embodied and broadly described herein, the present disclosure relates to an ophthalmic surgical device configured to perform trabecular meshwork incision or excision in an eye. The device comprises a blade having adjustable penetration depth and a distal cutting end, and a tissue reference surface configured to contact ocular tissue surface, e.g., sclera or limbus, and define a reference for the adjustable penetration depth. The blade distal cutting end has a bidirectional cutting geometry configured to enable incision or excision of trabecular meshwork in opposing circumferential directions while maintaining the device in the eye.

In some embodiments, the device further comprises a delivery member having a body extending along a longitudinal axis and a distal interface end defining the tissue reference surface, the body defining a lumen extending therethrough, wherein the blade is disposed at least partially within the lumen and is movable relative to the delivery member along the longitudinal axis between a retracted position and an extended position. In some embodiments, the device further comprises a depth control system operably coupled to the blade and configured to limit penetration of the blade into target tissue, the depth control system comprising a depth-limiting mechanism having a plurality of selectable depth presets, each depth preset corresponding to a predetermined maximum displacement of the distal cutting end relative to the tissue reference surface, wherein the depth-limiting mechanism is operative to constrain advancement of the blade to the penetration depth corresponding to the selected depth preset.

As embodied and broadly described herein, the present disclosure relates to a method of performing trabecular meshwork incision or excision. The method comprises providing an ophthalmic surgical device comprising a blade having adjustable penetration depth and a distal cutting end with bidirectional cutting geometry, a tissue reference surface configured to contact ocular tissue surface, e.g., sclera or limbus, and define a reference for the adjustable penetration depth, and a depth control system operably coupled to the blade, the depth control system comprising a depth-limiting mechanism having a plurality of selectable depth presets; selecting a depth preset; positioning the tissue reference surface of the device against a surface of the eye and displacing the blade to extend the distal cutting end by a distance corresponding to the selected depth preset; performing a first incision or excision in a first circumferential direction of the trabecular meshwork with the distal cutting end; and performing, while maintaining the device in the anterior chamber, a second incision or excision in an opposite circumferential direction of the trabecular meshwork with the distal cutting end.

As embodied and broadly described herein, the present disclosure relates to a blade assembly for trabecular meshwork incision or excision comprising: (a) a cutting blade configured to incise and excise trabecular meshwork; (b) a blade extension length relative to a tissue reference surface dimensioned in the range of 200-350 μm, corresponding to a thickness of trabecular meshwork and a position of Schlemm's canal, and configured to span substantially the full thickness of trabecular meshwork while limiting penetration beyond the outer wall of Schlemm's canal.

As embodied and broadly described herein, the present disclosure relates to a method of performing trabecular meshwork incision or excision in an operating room comprising: positioning a patient under an operating microscope; visualizing an anterior chamber angle using a gonioscopy lens; inserting the device described herein through a corneal incision into an anterior chamber; engaging trabecular meshwork adjacent to Schlemm's canal with a cutting element of the device; incising or excising trabecular meshwork along Schlemm's canal using the device.

As embodied and broadly described herein, the present disclosure relates to a surgical platform for trabecular meshwork incision or excision comprising: a tissue-cutting device with blade depth control and integrated imaging, and optionally adjustable geometry; a computing device configured to record one or more parameters during each procedure selected from (a) selected working angle from articulation joint, when the device includes the adjustable geometry; b) selected blade depth preset; c) duration of blade engagement with trabecular meshwork; d) incision or excision arc length; e) real-time imaging frames; (f) surgeon identifier; (g) patient identifier, optionally encrypted, and HIPAA-compliant; and postoperative IOP reduction and adverse events.

As embodied and broadly described herein, the present disclosure relates to an ophthalmic surgical device configured to perform trabecular meshwork incision or excision comprising: (a) a blade having adjustable penetration depth; a tissue reference surface configured to contact ocular tissue surface, e.g., sclera or limbus, and define a reference for the adjustable penetration depth; a bidirectional cutting geometry enabling incision or excision of trabecular meshwork in opposing circumferential directions while maintaining the device in the eye (i.e., without removing the device from the eye); and an imaging system aligned with or proximate to the blade and configured to visualize trabecular meshwork during incision or excision.

As embodied and broadly described herein, the present disclosure relates to a goniotomy device comprising: a blade having adjustable penetration depth relative to a tissue reference surface; a tissue reference surface configured to contact contact ocular tissue surface, e.g., sclera or limbus, and define a reference for the adjustable penetration depth; and a bilateral cutting edge or cutting geometry configured to incise or excise trabecular meshwork in opposite circumferential directions while maintaining the device in the eye (i.e., without removing the device from the eye).

As embodied and broadly described herein, the present disclosure relates to a surgical system for performing trabecular meshwork incision or excision along Schlemm's canal comprising: (a) a hand-held ophthalmic surgical device having: a cutting element configured to incise or excise trabecular meshwork in opposing circumferential directions from a single corneal entry site while maintaining the device in an anterior chamber (i.e., without removal of the device from the anterior chamber), a tissue reference surface configured to contact contact ocular tissue surface, e.g., sclera or limbus, and define a reference for the adjustable penetration depth, and a depth-limiting system referenced to the tissue reference surface and configured to mechanically decouple physiologic surgeon hand tremor from blade penetration depth; and (b) an imaging system configured to visualize trabecular meshwork during the incision or excision, the imaging system comprising a camera with an imaging axis substantially aligned with a longitudinal axis of the cutting element; wherein the system is configured for use under an operating microscope with gonioscopy lens, and optionally at a slit-lamp biomicroscope in an office setting.

As embodied and broadly described herein, the present disclosure relates to a surgical system for trabecular meshwork incision or excision comprising: a reusable handle and proximal segment assembly; a plurality of sterile, single-use distal cartridges, each distal cartridge comprising a delivery member, a tissue reference surface, and a blade assembly; and a quick-connect coupling interface configured to enable a user to detachably connect a selected distal cartridge to the reusable handle.

All features of the embodiments described herein, which are not mutually exclusive, can be combined with one another. Elements of one embodiment can be utilized in other embodiments without further mention. Other aspects and features of the present invention will become apparent to those ordinarily skilled in the art upon review of the following description of specific embodiments in conjunction with the accompanying drawings.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein. In the drawings:

FIG. 23A to FIG. 23E are non-limiting views illustrating various positions of the depth control system and blade deployment for the device of FIG. 21, in accordance with embodiments of the present disclosure.

FIG. 24A to FIG. 24E are non-limiting views illustrating additional positions of the depth control system and blade deployment for the device of FIG. 21, in accordance with embodiments of the present disclosure.

FIG. 25A to FIG. 25E are non-limiting views illustrating further positions of the depth control system and blade deployment for the device of FIG. 21, in accordance with embodiments of the present disclosure.

FIG. 26A to FIG. 26E are non-limiting views illustrating additional configurations of the depth control system for the device of FIG. 21, in accordance with embodiments of the present disclosure.

Figure 1:
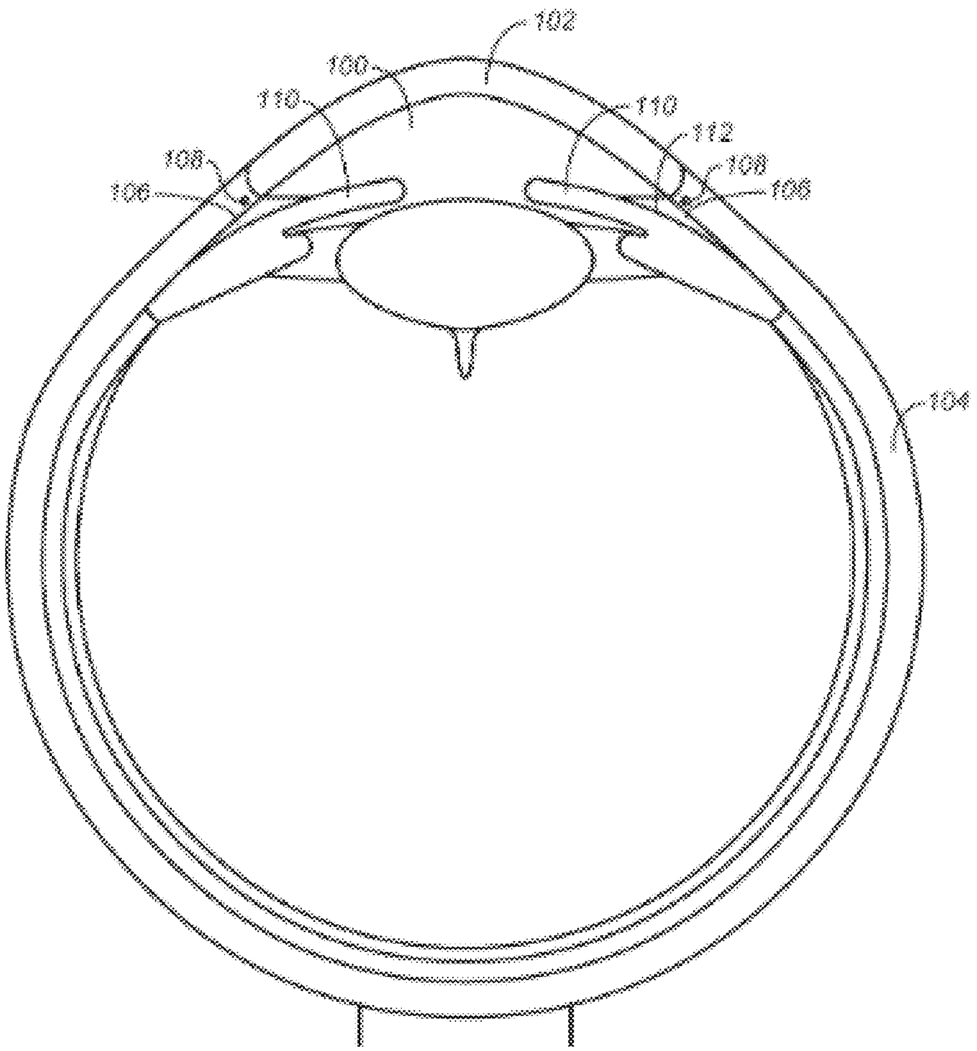
FIG. 1 is a cross-sectional schematic diagram of a human eye.

In the drawings, exemplary embodiments are illustrated by way of example. It is to be expressly understood that the description and drawings are only for the purpose of illustrating certain embodiments and are an aid for understanding. They are not intended to be a definition of the limits of the invention.

DETAILED DESCRIPTION

The following description is not intended to be a detailed catalog of all the different ways in which the device may be made or used, or all the features that may be added. For example, features shown with one version may be used with other versions, and features shown with a particular version may be left out of that version. In addition, many variations and additions to the versions suggested here will be apparent to those skilled in the art in light of this disclosure, and such variations and additions do not depart from the scope of the invention. Hence, the following description is intended to illustrate some particular versions of the device, and not to list every possible variation. The disclosure should be read together with the accompanying drawings, where like reference numbers refer to like parts throughout the several views.

Ophthalmic Surgical Device and Methods

The present invention relates to an ophthalmic surgical device and methods for treating glaucoma and other conditions requiring reduction of intraocular pressure using minimally invasive surgical techniques. The device is configured for incision or excision of trabecular meshwork tissue in an eye, and is particularly suited for minimally invasive glaucoma surgery (MIGS) procedures including goniotomy, trabeculotomy, and other angle-based surgeries aimed at reducing intraocular pressure by improving how fluid drains from the eye through the trabecular meshwork and into Schlemm's canal.

In a broad aspect, the invention relates to a device comprising a blade having adjustable penetration depth and a distal cutting end with bidirectional cutting geometry; and a tissue reference surface configured to contact contact ocular tissue surface, e.g., sclera or limbus, and define a reference for the adjustable penetration depth. The bidirectional cutting geometry enables incision or excision of trabecular meshwork in opposing circumferential directions while maintaining the device in the eye.

The invention addresses at least one or more technical problems with existing goniotomy, trabeculotomy, and other angle-based surgeries aimed at reducing intraocular pressure. For example, blade depth variability caused by physiological hand tremors during microsurgery; the need to reposition conventional surgical devices mid-procedure to achieve bidirectional tissue incision; and limitations of existing devices in providing reproducible, tissue-layer-specific cutting depths.

Even the steadiest surgeon's hands have small involuntary movements (natural hand tremor), typically ranging from 50 to 100 micrometers during delicate tasks. With conventional goniotomy devices, this tremor transfers directly to the blade, causing the cutting depth to vary by amounts comparable to the full thickness of the trabecular meshwork. The device described herein solves this problem by mechanically isolating the blade depth from hand tremor. The technical effect is that two surgeons with different levels of hand steadiness achieve the same precise cutting depth when using the same depth preset. In other words, the device converts a variable human factor (hand tremor) into a fixed, reproducible outcome (preset cutting depth). This can be achieved through two cooperating features: first, the tissue reference surface (acting as a stabilizing contact point) rests against the eye surface, so that tremor energy is absorbed by this contact rather than affecting blade depth; second, the depth control system mechanically limits how far the blade can extend. The result is that cutting depth accuracy depends on the device's design, not on the surgeon's hand steadiness.

In some embodiments, the device further comprises a body configured for manual gripping; a delivery member extending along a longitudinal axis and having a distal interface end defining an aperture, the delivery member defining a lumen therethrough; and a blade disposed at least partially within the lumen and movable between a retracted position and an extended position.

In some embodiments, the blade is movable from a retracted position, in which the blade is contained within the lumen, to an extended position, in which the distal cutting end extends beyond the distal interface end.

In some embodiments, the distal interface end is configured to contact the eye tissue surface as a stabilizing reference point and provides a mechanical datum from which blade depth is measured. The technical effect is further reduction of blade depth variability caused by hand tremors, patient movement, or positional shifts during surgery.

In some embodiments, the device further comprises a depth control system comprises a depth-limiting mechanism having a plurality of selectable depth presets. Each depth preset corresponds to a predetermined maximum displacement of the distal cutting end relative to the tissue reference surface. Non-limiting examples of structures forming the depth-limiting mechanism include indexed detent mechanisms, cam-and-follower arrangements, lead screws, ratchet mechanisms, spring-loaded stops, adjustable collars, graduated sleeves, and mechanical indexing structures.

In some embodiments, the depth control system is operably coupled to the blade and configured to limit blade penetration into target tissue. The technical effect of the depth control system is reduction of blade depth variability during use, which would otherwise occur due to physiological hand tremors, involuntary micro-movements, or patient movement. By constraining the blade to specific depth settings, the depth control system reduces the risk of damage to non-target tissues such as the ciliary body, iris root, scleral spur, or collector channel ostia.

In some embodiments, the distal interface end cooperates with the depth control system to provide dual-constraint depth control, wherein the distal interface end establishes a tissue-referenced zero point and the depth control system limits blade excursion relative thereto. The technical effect is mechanical decoupling of surgeon hand tremor from blade penetration depth, such that blade depth variance is maintained at approximately +25 μm or less despite hand tremor displacement amplitudes of 50-100 μm.

In some embodiments, the device is configured for use in operating room gonioscopy procedures, office-based slit-lamp biomicroscopy procedures, or both.

In some embodiments, the depth control system includes a manual actuator operatively linked to the depth-limiting mechanism, the actuator having discrete, selectable positions corresponding to predetermined blade extension distances.

In some embodiments, the selectable depth presets are in the range of 150 μm to 250 μm, corresponding to anatomical dimensions of the trabecular meshwork and Schlemm's canal.

In some embodiments, the depth presets comprise approximately 150 μm (for thin trabecular meshwork, e.g., pediatric patients), 190 μm (average adult anatomy), 220 μm (thickened trabecular meshwork), and 250 μm (maximum penetration limit). The depth control system may include a mechanical indexing structure providing tactile feedback (click, detent engagement, or resistance change) when a depth preset is selected. This tactile feedback confirms to the surgeon that a specific depth preset has been properly engaged, enhancing confidence and precision during the procedure.

In some embodiments, the mechanical indexing structure provides audible feedback accompanying the tactile feedback, providing dual sensory confirmation of depth preset engagement. This dual sensory feedback (tactile and audible) helps ensure accurate depth selection even in challenging surgical environments.

In some embodiments, the distal interface end and depth control system cooperate to provide dual-constraint depth control, providing two independent safeguards against excessive blade penetration.

In some embodiments, the tissue reference surface comprises a foot, flange, ledge, shoulder, or abutment surface configured to engage contact ocular tissue surface, e.g., sclera or limbus, and define a reference for the adjustable penetration depth. These structural configurations provide a stable contact point against the curved surface of the eye, improving control and alignment of the device during blade actuation In some embodiments, the distal cutting end comprises a curved or arcuate distal apex and laterally extending cutting edges on opposing sides of the blade body, the cutting edges diverging laterally from the apex to enable bidirectional cutting. The cutting edges may be substantially mirror-symmetric for equivalent cutting performance in both lateral directions.

In some embodiments, the blade cutting end has a width of approximately 300 μm, dimensioned to span the meridional width of Schlemm's canal (196-239 μm in adults).

In some embodiments, the tissue reference surface contact ocular tissue surface, e.g., sclera or limbus, to reduce blade depth variability caused by hand tremor, mechanically decoupling hand movement from blade penetration depth.

In some embodiments, the device comprises an imaging system including an imaging device configured to capture real-time images proximate to the distal cutting end, allowing visualization of blade position and tissue engagement during the procedure.

In some embodiments, the imaging system comprises a camera with an imaging axis aligned with the longitudinal axis of the blade, enabling direct visualization from the blade's perspective.

In some embodiments, the blade comprises a ramp or wedge geometry configured to elevate trabecular meshwork tissue prior to incision, facilitating tissue separation and cutting precision.

In a broad aspect, the invention relates to a method of performing trabecular meshwork incision or excision comprising: providing the ophthalmic surgical device; positioning the tissue reference surface against the eye; performing a first incision or excision in a first circumferential direction; and performing, while maintaining the device in the anterior chamber, a second incision or excision in an opposite circumferential direction.

In some embodiments, incisions are performed along Schlemm's canal spanning one or more quadrants (nasal, temporal, superior, inferior) of trabecular meshwork, with combined incisions spanning 90° to 180° of trabecular meshwork.

In some embodiments, incision or excision of trabecular meshwork exposes Schlemm's canal and one or more collector channel ostia to aqueous humor outflow, reducing intraocular pressure.

In some embodiments, the method is performed in an operating room under an operating microscope with gonioscopy lens visualization, or in an office setting at a slit-lamp biomicroscope.

In some embodiments, the method is performed in an operating room under an operating microscope with binocular visualization via a gonioscopy lens. The operating microscope provides magnified, stereoscopic visualization of the anterior chamber angle, and the gonioscopy lens enables direct visualization of the trabecular meshwork and Schlemm's canal during the procedure.

In some embodiments, the method is performed in an office or clinic setting at a slit-lamp biomicroscope. The slit-lamp biomicroscope provides magnified visualization of the anterior segment, and may be combined with a gonioscopy lens for visualization of the anterior chamber angle. This office-based approach may reduce costs and improve patient convenience compared to operating room procedures.

In some embodiments, the method comprises positioning the distal interface end against contact ocular tissue surface, e.g., sclera or limbus, to reduce blade depth variability, and selecting a depth preset via the manual actuator prior to incision.

In some embodiments, the depth preset is selected from values of 150 μm, 190 μm, 220 μm, or 250 μm, and selection can be confirmed by tactile and/or audible feedback.

In some embodiments, the method comprises monitoring the surgical field using an imaging device associated with the device.

In some embodiments, the first circumferential direction is nasal and the second is temporal, and bidirectional incisions are performed while maintaining fixed gonioscopy lens position, fixed microscope position, and a single corneal incision.

In a broad aspect, the invention relates to a surgical system comprising: a reusable handle and proximal segment assembly; a plurality of sterile, single-use distal cartridges each comprising a delivery member, tissue reference surface, and blade assembly; and a quick-connect coupling interface for detachable connection of cartridges to the handle.

In some embodiments, each distal cartridge comprises a blade extension depth in the range of 150-250 μm, with specific variants at 150 μm, 190 μm, 220 μm, and 250 μm. Cartridge variants may be color-coded or labeled for identification.

In some embodiments, the quick-connect coupling interface comprises bayonet connectors, twist-lock mechanisms, snap-fit engagements, or magnetic couplings, and provides tactile and/or audible feedback confirming cartridge engagement.

In some embodiments, distal cartridges comprise variants with different cutting geometries: bilateral (bidirectional cutting edges), angled (cutting edge at angle to longitudinal axis), or narrow (reduced-width blade profile). A narrow cutting geometry comprises a reduced-width blade profile, which may be suited to patients with narrower Schlemm's canal dimensions or when a more conservative incision width is desired.

In some embodiments, each distal cartridge is individually sterile-packaged and includes a unique identifier (barcode, RFID tag, or QR code) for tracking cartridge type, sterilization batch, and post-operative outcome correlation. The unique identifier may be scanned or read prior to or during the surgical procedure to associate cartridge information with patient records, enabling post-operative analysis of outcomes correlated with cartridge type, blade extension depth, cutting geometry, sterilization batch, manufacturing lot, or other parameters.

In some embodiments, each distal cartridge includes a mechanical keying feature configured to permit connection only of compatible cartridges to the reusable handle, ensuring proper functional compatibility between handle and cartridge components. The mechanical keying feature may comprise one or more projections, recesses, grooves, ridges, tabs, slots, or geometric profiles disposed on the distal cartridge that correspond to complementary features on the reusable handle. The mechanical keying feature is configured such that a distal cartridge having an incompatible keying configuration cannot be physically connected to a handle having a non-matching keying configuration. In some embodiments, the mechanical keying feature varies between handle generations, such that distal cartridges designed for a first-generation handle cannot be connected to a second-generation handle, or vice versa, thereby ensuring proper functional compatibility between handle and cartridge components. In some embodiments, the mechanical keying feature additionally or alternatively distinguishes between cartridge types, such as cartridges configured for different blade extension depths or different cutting geometries, to prevent inadvertent selection of an incorrect cartridge type.

Relevant Anatomical Structures

Relevant structures of the eye will first be briefly described to provide background context for the anatomical terms and tissue structures referenced throughout the present disclosure.

FIG. 1 is a schematic cross-sectional diagram of a human eye, illustrating the anatomical structures relevant to the present invention. Certain anatomical details, well known to those skilled in the art, have been omitted for clarity.

The anterior chamber 100 is shown as bounded on its anterior surface by the cornea 102. The cornea 102 is connected on its periphery to the sclera 104, which is a tough fibrous tissue forming the white shell of the eye. Trabecular meshwork 106 is located on the outer periphery of the anterior chamber 100. The trabecular meshwork 106 extends 360 degrees circumferentially around the anterior chamber 100. Located on the outer peripheral surface of the trabecular meshwork 106 is Schlemm's canal 108. Schlemm's canal 108 extends 360 degrees circumferentially around the meshwork 106. At the apex formed between the iris 110, meshwork 106, and sclera 104, is angle 112. The trabecular meshwork 106 is a loosely organized, porous network of tissue that overlies the Schlemm's canal 108. A fluid, known as aqueous humor, is continually produced in the anterior chamber 100 of the eye. In healthy individuals, aqueous humor flows through the trabecular meshwork 106, into Schlemm's canal 108 and out of the eye through a series of ducts called collector channels. In patients who suffer from glaucoma, the drainage of aqueous humor from the eye may be impaired by elevated flow resistance through the trabecular meshwork 106, thereby resulting in an increase in intraocular pressure.

First and Second Implementations—Device Structure and Configuration

Figure 2A:
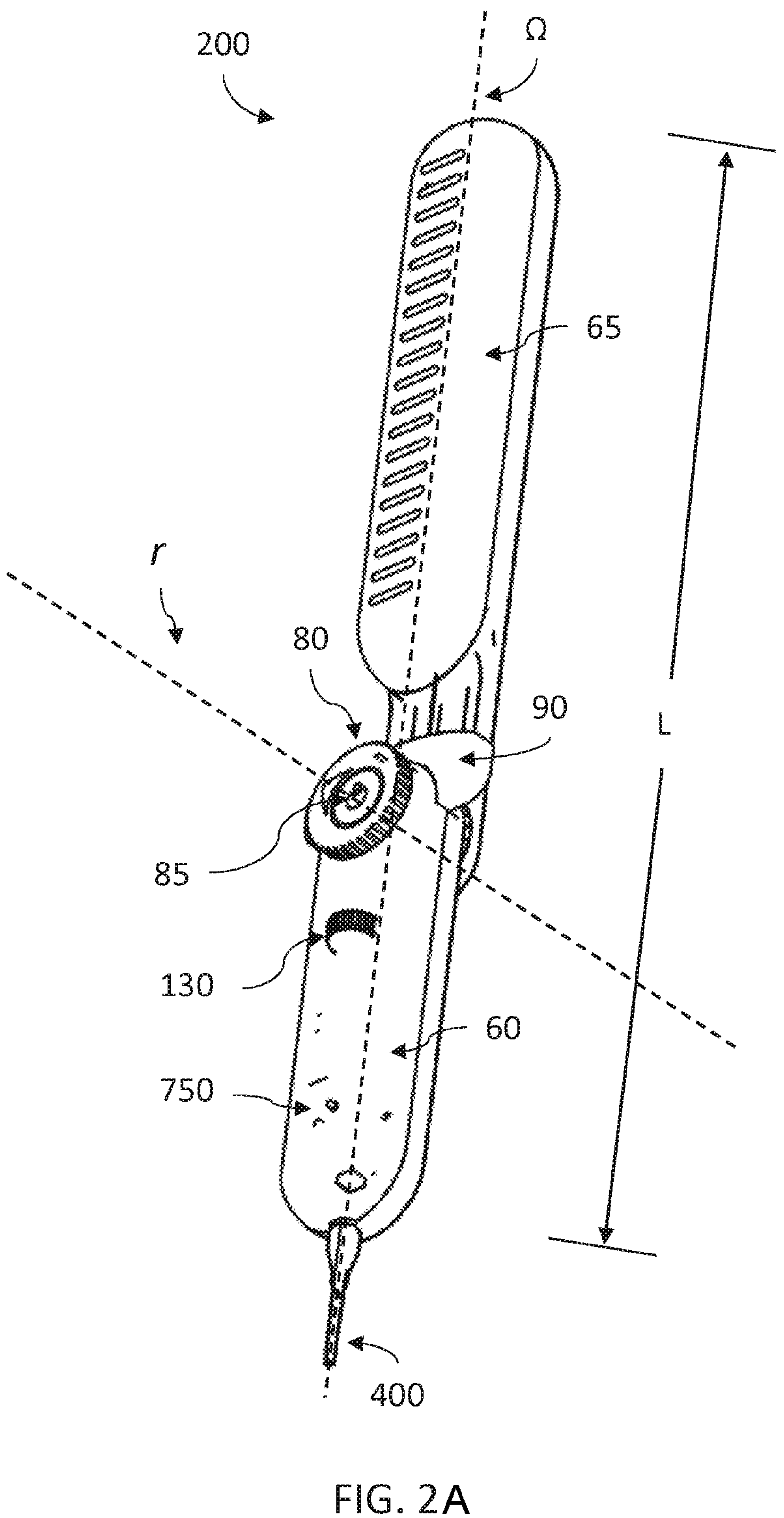
FIG. 2A is a non-limiting perspective view of a device configured to perform ocular incisions, in accordance with embodiments of the present disclosure.
Figure 2B:
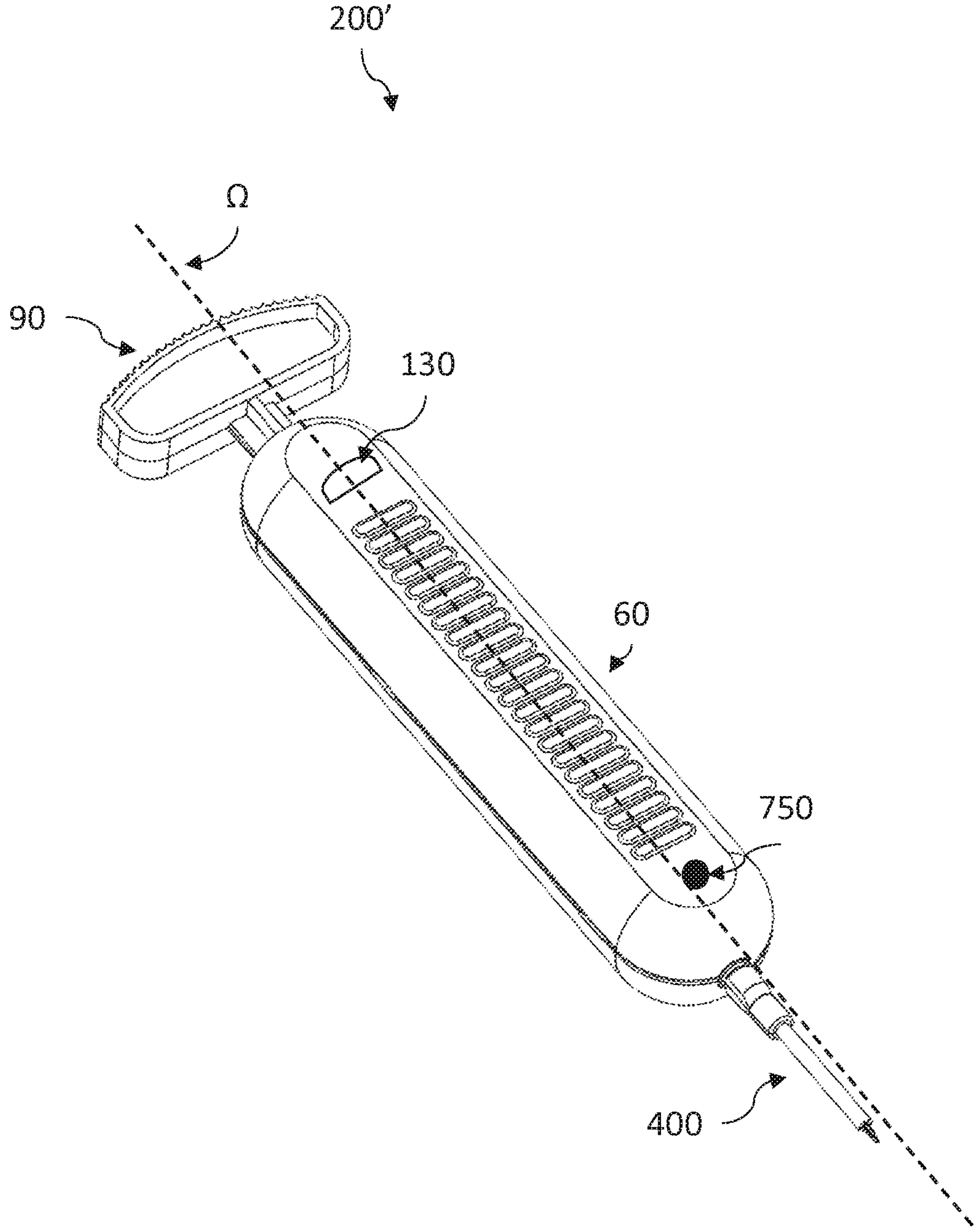
FIG. 2B is another non-limiting perspective view of a device configured to perform ocular incisions, in accordance with embodiments of the present disclosure.

Referring now to FIGS. 2A and 2B, non-limiting implementations of devices arranged and configured in accordance with certain features, aspects, and advantages of the present disclosure are illustrated. The illustrated device implementations can be used for performing an incision in an eye structure. In particular, the devices can be used to perform an incision in the trabecular meshwork for reducing intraocular pressure or can be any other type of device that would benefit from any or all of the later described features, aspects and advantages of the present disclosure.

In a first implementation, the device 200 may include at least two segments: a proximal segment 65 for grasping by a user and a distal segment 60 that includes components for the desired ophthalmologic procedure, as shown in FIG. 2A.

In some embodiments, the proximal segment 65 may have at least a segment of the surface thereof which is raised, depressed, grooved, or textured to improve hold by the user or to improve comfort of the user.

In some embodiments, the distal segment 60 can be separated from the device 200 for decommissioning, discarding, sterilization, and the like. Alternatively, or additionally, the proximal segment 65 can be separated from the device 200 for decommissioning, discarding, sterilization, and the like.

In some embodiments, the distal segment 60 extends along longitudinal axis Q, which can coincide with corresponding longitudinal axis of the proximal segment 65 when both segments are in a working angle of 0°, i.e., in other words, when both segments are aligned along the longitudinal axis Q of the distal segment 60.

Figure 3:
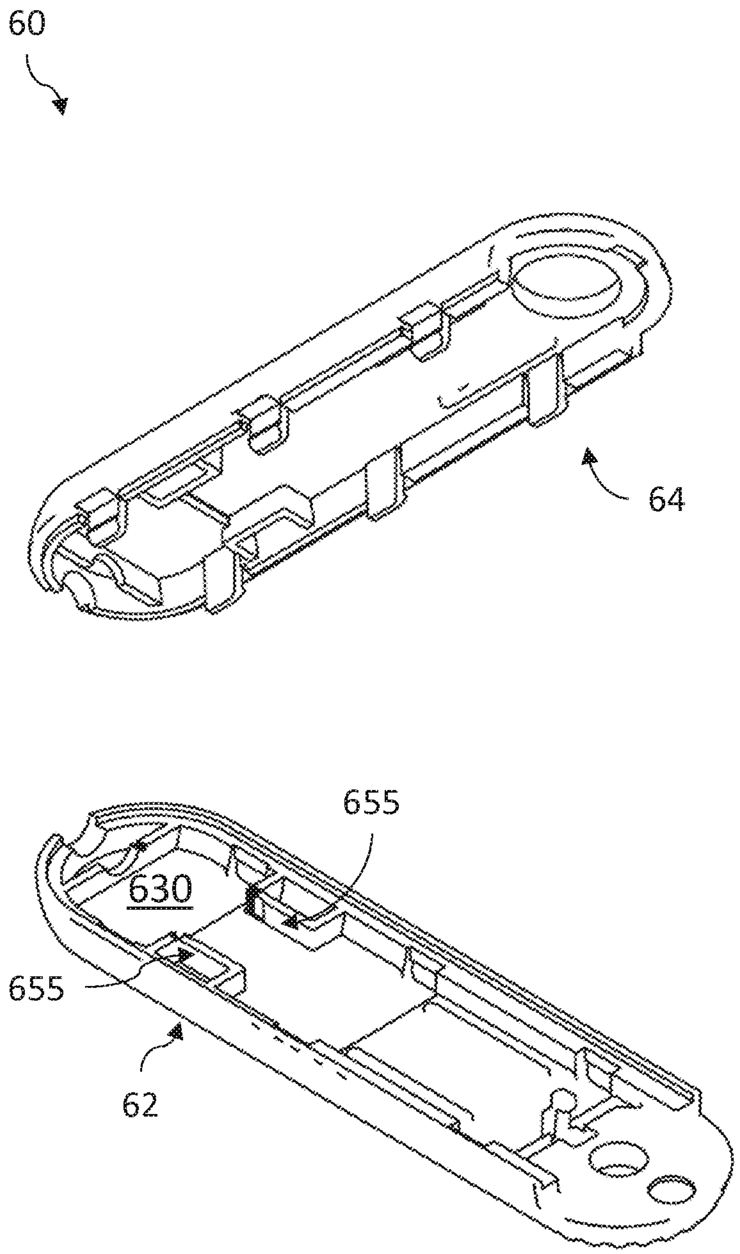
FIG. 3 shows a non-limiting perspective view of disassembled top and bottom portions of the distal segment of the device of FIG. 2A, in accordance with embodiments of the present disclosure.
Figure 4:
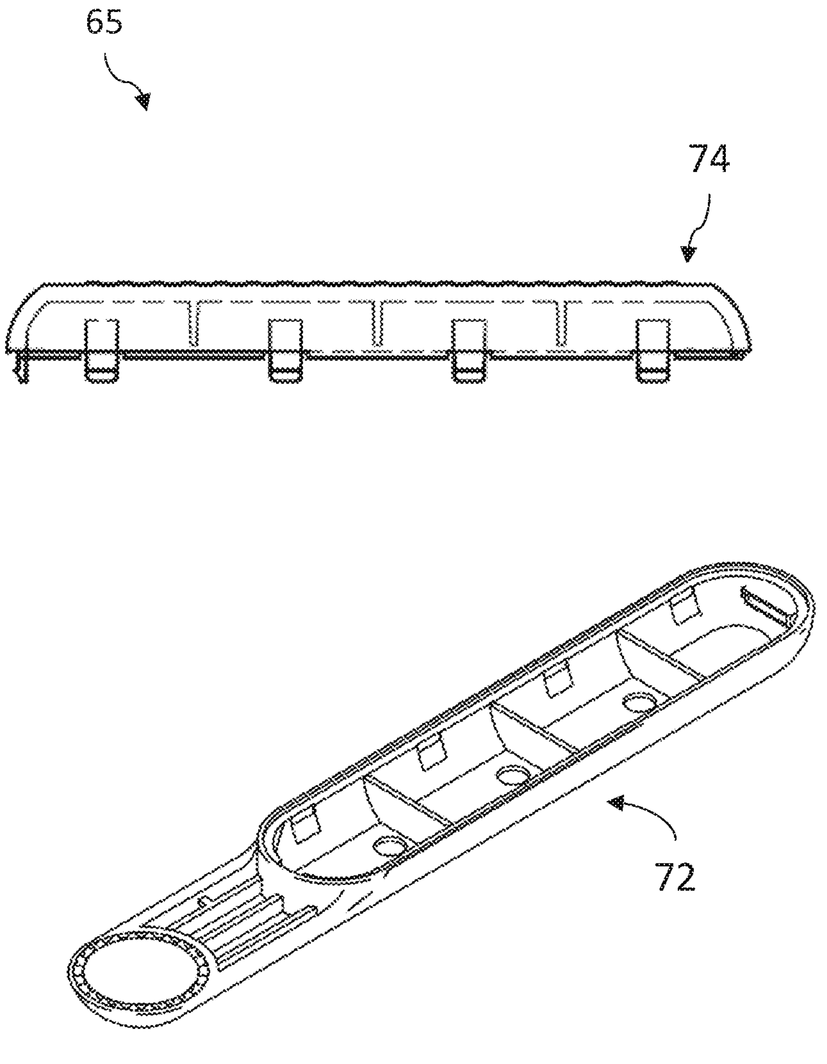
FIG. 4 shows a non-limiting side view of disassembled top and bottom portions of the proximal segment of the device of FIG. 2A, in accordance with embodiments of the present disclosure.

In some embodiments, the distal segment 60 can be formed with first and second housing portions 62, 64, as shown in FIG. 3. For example, first and second housing portions 62, 64 may be configured to assemble one onto another through suitable coupling means. In some embodiments, the proximal segment 65 can be formed with first and second housing portions 72, 74, as shown in FIG. 4. For example, first and second housing portions 72, 74 may be configured to assemble one onto another through any suitable coupling means. Examples of suitable means are described in WO 2024/124336, which is incorporated by reference herein.

In some embodiments, the proximal segment 65 is coupled to the distal segment 60 through any suitable coupling element. In some embodiments, the proximal segment 65 can be coupled to the distal segment 60 through any suitable coupling element allowing the proximal segment 65 to be rotatable relative to the distal segment 60. In some embodiments, the proximal segment 65 can be coupled to the distal segment 60 at a pivot point 85, such that the proximal segment 65 and the distal segment 60 are rotatable relative to each other about a rotation axis r at the pivot point 85, shown in FIG. 2. In some embodiments, the rotation axis r can be substantially perpendicular to the longitudinal axis Q.

In some embodiments, the proximal segment 65 and the distal segment 60 are configured to couple to each other selectively from an unlocked configuration and a locked configuration. In the unlocked configuration, the proximal segment 65 and the distal segment 60 are rotatable relative to each other about the rotation axis rat the pivot point 85. In the locked configuration, the proximal segment 65 and the distal segment 60 remain coupled to each other at an angle selected by the user, unless the unlocked configuration is achieved.

In some embodiments, the device 200 may include a locking mechanism 80 for reversibly securing the proximal segment 65 and the distal segment 60 in the locked configuration. Such locking mechanism 80 can afford a technical effect in that the device 200 can be locked into a position with a desired angle, which allows the user to select a suitable working angle which can facilitate the ophthalmologic procedure. For example, such a working angle can be useful to adapt the device 200 to anatomical variabilities between left and right eye of a user, to anatomical variability between eyes, for different individuals, to personal preference of the user, to use with left or right hand of the medical practitioner, and the like. The user can thus easily select a desired angle, moving the device 200 from a first position to a second position. Advantageously, the user can lock the device 200 to the first or second position using the herein described locking mechanism 80. Advantageously, the user can select the desired angle while the proximal segment 65 and the distal segment 60 remain connected to each other—i.e., there is no requirement to replace one segment with another segment to obtain the desired angle. Further, such capability to select a desired angle can be performed while the device is not in contact with the patient eye as well as while the device is in contact with the patient eye.

In some embodiments, the locking mechanism 80 may be, without being limiting, a knob that can be screwed and unscrewed, a latch or clamp that can reversibly fix the proximal segment 65 and the distal segment 60 in a user desired position, a ratchet-like rotating member that allows for rotation between the proximal segment 65 and the distal segment 60, and the like. Non-limiting examples of suitable locking mechanisms are described in WO 2024/124336, which is incorporated by reference herein.

In some embodiments, the proximal segment 65 and the distal segment 60 may be configured to have a shape that facilitates handling during use of the device 200.

In a second implementation, the device 200' may include a single body 60 for grasping by a user, as shown in FIG. 2B. The body 60 may be ergonomically shaped, contoured, or otherwise dimensioned to facilitate comfortable, stable, and precise handling during use. In some embodiments, the body 60 may include one or more grip-enhancing features, such as textured surfaces, finger rests, or anti-roll geometries, that promote steady manipulation of the device during micro-surgical procedures. The body 60 may further include or house one or more actuation mechanisms configured to control advancement, retraction, or reciprocation of the blade, as described in further detail below.

In some embodiments, the device is capable of being autoclaved or sterilized in some other manner. In some embodiments, the device may be made from any suitable material, such as, but not limited to, polyethylene (PE) including low-density PE, high-density PE, ultra-high molecular weight PE; polypropylene (PP); polytetrafluoroethylene; thermoplastic polyurethane; polycarbonate; polyphtalic acid; acrylic; acrylonitrile butadiene styrene (ABS); silicon; and the like.

In some embodiments, the device may have a total length L suitable for holding and operating with a single hand. In some embodiments, the device may have a total length L of from about 100 mm to about 300 mm, including any values or ranges therein. For example, a length L of about 120 mm, about 130 mm, about 140 mm, about 150 mm, about 160 mm, about 170 mm, about 180 mm, about 190 mm, about 200 mm, about 210 mm, or about 220 mm. For example, a length L of about 140 mm, about 145 mm, or about 150 mm. Preferably, a length L of about 145 mm.

In some embodiments, the device may have a suitable width, which is convenient for holding and operating with a single hand from the user. In some embodiments, the device may have a width of from 6.0 mm to about 9.0 mm, including any values or ranges therein. For example, a width of about 6.5 mm, about 7.0 mm, about 7.5 mm, or about 8.0 mm, preferably a width of about 7.4 mm.

First and Second Implementations-Piercing Member

In a non-limiting practical implementation, the first and second device implementations are equipped with a piercing member 400 configured to pierce a tissue layer, such as an eye tissue layer. In some embodiments, the sclera.

Figure 7A:
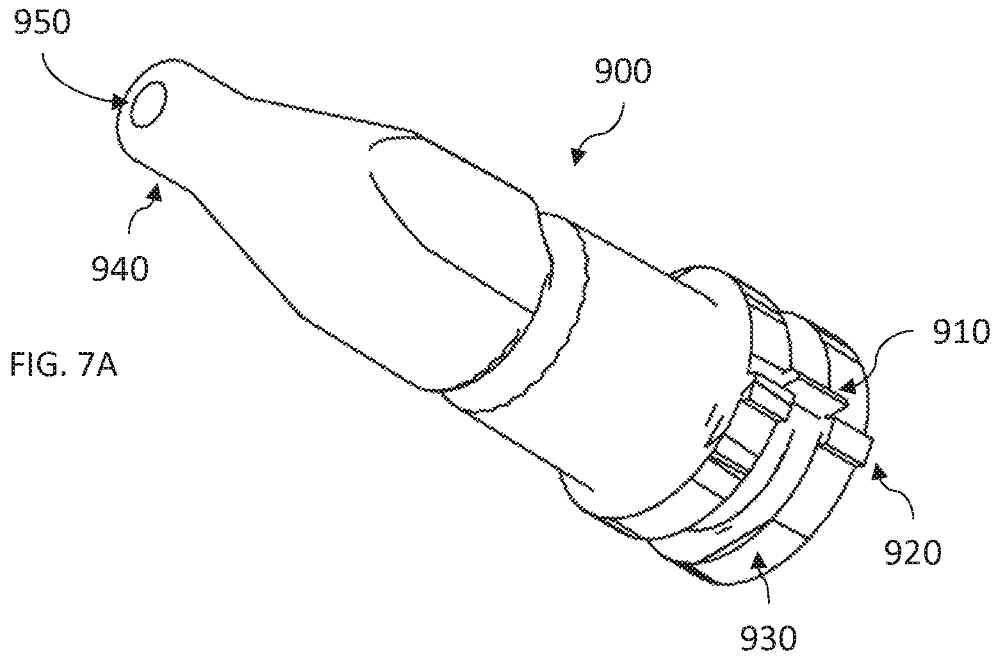
FIG. 7A is a non-limiting perspective view of a hub for use with the device of FIG. 2A or FIG. 2B, in accordance with embodiments of the present disclosure.
Figure 7B:
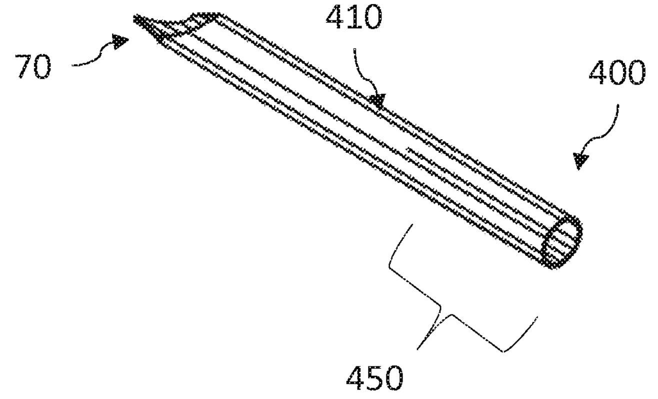
FIG. 7B is a non-limiting perspective view of a piercing element for use with the device of FIG. 2A or FIG. 2B, in accordance with embodiments of the present disclosure.

In some embodiments, the piercing member 400 has an elongated and hollow body 410—the elongated body 410 has an internal wall defining a lumen, which extends along the elongated body 410, as shown in FIG. 7B.

In some embodiments, the piercing member 400 includes a proximal portion 450 that is affixed to or integrally formed with a distal cutting end 940 of distal hub 900, as depicted in FIG. 7A. In some embodiments, the proximal portion 450 of the piercing member 400 may be molded, bonded, welded, or otherwise securely attached to the distal cutting end 940 of hub 900 during the manufacturing process to ensure structural stability and alignment. In certain implementations, at least a segment of the proximal portion 450 of the piercing member 400 may be retained within an internal cavity of the distal hub 900, thereby protecting it from external contact or contamination prior to use.

A distal portion of the piercing member 400 may extend or protrude outwardly through a distal orifice 950 defined in the distal cutting end 940 of hub 900, allowing the piercing member 400 to be exposed and operable for penetration or insertion into an eye tissue layer. This configuration supports efficient deployment of the piercing member 400 while maintaining a compact assembly. The engagement between the piercing member 400 and the hub 900 may also serve to guide or stabilize the piercing motion, improving accuracy and repeatability during use. Optionally, the design may incorporate sealing features or tolerances around the distal orifice 950 to minimize fluid leakage or contamination between the interior of the hub 900 and the external environment.

In some embodiments, the piercing member 400 extends along the longitudinal axis Q.

In some embodiments, the device 200, 200' is configured to perform the perforation in the tissue layer with the piercing member 400.

In some embodiments, the device 200, 200' can be positioned at a first point with respect to the tissue layer and advanced along the longitudinal axis of segment 65 until the piercing member 400 contacts the first surface of the tissue layer. Advantageously, the tissue layer can be intact, i.e., when performing the procedure ab externo on an eye, there is no scleral flap required on the conjunctiva or sclera. When the device 200, 200' is further advanced towards the tissue layer, then the piercing member 400 pierces the tissue layer. Advantageously, the piercing member 400 can perform this piercing with an axial motion (i.e., coaxial with the longitudinal axis). In other words, the piercing motion does not require any rotational movement of the piercing member 400 to pierce into the tissue layer. It will be apparent to the reader that such axial cutting motion is generally safer relative to cutting motions with rotational movements that can cause injury to surrounding tissue.

In some embodiments, the piercing member 400 can be further configured to penetrate through the tissue layer, for example with an axial displacement of the device 200, 200' towards the tissue layer. Advantageously, the piercing member 400 is configured to penetrate at least a portion thereof into and through the tissue layer smoothly and easily with minimum force, therefore it can have a smooth (e.g., polished) outer surface to minimize friction during penetration into and through the tissue layer.

In some embodiments, the piercing member 400 includes a piercing tip 70 at a distal cutting end of body 410. In some embodiments, the piercing tip 70 may have an atraumatic configuration with a sharpness that is optimized for tissue layer entry.

In some embodiments, the piercing tip 70 may have a needle bevel shape, e.g., a sharpened atraumatic angular tip. In some embodiments, the piercing tip 70 may have a cannula-style pointed/machined distal cutting end. In some embodiments, the piercing tip 70 may have a relatively shallow primary bevel angle that allows tissue material to slip over more easily. In some embodiments, the piercing tip 70 may have a primary bevel angle of from about 10° to about 15°. Preferably, the piercing tip 70 is atraumatic with a sharpness optimized for scleral entry.

In some embodiments, the piercing member 400 may be of any gauge suitable for piercing the tissue layer. For example, any size selected from the needle gauge size listed in Table 1:

TABLE 1

Needle Gauge Dimensions

| Needle gauge | Outer diameter (inches) | Outer diameter (mm) | Inner diameter (inches) | Inner diameter (mm) |
|---|---|---|---|---|
| 7 | 0.180 | 4.572 | 0.150 | 3.810 |
| 8 | 0.165 | 4.191 | 0.135 | 3.429 |
| 9 | 0.148 | 3.759 | 0.118 | 2.997 |
| 10 | 0.134 | 3.404 | 0.106 | 2.692 |
| 11 | 0.120 | 3.048 | 0.094 | 2.388 |
| 12 | 0.109 | 2.769 | 0.085 | 2.159 |
| 13 | 0.095 | 2.413 | 0.071 | 1.803 |
| 14 | 0.083 | 2.108 | 0.063 | 1.600 |
| 15 | 0.072 | 1.829 | 0.054 | 1.372 |
| 16 | 0.065 | 1.651 | 0.047 | 1.194 |
| 17 | 0.058 | 1.473 | 0.042 | 1.067 |
| 18 | 0.050 | 1.270 | 0.033 | 0.838 |
| 19 | 0.042 | 1.067 | 0.027 | 0.686 |
| 20 | 0.03575 | 0.9081 | 0.02375 | 0.603 |
| 21 | 0.03225 | 0.8192 | 0.02025 | 0.514 |
| 22 | 0.02825 | 0.7176 | 0.01625 | 0.413 |
| 22s | 0.02825 | 0.7176 | 0.006 | 0.152 |
| 23 | 0.02525 | 0.6414 | 0.01325 | 0.337 |
| 24 | 0.02225 | 0.5652 | 0.01225 | 0.311 |
| 25 | 0.02025 | 0.5144 | 0.01025 | 0.260 |
| 26 | 0.01825 | 0.4636 | 0.01025 | 0.260 |
| 26s | 0.01865 | 0.4737 | 0.005 | 0.127 |
| 27 | 0.01625 | 0.4128 | 0.00825 | 0.210 |
| 28 | 0.01425 | 0.3620 | 0.00725 | 0.184 |
| 29 | 0.01325 | 0.3366 | 0.00725 | 0.184 |
| 30 | 0.01225 | 0.3112 | 0.00625 | 0.159 |
| 31 | 0.01025 | 0.2604 | 0.00525 | 0.133 |
| 32 | 0.00925 | 0.235 | 0.00425 | 0.108 |
| 33 | 0.00826 | 0.210 | 0.00425 | 0.108 |
| 34 | 0.00625 | 0.159 | 0.00200 | 0.051 |

In some embodiments, the piercing member 400 may have a 19G to 30G needle size for versatility across different patient anatomies. Preferably, the piercing member 400 has a 19G to 27G needle size. Advantageously, the piercing member 400 can act as both a guide and structural stabilizer of the blade (which is described elsewhere in this text).

In some embodiments, the piercing member 400 may be composed of any suitable medical-grade material, such as for instance medical-grade stainless steel.

First and Second Implementations-Cannula

In some embodiments, the device 200, 200' is further equipped with a cannula 300 which is configured for reciprocal movement within the lumen of the piercing member 400.

Figure 7C:
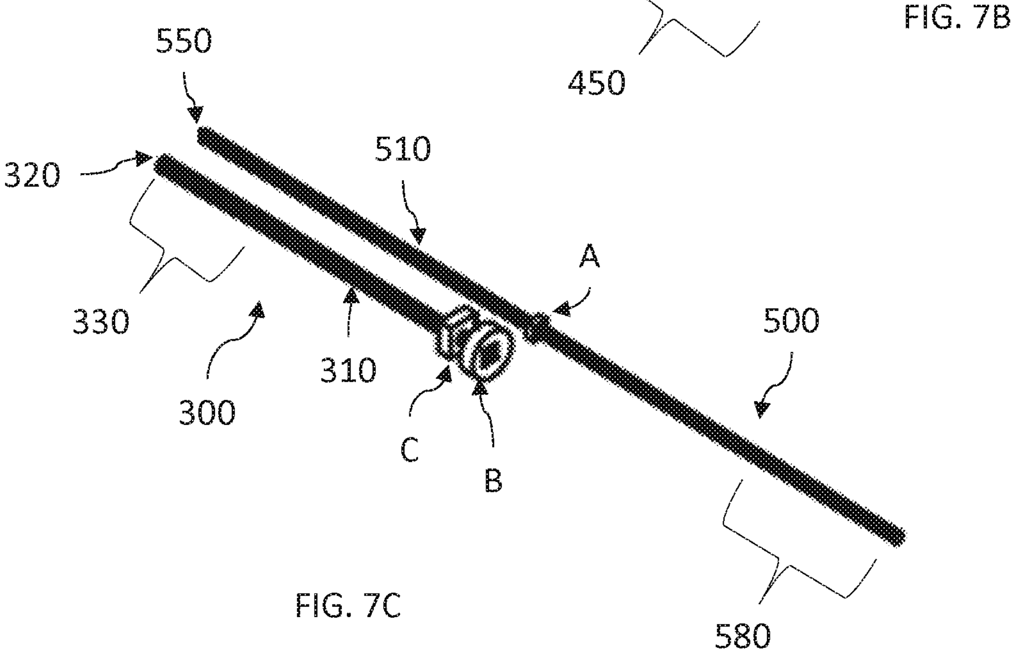
FIG. 7C is a non-limiting perspective view of a cutting element and cannula for use with the device of FIG. 2A or FIG. 2B, in accordance with embodiments of the present disclosure.

In some embodiments, the cannula 300 has an elongated and hollow body 310—the elongated body 310 has an internal wall defining a cannula lumen, which extends along at least a portion of the elongated body 310, as shown in FIG. 7C.

Figure 7D:
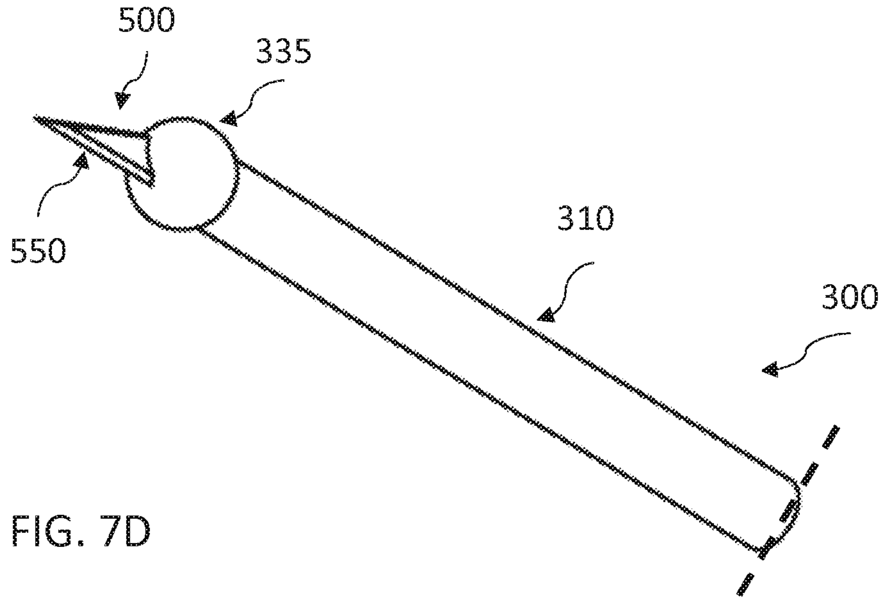
FIG. 7D is a non-limiting perspective view of a cutting element and stabilizing element for use with the device of FIG. 2A or FIG. 2B, in accordance with embodiments of the present disclosure.

In some embodiments, the cannula 300 has a distal interface end 320 defining an aperture and configured to contact a tissue structure for performing the herein described incision, as will be discussed later in this text, thereby limiting the depth of penetration of a distal cutting element and assisting in the precise placement of the device. The cannula 300 defines a lumen extending therethrough in fluid communication with the aperture at the distal interface end 320. The geometry of the distal interface end 320 may vary depending on the specific application. In some embodiments, the distal interface end 320 can include a blunt geometry that defines a distal aperture 325, as illustrated in FIG. 7C. In other embodiments, as shown in FIG. 7D, the distal interface end 320 may incorporate a spherical or bulbous terminal structure located at the distal extremity of the cannula 300. This bulbous structure 335 is dimensioned and contoured to stabilize the cannula against the eye surface during use, particularly during incision or dissection of ocular tissue, such as trabecular meshwork.

The bulbous structure 335 provides several functional advantages. First, it serves as a physical stop that prevents excessive advancement of the distal cutting blade 550 into the tissue, thereby reducing the risk of over-penetration into deeper ocular structures. This enables the user to make consistent incisions at a controlled depth without needing to rely on visual depth cues or apply varying manual force. Second, the bulbous geometry provides a stable contact point against the curved surface of the eye, improving control and alignment of the device during actuation of the blade. This facilitates precise, reproducible dissection of targeted tissues, such as the trabecular meshwork, while minimizing collateral tissue damage. As further illustrated in FIG. 7E, the blade 550 can project from a defined portion of the bulbous structure. The overall design of the bulbous interface end thus enhances both the safety and efficacy of the surgical procedure by simplifying handling and reducing the cognitive and tactile demands on the user.

In some embodiments, the cannula 300 extends along the longitudinal axis Q, and is thus coaxial with the piercing member 400.

In some embodiments, the cannula 300 is configured to be housed in a stowed configuration. For example, at least a proximal portion of the elongated body 310 can be housed within a receiving cavity 630 of the distal segment 60, shown in FIG. 3. In such configuration, the cannula 300 is not observable to the user. At this point, the device 200, 200' is referred to as being in a "first position".

In some embodiments, the cannula 300 is configured to move in a reciprocal fashion within the piercing member 400 such as to move from the stowed configuration to a deployed configuration, and back to the stowed configuration.

In some embodiments, the device 200, 200' is configured to deploy the cannula 300 by extending or causing it to protrude outwardly from the piercing member 400. This deployment mechanism allows for controlled and precise advancement of the cannula 300 relative to the piercing member 400, and may be actuated mechanically, pneumatically, or through another suitable means integrated into the device 200, 200'.

During use, after the piercing member 400 has been advanced to a desired depth through a tissue layer (e.g., sclera), effectively creating an initial access pathway, the device 200, 200' actuates to move the cannula 300 axially outward from the stowed configuration. This axial movement is performed while the distal segment 60 of the device remains stationary with respect to the tissue layer, thereby anchoring the device and providing stability during cannula advancement. As a result of this relative movement, the cannula 300 transitions from the stowed configuration to a deployed configuration, wherein at least a distal segment 330 of the cannula 300 extends beyond the distal-most end or piercing tip 70 of the piercing member 400. In this deployed or extended state, the device 200, 200' is said to be in a "second position," which may correspond to a locked or operational configuration suitable for the insertion of a blade (discussed elsewhere in this text). The controlled extension of the cannula 300 ensures that it reaches the targeted anatomical location while minimizing additional trauma to surrounding tissue, as the cannula 300 follows the path already created by the piercing member 400.

In some embodiments, the cannula 300 can be distally extended as such by actuating a control point when the piercing member 400 has reached a desired depth into the tissue layer from an axial displacement of the device 200, 200'. This is further discussed elsewhere in this text.

In some embodiments, the device 200, 200' is further configured to retract the cannula 300 from the deployed configuration back toward the distal segment 60 (or a component thereof), thereby returning the cannula 300 to its original stowed configuration. This retraction sequence is generally the reverse of the deployment sequence described above and involves translating the cannula 300 in a direction opposite to that used during its initial extension away from the piercing member 400. The retraction may be initiated and controlled by a user-operated actuator or control mechanism, which may be the same as or distinct from the mechanism used to deploy the cannula 300. In some embodiments, the device 200, 200' may include a dual-function control point that toggles between extension and retraction modes, or separate dedicated controls for each motion. Upon activation, the retraction mechanism displaces the cannula 300 proximally, drawing it back through the distal tip 70 and repositioning at least the proximal portion thereof within the internal cavity of the distal segment 60. This ability to selectively retract the cannula 300 enhances safety and device reusability, particularly by shielding the distal segment 330 of the cannula 300 after use or between deployment cycles. Additionally, the retraction mechanism may incorporate detents, locks, or biasing elements (e.g., springs) to assist with precise positioning and to prevent unintended movement of the cannula during handling or operation. In certain embodiments, retraction may occur automatically upon completion of a procedure or removal of the device from the tissue, offering further safety and convenience.

The reader will recognize that advantageously, the deployed and stowed configurations are along the same axis, preferably along longitudinal axis Q of distal segment 60.

In some embodiments, the cannula 300 can be made from any medical-grade material, such as for example medical-grade flexible polymer or silicone, or medical-grade metal such as medical-grade tungsten, titanium, stainless steel, copper, cobalt chrome, aluminum, magnesium, or any alloys thereof; medical grade plastic, and the like.

In some embodiments, the cannula 300 may have a dimension, for example an outer diameter which is sufficiently small to be able to perform reciprocal movement within the lumen of the piercing member 400.

First and Second Implementations—Blade

In some embodiments, the device 200, 200' is further equipped with a blade 500.

In some embodiments, the blade 500 includes a shaft 510 having a distal cutting end 550 and a proximal end 580, as shown in FIG. 7C.

In other embodiments, the blade 500 includes the distal cutting end 550 and may be molded, bonded, welded, or otherwise securely attached to the cannula 300 distal segment 330, as shown in FIG. 7D.

The distal cutting end 550 is operative to cut or ablate a strip of tissue from the eye tissue structure (e.g., trabecular meshwork) as the blade 500 progresses along the surface thereof.

Figure 7E:
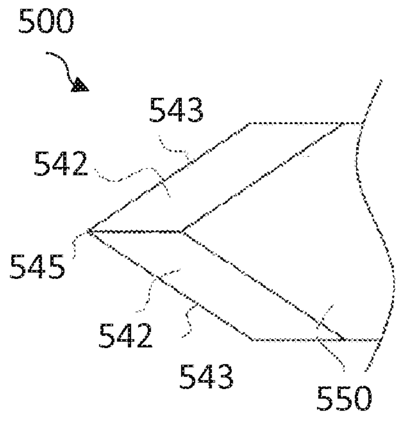
FIG. 7E is a non-limiting perspective view of a distal cutting end from a cutting element, in accordance with embodiments of the present disclosure.

In some embodiments, the distal cutting end 550 may have a pointed V-shaped front end, and slanted surfaces 542 formed on two sides constituting the front end V shape, as shown in FIG. 7D and FIG. 7E. Edges of the slanted surfaces 542 are edges 543. A blade tip 545 is at the intersecting point of the edges 543. In other words, the blade 500 can include laterally slanted surfaces 542 and edges 543 disposed on opposing lateral sides thereof, and have triangle geometry such as an isosceles, equilateral or acute triangle shape. This configuration enables the distal cutting end 550 to perform cutting actions in both lateral directions.

When the device 200, 200' includes the blade 500 as a separate element from the cannula 300 as shown in FIG. 7C, the blade 500 is configured for reciprocal movement within the lumen of cannula 300 and the shaft 510 extends along the longitudinal axis Q, and is thus coaxial with the piercing member 400 and the cannula 300.

In some embodiments, the blade 500 is configured to have at least a portion thereof which is housed within the internal cavity of the distal segment 60, in a stowed configuration. In such configurations, the blade 500 is not observable to the user.

In some embodiments, when the blade 500 is a separate element from the cannula 300, the blade 500 is configured to have at least a portion thereof which is housed within the lumen of cannula 300 and at least a portion thereof within the internal cavity of the distal segment 60, in the stowed configuration.

In some embodiments, the device 200, 200' is further configured to extend the blade 500 away from a distal cutting end of the distal segment 60, in a deployed configuration. In other words, the blade 500 is configured to move in a reciprocal movement within the lumen of the piercing member 400 and/or the cannula 300 (when the blade 500 is a separate element from the cannula 300) such as to move to the deployed configuration, where at least the distal cutting end 550 extends such as to be visible to the user. At this point, the device 200, 200' is referred to as being in a "third position". For example, when the blade 500 is a separate element from the cannula 300, at least the distal cutting end 550 extends beyond the distal cutting end 320 of the cannula 300.

In some embodiments, the extension of the blade 500 can be performed by actuating the same control point discussed previously or a different one. For example, this distal extension can be performed over the longitudinal axis Q.

As discussed elsewhere in this text, the reader will understand that the cannula 300 can operate as an anchor for the blade 500 at the tissue structure interface with the interface surface, ensuring an accurate penetration depth as well as prevent unintended lateral movement during incision. For example, at the trabecular meshwork interface.

In use, upon the above distal extension of the blade 500, the distal cutting end 550 is advantageously exposed and extends distally in a longitudinal direction, away from the distal interface end 320 of the cannula 300. The distance which the distal cutting end 550 extends away is at least the thickness of the eye tissue structure (e.g., trabecular meshwork, which has a thickness of approximately 200-300 microns) so that when the blade 500 is moved across the eye and the blade 500 is pressed against the eye tissue structure (e.g., trabecular meshwork), the distal cutting end 550 comes in contact with the eye tissue structure (e.g., trabecular meshwork) while the incision depth is limited by the interface end 320 of the cannula 300, and an incision results. In some embodiments, the incision can have a depth of at least the eye tissue structure (e.g., trabecular meshwork) thickness so that penetration into the underlying eye structure (e.g., anterior chamber) occurs. In other words, exposure outside of the distal cutting end 550 allows the distal cutting end 550 to perform an incision as the blade 500 progresses along the surface of the eye tissue structure (e.g., trabecular meshwork). The reader will readily understand that when the device 200, 200' does not include a blunt geometry at the distal interface end 320 of the cannula 300, then the distal cutting end 550 is exposed and extends distally in a longitudinal direction, away from the distal tip 70 of the piercing member 400 with similar distance.

In some embodiments, the distance by which the distal cutting end 550 extends beyond the distal interface end 320 can be any distance in the range of from about 50 microns to about 250 microns, including any ranges or values therein. For instance, the distance may be about 50 microns, about 60 microns, about 70 microns, about 80 microns, about 90 microns, about 100 microns, about 110 microns, about 120 microns, about 130 microns, about 140 microns, about 150 microns, about 160 microns, about 170 microns, about 180 microns, about 190 microns, about 200 microns, about 210 microns, about 220 microns, about 230 microns, about 240 microns, or about 250 microns. Preferably, the distance is about 180 microns.

In some embodiments, the blade extension length relative to the tissue reference surface (e.g., the distal interface end) is dimensioned in the range of 200-350 μm, corresponding to a thickness of trabecular meshwork and a position of Schlemm's canal. This blade extension length is configured to span substantially the full thickness of trabecular meshwork while limiting penetration beyond the outer wall of Schlemm's canal, thereby enabling effective incision or excision of trabecular meshwork tissue without risk of damage to deeper ocular structures.

In some embodiments, the shaft 510 may have a dimension, for example an outer diameter which is sufficiently small to be able to perform the reciprocal movement within the lumen of the piercing member 400 and/or cannula 300.

In some embodiments, the blade 500 may be made either of metal, plastic or ceramic, may be coated with biocompatible materials, and may comprise various shapes, dimensions, angulation, degree of sharpness and curvature. The cutting edge of the distal cutting end 550 can be made out of any suitable material that has been used to prepare cutting edges, which can be the same as the rest of the blade 500 or can be a material such as diamond, tungsten carbide, sapphire, and the like.

First and Second Implementations—Actuation Assembly

In a broad embodiment, the device 200, 200' includes an actuation assembly configured to actuate moving parts thereof (e.g., the cannula 300 and/or the blade 500). While the following text describes a particular implementation of an actuation assembly with reference to the figures, the reader will nevertheless understand that variations may be used to achieve a similar result.

Figure 6:
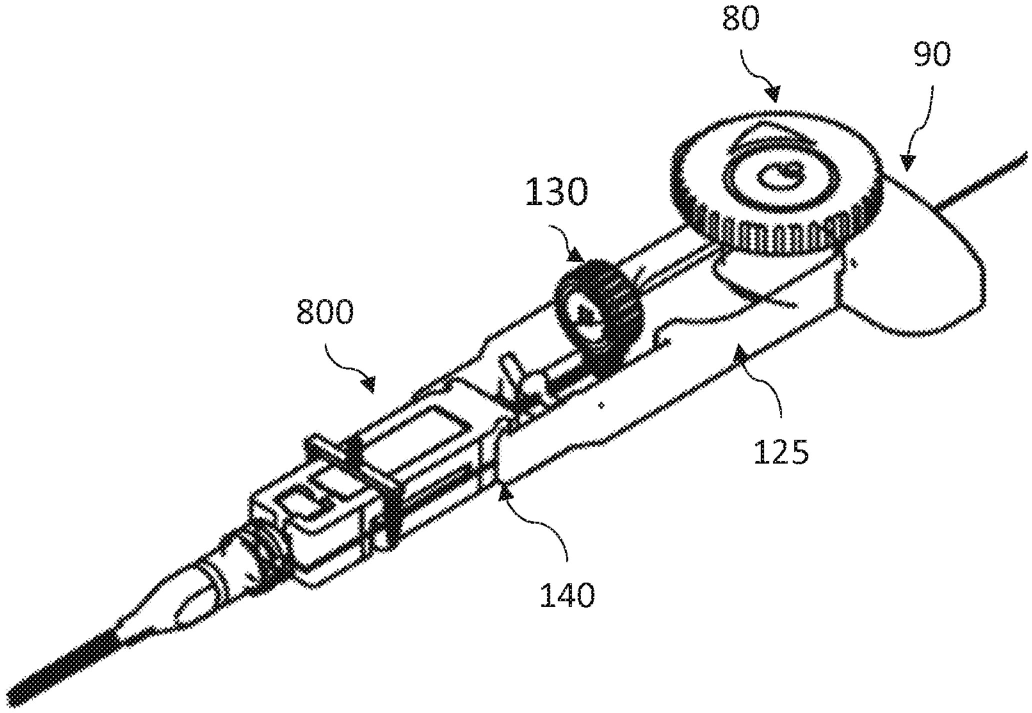
FIG. 6 shows a non-limiting perspective view of components of the actuation assembly for use with the device of FIG. 2A or FIG. 2B, in accordance with embodiments of the present disclosure.

FIG. 6 illustrates a non-limiting practical implementation of an actuation assembly, which includes suitable component or combination of components capable of providing the functionality described herein.

Figure 8:
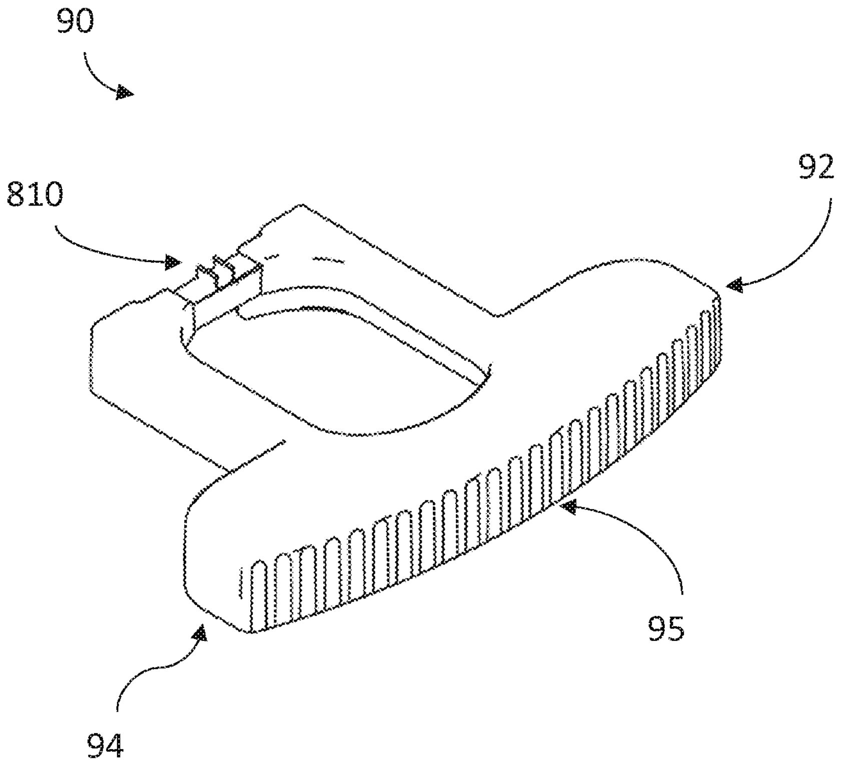
FIG. 8 is a non-limiting perspective view of a portion of a first actuator of the actuation assembly of FIG. 6 (without projections for ease of imaging), in accordance with embodiments of the present disclosure.

In some embodiments, the actuation assembly includes a first control point, which can be engaged by the user to actuate the cannula 300 and/or the blade 500 in a longitudinal direction. In some embodiments, the first control point can take the form of first actuator 90, a portion of which is also shown in FIG. 8. In some embodiments, the first actuator 90 can be conveniently located on the outer housing of the distal segment 60. In some embodiments, the first actuator 90 can be located at a proximal portion of the distal segment 60 for ease of access with a finger.

Figure 5:
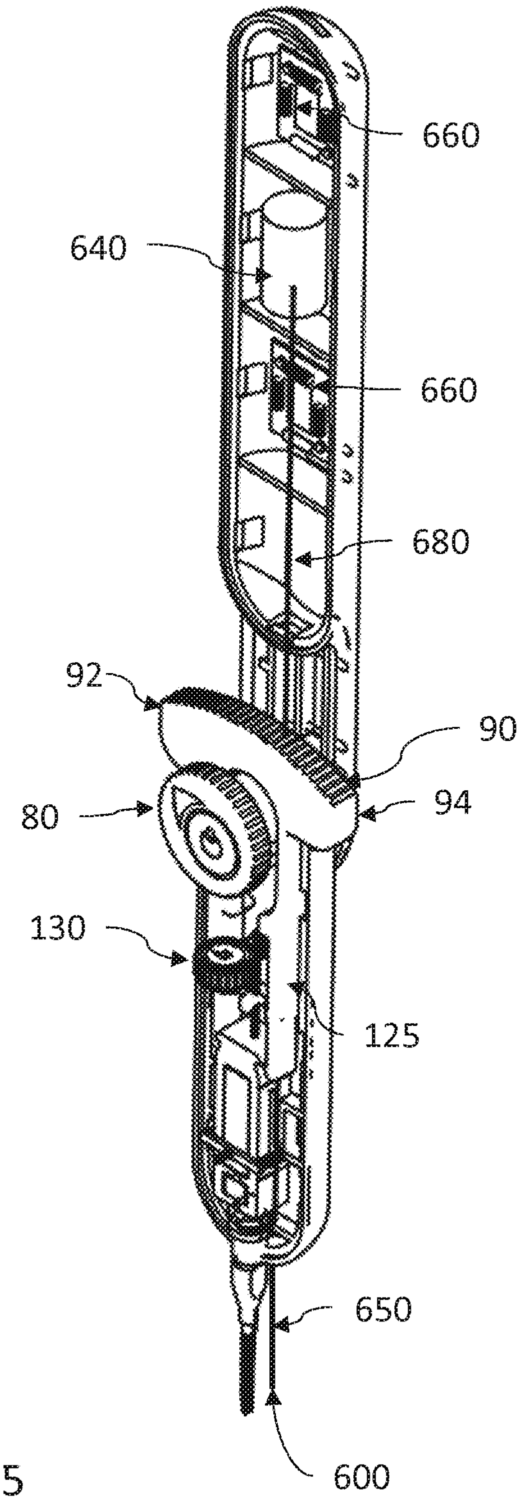
FIG. 5 shows a non-limiting perspective view of the device of FIG. 2A without the top portion of each of the distal and proximal segments, showing internal components of the device, in accordance with embodiments of the present disclosure.

Conveniently, the first actuator 90 can be shaped to facilitate ambidextrous actuation thereof. In some embodiments, the first actuator 90 can have a shape including extensions 92, 94 which each extends away from the distal segment 60, as shown in FIG. 5. In use, the extensions 92, 94 can be conveniently located on each side of the pivot point 85 to facilitate actuation with either the left or right hand holding the proximal segment 65.

In some embodiments, the first actuator 90 may be a slider, trigger, wheel, or any other form that can be easily engaged, preferably with only one finger.

In some embodiments, the first actuator 90 may include teeth 95, or some other form that can provide friction, along an edge thereof to improve the user's ability to confidently engage and release the first actuator 90, even when moisture is present or when the user is wearing gloves. The embodiment illustrated in FIG. 8 includes such teeth 95.

In some embodiments, to improve the safety of using the device 200, the first actuator 90 may include a locking mechanism or a means of preventing the unintended engagement or release of said actuator.

In some embodiments, the first actuator 90 may be made of the same or different material as the distal segment 60.

The actuation assembly further includes a projection 125, which extends towards the distal end of the distal segment 60. In some embodiments, the projection 125 can be configured to operatively couple to the actuator 90 such that actuation of the first actuator 90 from a first position to a second position causes an axial displacement of the projection 125 along the longitudinal axis of the distal segment 60. Such coupling can be permanent or transient.

In some embodiments, the actuator 90 is operatively coupled to the blade 500 to facilitate the reciprocal (e.g., forward and backward or back-and-forth) movement of the blade 500 as previously described. This coupling allows for controlled translation of the blade 500 along the longitudinal axis. As illustrated in FIG. 8, the actuator 90 may include or be operatively associated with a retention element 810, which is configured to engage and secure the body 510. The retention element 810 may include, by way of non-limiting example, a mechanical clamp, a detent mechanism, a spring-loaded latch, or an interference fit feature, any of which may be designed to maintain a fixed spatial relationship between the actuator 90 and the blade body 510 during operation. In such configurations, longitudinal displacement of the actuator 90, whether driven by a motor, pneumatic pressure, hydraulic force, or manual input, results in a corresponding longitudinal displacement of the blade 500. This direct mechanical coupling between the actuator 90 and the blade body 510 ensures synchronized motion, allowing the blade 500 to perform precise linear movements necessary for its intended function. Optionally, the retention element 810 may be releasable or adjustable to permit blade replacement, cleaning, or calibration without decoupling the entire actuator assembly.

As shown in FIG. 3, the distal segment 60 includes an internal surface defining an internal cavity 630 therein. The internal cavity 630 is configured to receive an internal casing 800 shown in FIG. 9A. In some embodiments, the internal casing 800 can be located at a distal portion of the internal cavity 630. The internal casing 800 is configured to receive and operatively couple to the blade 500, for example through apertures 860A, 860B, shown in FIG. 9D.

Figure 9A:
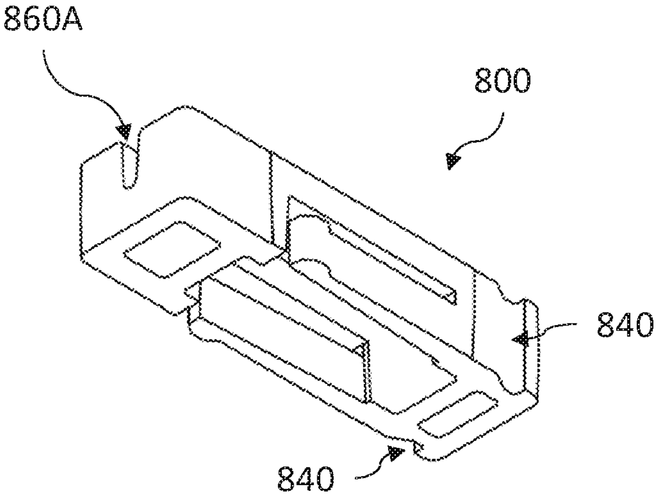
FIG. 9A is a non-limiting bottom perspective view of an internal cassette from the actuation assembly of FIG. 6, in accordance with embodiments of the present disclosure.
Figure 9B:
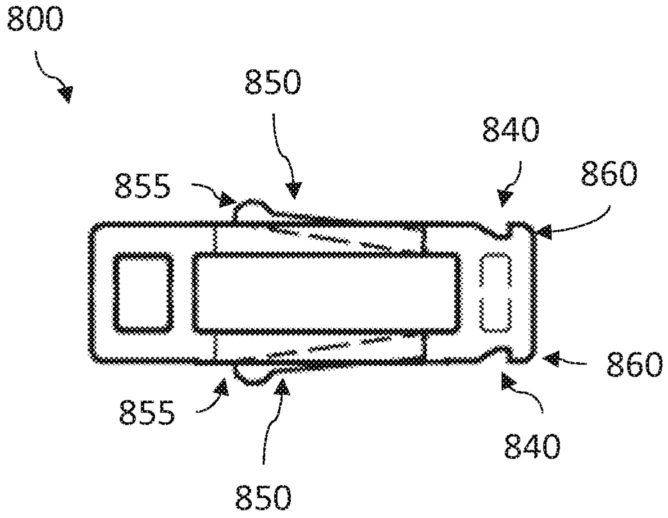
FIG. 9B is a non-limiting top elevated view of the internal cassette of FIG. 9A, in accordance with embodiments of the present disclosure.

As shown in FIG. 9B, the internal casing 800 conveniently includes engaging elements 840 at a proximal portion thereof such that upon pressing the actuator 90, engaging elements 140 located on a distal cutting end of projections 125 engage with complementary engaging elements 840. Engagement of the engaging elements 140, 840 functionally couples the actuator 90 to the internal casing 800, allowing a rigidly coupled movement between the actuator 90 and the internal casing 800. Embodiments that include such features can provide audible feedback to the operator (and others working with the operator), in the form of clicking sounds corresponding to engagement of engaging elements 140, 840.

For example, one of the engaging elements 140, 840 may be a protrusion or pin while the other one of the engaging elements 140, 840 may be a slot configured for engaging with the protrusion or pin. For example, one of the engaging elements 140, 840 may be located on a distal portion of prongs or other types of extending elements connected to the actuator 90, while the other one of the engaging elements 140, 840 may be corresponding depressions located on a proximal portion of the internal casing 800. Of course, many other forms of complementary engaging elements may be devised that functionally couple the actuator 90 to the internal casing 800.

In a non-limiting practical implementation, pressing the actuator 90 effectively moves the engaging elements 140 located on projections 125 extending from actuator 90 towards the internal casing 800. In some embodiments, the actuator 90 and the projections 125 are a single piece component while, in other embodiments, the actuator 90 and the projections 125 are formed by multiple components that are joined together in any suitable manner.

In some embodiments, the projections 125 may be made of a resilient material possessing some flexibility such that upon contacting a superior surface 860 of the internal casing 800, the distal portion of the projections 125 containing engaging elements 140 are slightly pushed out radially to engage with the corresponding depressions of the engaging elements 840 located on the proximal portion of the internal casing 800. Upon engaging with the depressions of the engaging elements 840, the projections 125 being made of a resilient material (e.g., resilient plastic) may thus snap back, compressing the engaging elements 140 against the corresponding engaging elements 840 thus securing the projections 125 to the internal casing 800. Embodiments that include such features can provide audible feedback to the operator (and others working with the operator), in the form of clicking sounds corresponding to the projections 125 snapping back.

Figure 11:
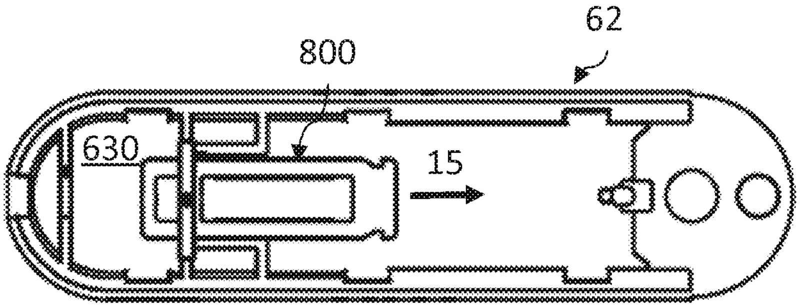
FIG. 11 shows a non-limiting elevated view of the bottom portion of the distal segment of FIG. 10, with the internal cassette being in a free position, in accordance with embodiments of the present disclosure.

In a non-limiting practical implementation, the actuator 90 starts in a first position, where it is disconnected from the internal casing 800. Upon actuation of the first actuator 90, for example when the user presses the first actuator 90 towards a second position, such actuation causes the engaging elements 840, 140 to be engaged one to another such that the actuator 90 engages the internal casing 800 to create a unitary component where further actuation of the first actuator 90 causes the internal casing 800 to axially displace towards the distal cutting end of internal cavity 630. As shown in FIG. 3, the distal segment 60 further includes retaining members 655 associated with an internal surface of the distal segment 60 that are located such as to cooperate with the internal casing 800. The retaining members 655 extend in a direction towards the flexible lateral arms 850 of the internal casing 800, engaging and preventing movement thereof. As depicted in FIG. 9A, the lateral arms 850 can be positioned on or integrated with either side of the internal casing 800. In a rest position, the flexible arms 850 may extend from a proximal portion of the internal casing 800 towards a distal portion thereof, thus allowing the internal casing 800 to slide along the longitudinal axis of the distal segment 60, as shown in FIG. 11. This arrangement also can prevent lateral movement of the internal casing 800.

Figure 12:
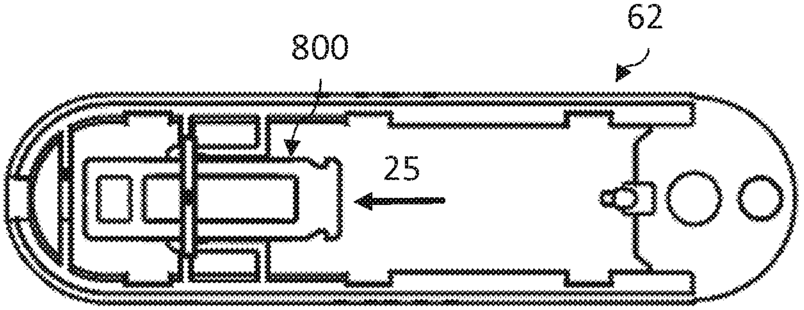
FIG. 12 shows a non-limiting elevated view of FIG. 11, with the internal cassette being in a blocked position, in accordance with embodiments of the present disclosure.

Upon longitudinal movement towards the distal cutting end of distal segment 60, the internal casing 800 moves forward as shown with arrow 25 until a respective distal cutting end 855 of each flexible arms 850 is positioned beyond corresponding and respective distal portion of retaining members 655, as shown in FIG. 12. This arrangement further restrains the internal casing 800 from sliding backwards along the longitudinal axis of the distal segment 60, where such sliding backwards is shown with arrow 15 in FIG. 11. Indeed, in this position shown in FIG. 12, the distal cutting end 855 of the flexible arms 850 engages with or abuts against a corresponding distal portion of retaining members 655. In some embodiments, the distal cutting end 855 of the flexible arms 850 may include a bulge or other suitable structure, which engages with or abuts against the corresponding distal portion of retaining members 655. The flexible arms 850 thus block the returning movement 15.

In some embodiments, the device further comprises a depth control system which may be realized by providing a plurality of indexed mechanical stops, such as engaging element positions on the internal casing 800 or on the projection 125, each mechanical stop corresponding to a different indexed blade depth preset. In some embodiments, the engaging elements 840 may include a series of discrete detent positions spaced along the longitudinal direction of the internal casing 800, each detent position constituting an indexed mechanical stop corresponding to a predetermined axial displacement of the blade 500 and thus a different blade extension distance beyond the distal interface end 320. Alternatively, or additionally, the first actuator 90 may include a graduated travel range with indexed mechanical stops, such that partial actuation of the first actuator 90 to a first indexed mechanical stop produces a first blade extension distance and further actuation to a second indexed mechanical stop produces a second, greater blade extension distance. Such indexed mechanical stops may be accompanied by tactile and/or audible feedback, such as a click or detent engagement, confirming selection of the desired depth preset.

In some embodiments, a third actuator can be functionally coupled with release element 700 which is configured to cooperate with internal casing 800 to allow a return movement thereof.

In some embodiments, the third actuator can be conveniently located at a distal cutting end of the distal segment 60. In some embodiments, the third actuator can be engaged with a user finger.

In some embodiments, the third actuator can be a button, slider, or any other suitable structure element that can be conveniently manipulated by a user, for instance via manual depression or mechanical actuation.

In some embodiments, the third actuator may include a return mechanism, such as a spring loaded mechanism.

Figure 9C:
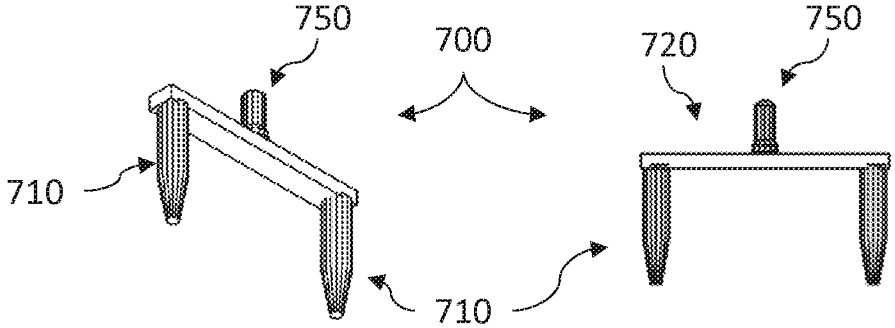
FIG. 9C is a non-limiting bottom perspective view (left) and side view (right) of a release element for use with the internal cassette of FIG. 9A, in accordance with embodiments of the present disclosure.

A specific implementation of the third actuator is shown in FIG. 9C (bottom perspective view on the left and side view on the right).

As shown, the third actuator can include release element 700, which has actuating element 750. In this embodiment, the actuating element 750 is integrally formed with, or operatively coupled to, the release element 700. The actuating element 750 is centrally positioned, vertically extending and is disposed on the upper side of a horizontal platform 720.

The release element 700 further includes a pair of prongs 710, which extend downwardly from the horizontal platform 720. The prongs 710 are spaced apart from one another and oriented substantially parallel to each other along a vertical axis. Each prong tapers to a narrower distal cutting end to facilitate stable engagement with the pair of flexible arms 850.

Figure 9D:
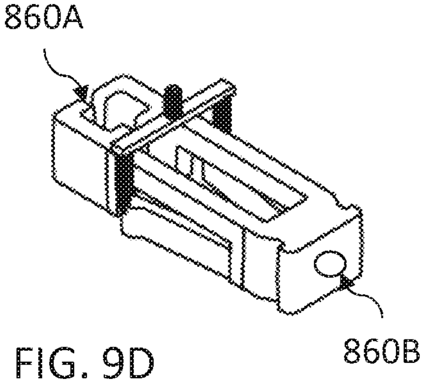
FIG. 9D is a non-limiting top perspective view of the release element of FIG. 9C mounted to the internal cassette of FIG. 9A, in accordance with embodiments of the present disclosure.
Figure 9E:
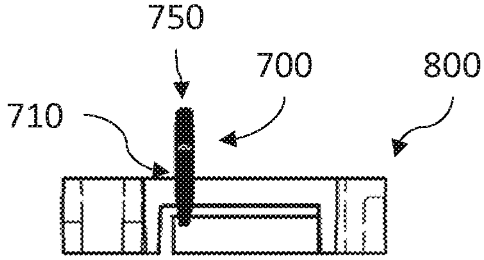
FIG. 9E is a non-limiting side view of FIG. 9D.
Figure 10:
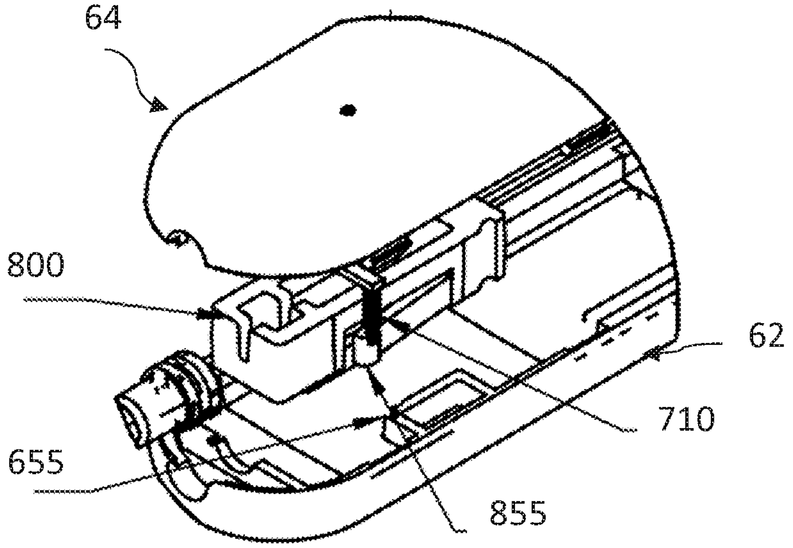
FIG. 10 shows a non-limiting exploded perspective view of a distal cutting end of the distal segment of the device of FIG. 2A or FIG. 2B, with the release element of FIG. 90 mounted to the internal cassette of FIG. 9A, in accordance with embodiments of the present disclosure.

Upon actuation of the element 750, such as through a downward pushing action, the release element 700 is driven in a downward direction such that the prongs 710 engage with the pair of flexible arms 850, as shown in FIG. 9D. The downward motion of the prongs 710 forces the flexible arms 850 to deflect inwardly toward the internal casing 800, due to the tapered configuration of each prong. This inward deflection enables the distal cutting end 855 of the flexible arms 850 to slide over and disengage from the retaining members 655, thereby allowing release or longitudinal movement of the internal casing 800, towards a proximal end of distal segment 60, as shown in FIG. 11 with arrow 15. This configuration enables a secure mechanical release or decoupling of components during a procedural step, such as deployment or retraction.

In some embodiments, this release mechanism is designed to provide audible feedback (such as one or more clicking sounds) that correspond to the incremental movements or final engagement/disengagement of the flexible arms 850. This auditory cue assists the operator in confirming proper actuation of the release mechanism and may also be perceptible to other individuals in the procedural setting, enhancing coordinated workflow and safety assurance.

Figure 13:
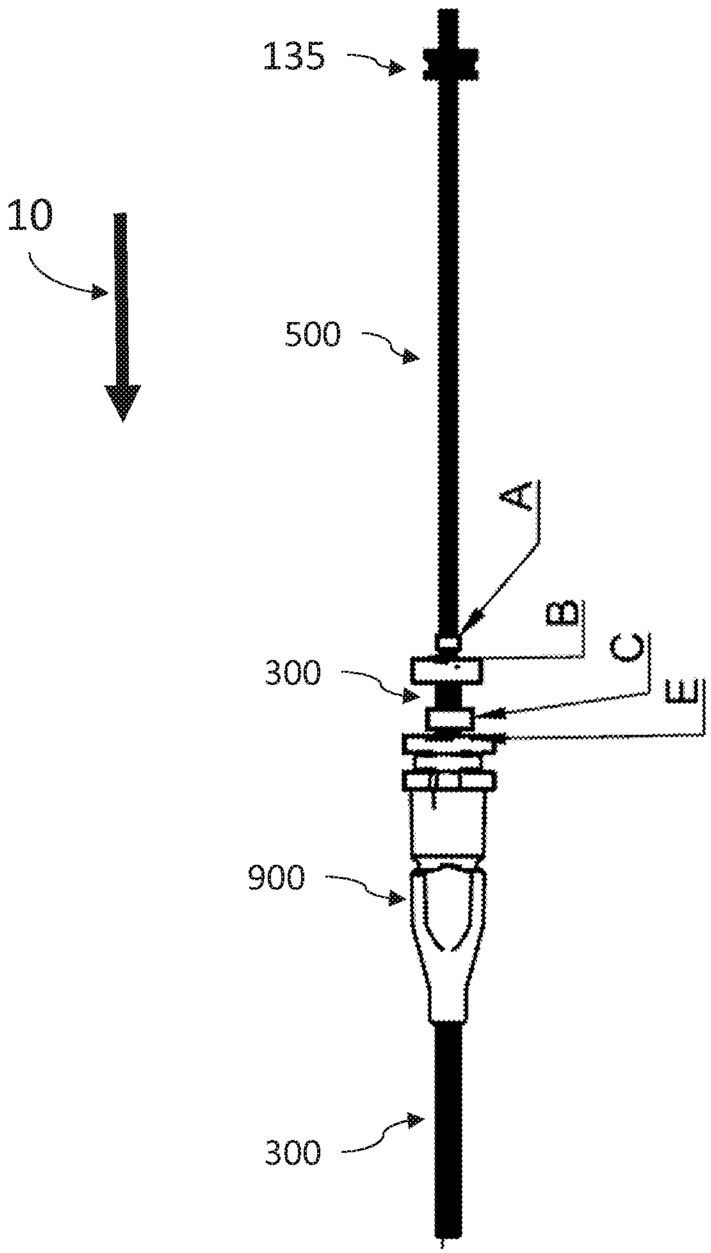
FIG. 13 shows a non-limiting view of components of the rotation assembly, in accordance with embodiments of the present disclosure.
Figure 14:
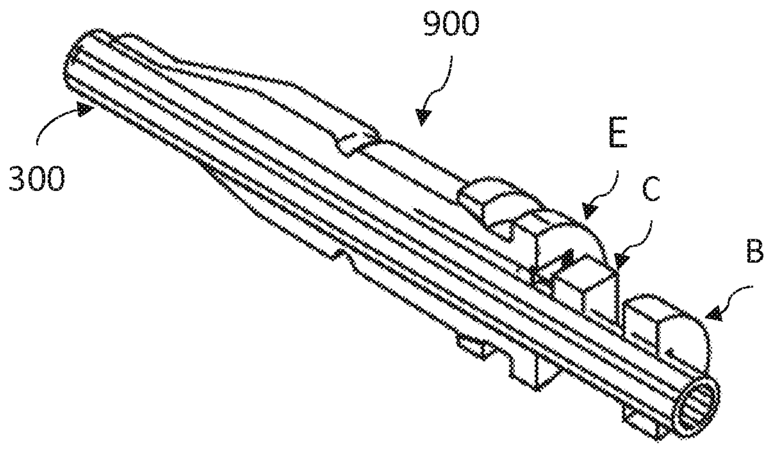
FIG. 14 is a non-limiting perspective cross section view of the hub of FIG. 7A with the cannula of FIG. 7C enclosed in a lumen thereof, in accordance with embodiments of the present disclosure.
Figure 15:
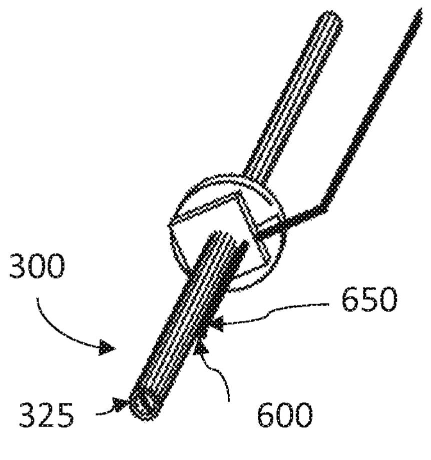
FIG. 15 is a non-limiting elevated perspective view of the cannula of FIG. 7C with an imaging device, in accordance with embodiments of the present disclosure.
Figure 16:
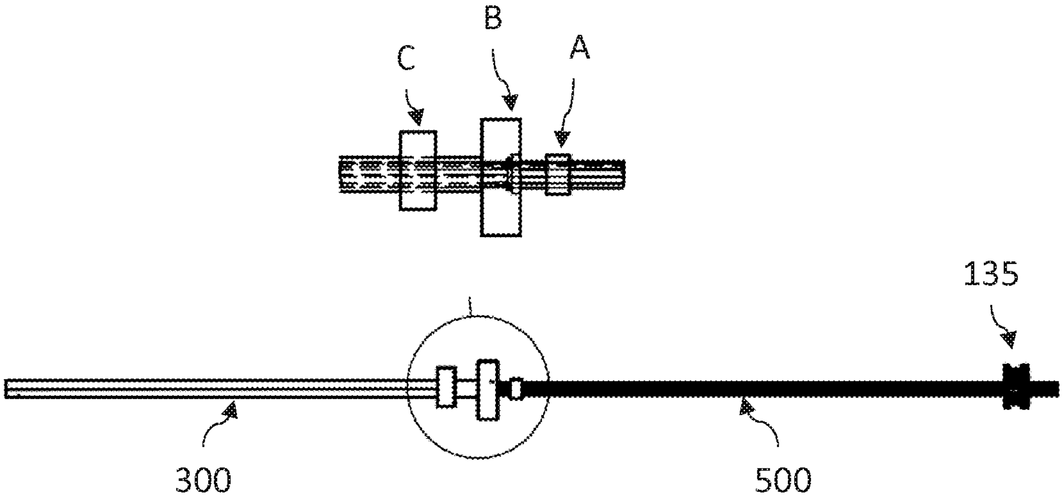
FIG. 16 is a side view of the blade assembled with the cannula in a starting position (e.g., when the blade and the cannula are in the stowed configuration), in accordance with embodiments of the present disclosure.
Figure 17:
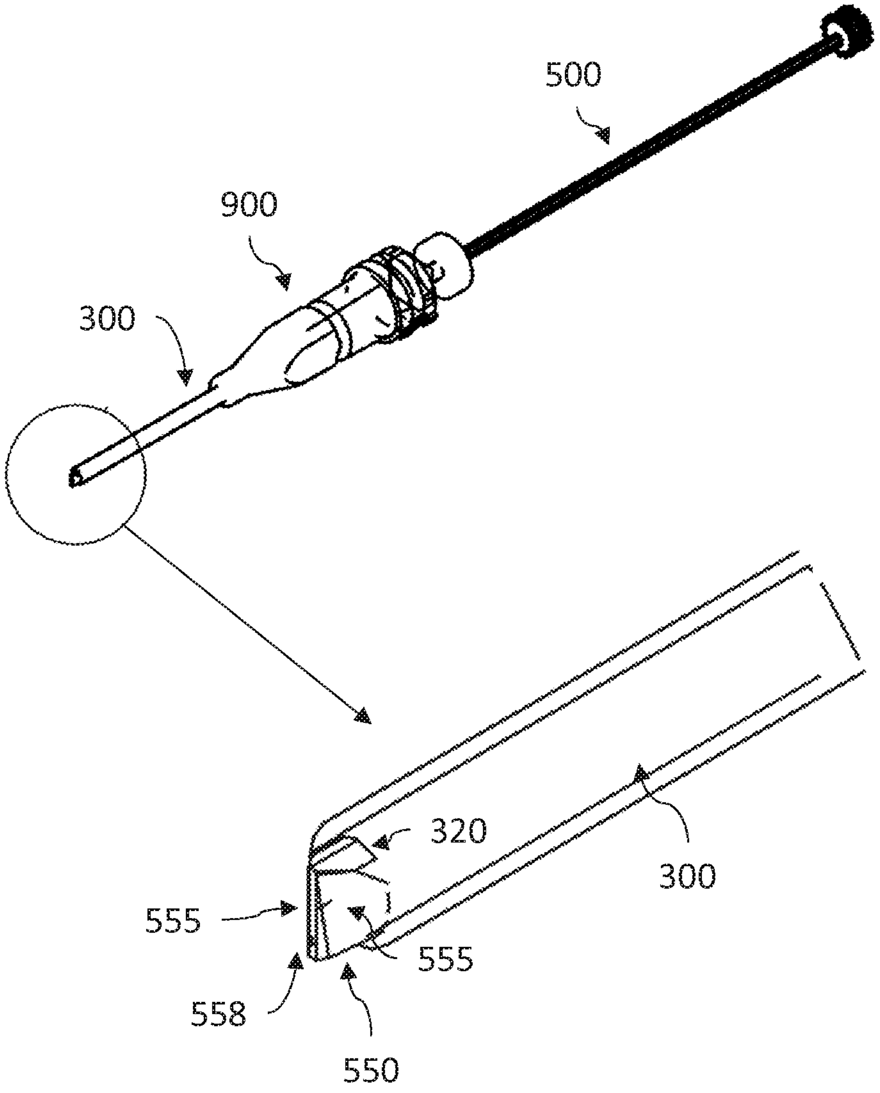
FIG. 17 is a perspective view of the blade in a deployed configuration, where the blade extends away from a distal cutting end of the distal segment, where at least a distal cutting end of the blade extends beyond a distal cutting end of the cannula, in accordance with embodiments of the present disclosure.

Returning to the actuation of the first actuator 90, such actuation also causes the blade 500 to advanced distally (shown with arrow 10 in FIG. 13) through guiding apertures 860A and 860B of internal casing 800, shown in FIG. 9D. Such axial advancement of blade 500 also slides the blade 500 into coaxially aligned cannula 300, until an engagement occurs between engaging element A positioned on body 510 and engaging element B positioned on the cannula 300, as shown in FIG. 7C, FIG. 13 and FIG. 16. In some embodiments, the engaging element B can be positioned close to or at the proximal end of cannula 300. This engagement between engaging element A and engaging element B causes the blade 500 and cannula 300 to become reversibly connected and rigidly coupled through a transition fit, which permits axial alignment and moderate mechanical coupling without requiring deformation or permanent interference.

Continued actuation of the first actuator 90 continues the axial advancement of the connected blade 500 and cannula 300, causing the cannula 300 containing the blade 500 to translate axially into the lumen of the coaxially aligned piercing member 400, resulting in the engagement of engaging element C with engaging element E, which is disposed at the proximal mouth of hub 900. This engagement also comprises a transition fit, providing additional alignment and coupling without mechanical interference. Upon completion of these sequential engagements, the engaging elements A and B, and the engaging elements C and E are respectively locked in positional continuity to form respective rigidly coupled bodies A/B and C/E—rigid, unified mechanical structures capable of transmitting torque and axial force across their constituents. At this point, the device 200, 200' is at the third position discussed previously, where the distal cutting end 550 of blade 500 extends beyond the distal cutting end 320 of cannula 300.

In some embodiments, the actuation assembly includes a reorientation mechanism configured to reorient the blade 500 relative to the device while the blade 500 remains within the lumen of the cannula 300 to allow at least the blade 500 to be displaced along a second incision path distinct from the first incision path.

In some embodiments, the reorientation mechanism includes a second control point, which can be engaged by the user to actuate the cannula 300 and the blade 500 in a rotational direction, and in a rigidly coupled fashion. Upon actuation, the second control point can also actuate the hub 900 and piercing member 400 in the rotational direction, and in rigidly coupled fashion with the cannula 300 and the blade 500 when there is a presence of respective rigidly coupled bodies A/B and C/E.

In alternate embodiments, the device does not include an engaging element E such that only engaging elements A and B form rigidly coupled body A/B-upon actuation of the second control point, there is a controlled rotational motion of the cannula-blade assembly, while the hub 900 and piercing member 400 remain fixed.

In some embodiments, the second control point can take the form of second actuator 130, as shown in FIG. 5 and FIG. 6. In some embodiments, the second actuator 130 can be conveniently located at a proximal portion of the distal segment 60 for ease of access by the user.

In some embodiments, the second actuator 130 may be a slider, trigger, wheel, or any other form that can be easily engaged by the user, preferably with only one finger.

In some embodiments, the second actuator 130 may include teeth, or some other form that is capable of providing friction, along an edge thereof to improve the user's ability to confidently engage and release the second actuator 130, even when moisture is present or when the user is wearing gloves. Furthermore, to improve the safety of using the device 200, the second actuator 130 may include a locking mechanism or a means of preventing the unintended engagement or release of said actuator.

In some embodiments, the second actuator 130 may be made of the same or different material as the first actuator 90.

In some embodiments, the second actuator 130 is in the form of a wheel as best shown in FIG. 6, which is configured to rotate around the longitudinal axis Q.

The second actuator 130, which may be a motorized or manually driven drive gear, is operably coupled to engage with a wheel gear 135 disposed on a proximal end of body 510 of the blade 500, as shown in FIG. 13. Engagement of the second actuator 130 with wheel gear 135 allows rotational input from the second actuator 130 to be transferred to the rigidly coupled engaging elements A/B and C/E (when engaging element E is present). This configuration facilitates controlled rotational motion of the needle-cannula-blade-hub assembly about its longitudinal axis. This rotational capability is particularly advantageous for procedural or mechanical adjustments during ophthalmic procedures, such as when changing the cutting direction on the surface of an eye tissue layer, for example, transitioning from a vertical to a horizontal incision, or vice versa.

In some embodiments, the reorientation mechanism is adapted to reorient the blade 500 relative to the device 200, 200' while the blade 500 remains associated with the piercing member.

In some embodiments, the reorientation mechanism comprises a rotational actuator adapted to rotate the blade 500 about a longitudinal axis of the device 200. For example, to rotate the blade 500 by a predetermined angular displacement between 30 degrees and 90 degrees.

With reference to FIG. 7A, in the depicted embodiment, the hub 900 includes an engaging tab 910 protruding from its external surface. This tab 910 is specifically configured to interact with an interfering structure 920, which is part of a fixed proximal ring 930 positioned circumferentially around the proximal portion of the hub 900. The proximal ring 930 remains stationary relative to the hub's rotation. When the engaging tab 910 rotates into contact with the interfering structure 920, it forms a mechanical stop that impedes further rotation of the hub 900 beyond a predetermined angular limit. This abutment feature ensures that rotational motion is restricted within a defined range, allowing precise control over the angular positioning of the blade 500 during a surgical procedure. For example, in the depicted embodiment, the engaging tab 910 and the interfering structure 920 can be configured to prevent the needle-cannula-blade-hub assembly from rotating more than 90 degrees. Although an engaging tab 910 and interfering structure 920 are described herein, it is noted that any suitable means of control over the angular positioning of the blade 500 can be used, if desired.

In some embodiments, detents, keyed slots, or anti-rotation features may be integrated into one or more of engaging elements A, B, C, and E to enhance torque transmission or prevent slippage under load. Materials and tolerances for the transition fits may be selected to optimize for repeated engagement/disengagement cycles, sterilization compatibility, or desired frictional characteristics.

The reader will readily understand that these aforementioned features of cannula 300, e.g., elements B and C, are also present in the variant where the distal interface end 320 is the spherical or bulbous terminal structure shown in FIG. 7D.

Third Implementation—Device Structure and Configuration

Having described the first and second implementations, which employ a multi-component coaxial assembly comprising a piercing member, cannula, and blade, a third implementation will now be described. The third implementation is distinguished from the first and second implementations in that it omits the piercing member and cannula assembly and instead employs a delivery member that directly houses the blade and integrates a two-stage motion reduction mechanism for fine-resolution depth control. The third implementation is particularly suited for ab interno procedures in which the device is inserted through a pre-existing corneal incision or paracentesis. Features described in connection with the first and second implementations, including the materials, dimensions, and general design principles, may be applied to the third implementation where compatible, and vice versa, unless the context indicates otherwise.

Figure 21:
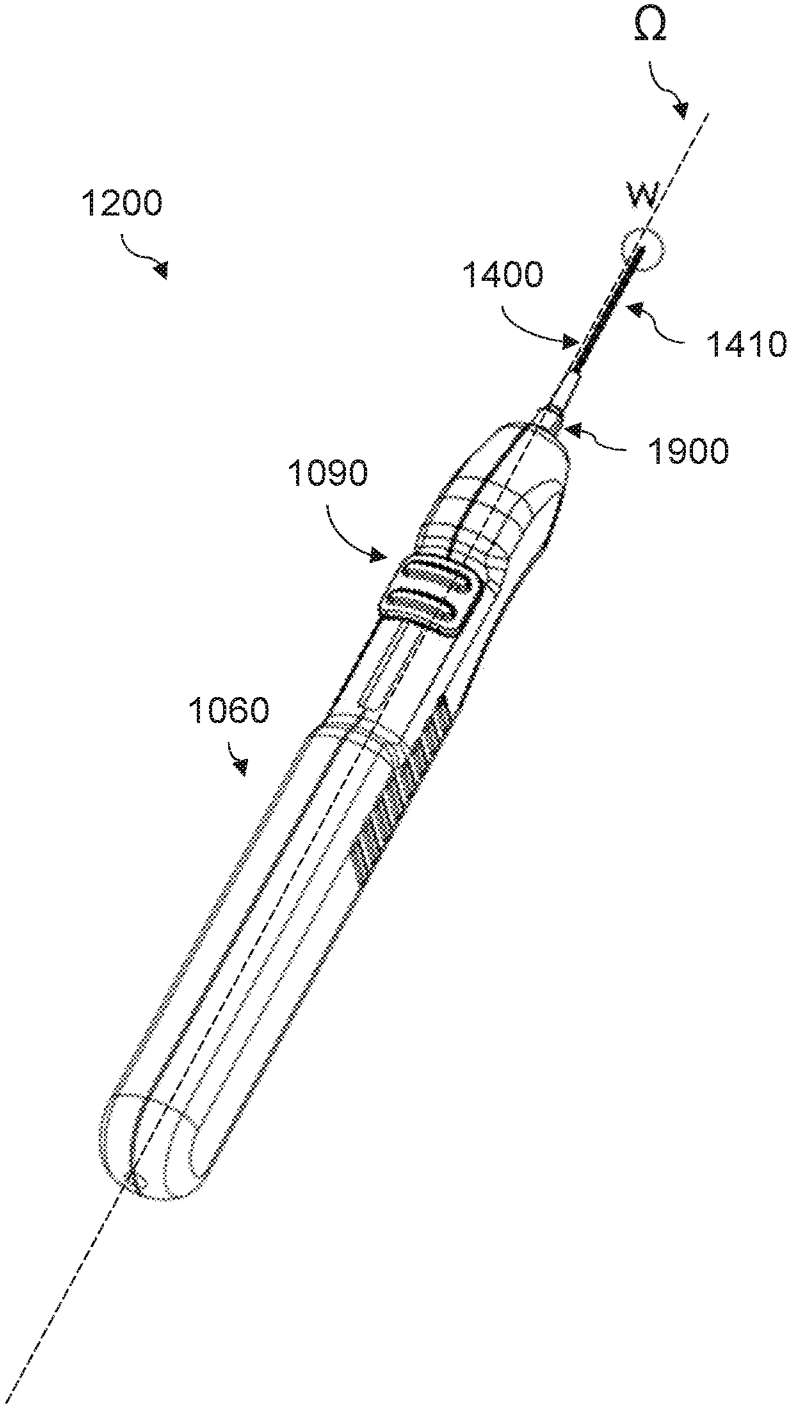
FIG. 21 is a non-limiting perspective view of a device configured to perform ocular incisions in accordance with a third implementation of the present disclosure.

Referring now to FIG. 21, the third non-limiting implementation of a device arranged and configured in accordance with certain features, aspects, and advantages of the present disclosure is illustrated. The illustrated device implementation can be used for performing an incision in an eye structure. In particular, the device can be used to perform an incision in the trabecular meshwork for reducing intraocular pressure, or can be any other type of device that would benefit from any or all of the features, aspects and advantages of the present disclosure.

In some embodiments, device 1200 includes a body 3060 configured for grasping with the user's hand. The body may be ergonomically shaped, contoured, or otherwise dimensioned to facilitate comfortable, stable, and precise handling during use. In some embodiments, the body 3060 may include one or more grip-enhancing features, such as textured surfaces, finger rests, or anti-roll geometries, that promote steady manipulation of the device during microsurgical procedures. The body 3060 may further include or house one or more actuation mechanisms configured to control advancement, retraction, or reciprocation of the blade, as described in further detail below.

Figure 27:
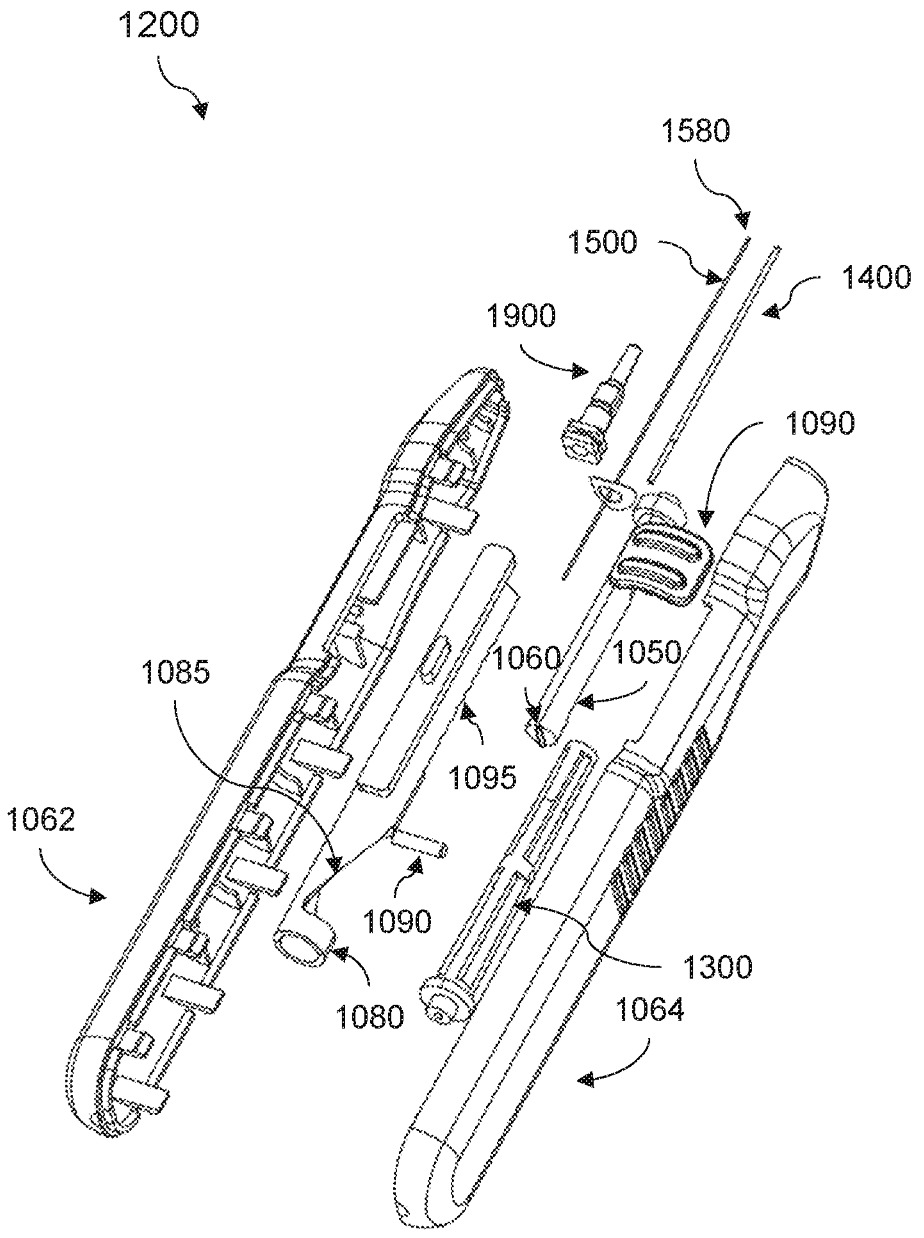
FIG. 27 is a non-limiting perspective view of disassembled housing portions of the device of FIG. 21, in accordance with embodiments of the present disclosure.

In some embodiments, the body 3060 can be formed with first and second housing portions 1062, 1064, as shown in FIG. 27. For example, first and second housing portions 1062, 1064 may be configured to assemble one onto another through suitable coupling means. Examples of suitable means are described in WO 2024/124336, which is incorporated by reference herein.

In some embodiments, the device 1200 is capable of being autoclaved or sterilized in some other manner. In some embodiments, the device may be made from any suitable material, such as, but not limited to, polyethylene (PE) including low-density PE, high-density PE, ultra-high molecular weight PE; polypropylene (PP); polytetrafluoroethylene; thermoplastic polyurethane; polycarbonate; polyphtalic acid; acrylic; acrylonitrile butadiene styrene (ABS); silicon; and the like.

In some embodiments, the device 1200 may have a suitable length, which is convenient for holding and operating with a single hand from the user. In some embodiments, the device 1200 may have a total length L of from about 100 mm to about 300 mm, including any values or ranges therein. For example, a length L of about 120 mm, about 130 mm, about 140 mm, about 150 mm, about 160 mm, about 170 mm, about 180 mm, about 190 mm, about 200 mm, about 210 mm, or about 220 mm. For example, a length L of about 140 mm, about 145 mm, or about 150 mm. For example, a length L of about 145 mm.

In some embodiments, the device 1200 may have a suitable width, which is convenient for holding and operating with a single hand from the user. In some embodiments, the device may have a width of from 6.0 mm to about 9.0 mm, including any values or ranges therein. For example, a width of about 6.5 mm, about 7.0 mm, about 7.5 mm, or about 8.0 mm, preferably a width of about 7.4 mm.

Third Implementation—Delivery Member

In some embodiments, the device 1200 includes a delivery member 1400 having an elongated body 1410 extending along the longitudinal axis Ω and a distal interface end 1420 defining an aperture, the elongated body 1410 defining a lumen extending therethrough in fluid communication with the aperture.

In some embodiments, the delivery member 1400 may comprise a cannula, shaft, tube, sleeve, or similar elongate structure dimensioned for insertion into the anterior chamber of the eye, such as through a corneal incision/paracentesis which can be created with a separate (standard blade) instrument. In some embodiments, the delivery member 1400 extends along the longitudinal axis Ω.

In some embodiments, the delivery member 1400 is sufficiently rigid to maintain its shape during insertion and manipulation within the eye, while in other embodiments the delivery member 1400 may include one or more flexible or articulable portions that facilitate navigation through the anterior chamber angle.

In some embodiments, the delivery member 1400 may be formed from biocompatible materials, including but not limited to stainless steel, titanium, nickel-titanium alloy, polymeric materials, or combinations thereof.

In some embodiments, the delivery member 1400 may have a cross-sectional profile that is round, oval, rectangular, or otherwise shaped to accommodate passage of the blade therethrough while maintaining a low-profile geometry suitable for minimally invasive insertion.

In some embodiments, the delivery member 1400 has a distal interface end 1420 defining an aperture and configured to contact a tissue surface and serve as a stabilizing reference point during cutting. The lumen of the delivery member 1400 is in fluid communication with the aperture at the distal interface end 1420, such that the blade 1500 may extend through the lumen and the aperture to engage the target tissue. For example, the distal interface end 1420 is configured to contact ocular tissue surface, e.g., sclera or limbus, and establish a stable, repeatable anatomical zero point. The distal interface end 1420 operates as a mechanical stop that limits the depth of blade penetration and assists in precise placement of the device 1200 relative to the target tissue.

Third Implementation—Blade and Cutting Geometry

Figure 22:
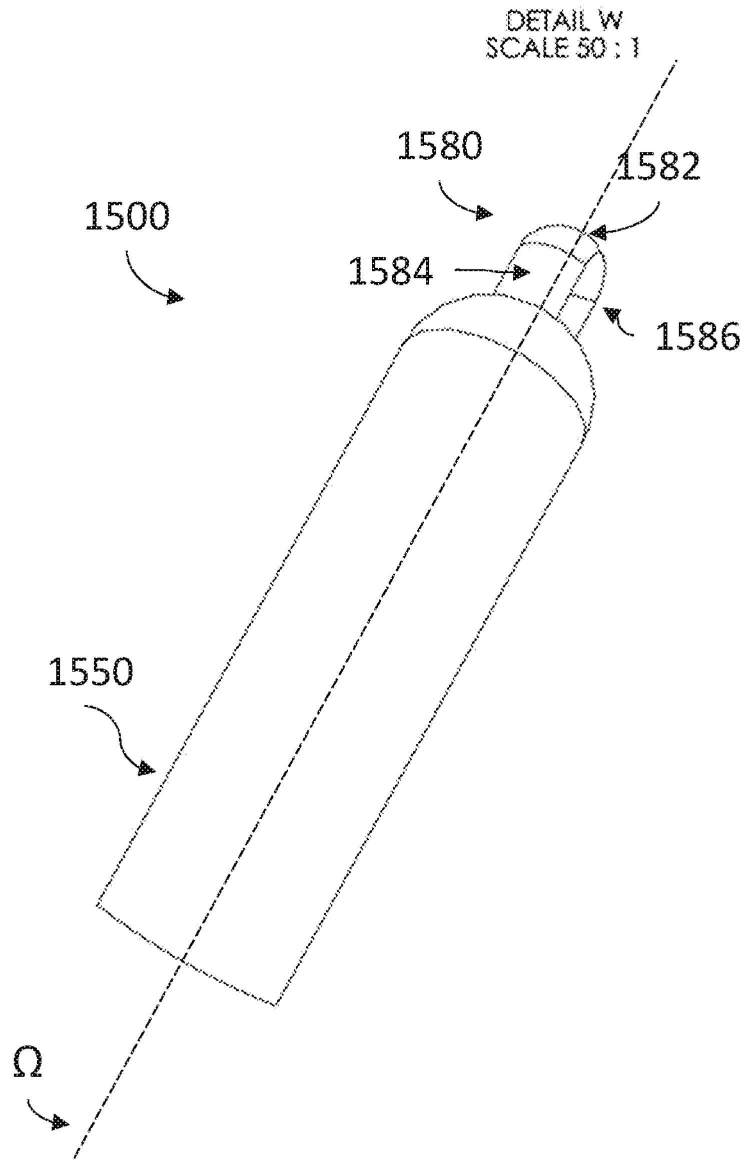
FIG. 22 is a non-limiting perspective view of a blade for use with the device of FIG. 21, showing the blade body and distal cutting end with cutting edges, in accordance with embodiments of the present disclosure.

Referring now to FIG. 22, in some embodiments, the device 1200 includes a blade 1500 having a blade body 1550 extending over the longitudinal axis Ω and terminating at a distal cutting end 1580.

In some embodiments, the blade body 1550 may be formed from surgical-grade stainless steel, ceramic, diamond, or other materials suitable for ophthalmic surgical cutting applications.

In some embodiments, the blade body 1550 has a thickness, width, and length dimensioned to slidably fit within the lumen of the delivery member 1400 while permitting smooth movement therein. The blade 1500 is movable relative to the delivery member 1400 along the longitudinal axis Ω between a retracted position (also referred to as a stowed configuration), in which the blade 1500 is at least partially contained within the lumen of the delivery member 1400 and the distal cutting end 1580 is proximal to the distal interface end 1420, and an extended position (also referred to as a deployed configuration), in which the distal cutting end 1580 extends beyond the distal interface end 1420 and is distal to the distal interface end 1420. In the retracted position, the blade 1500 is substantially or entirely enclosed within the delivery member 1400, thereby protecting surrounding ocular tissues from contact with the cutting end 1580 during insertion, positioning, and withdrawal of the device 1200. In the extended position, the distal cutting end 1580 is exposed and available to engage and cut targeted tissue.

In some embodiments, the blade has a width which is derived from SC meridional biometry: 196-239 μm across disease states. In some embodiments, the blade can have a width of about 300 μm, which overhangs the canal edge by about 30 μm per side, thus advantageously providing a geometric tolerance for gonioscopic angulation without over-excising trabecular meshwork tissue.

In some embodiments, as shown in FIG. 22, the distal cutting end 1580 of the blade 1500 comprises a curved, rounded, or arcuate distal apex 1582 and laterally extending cutting edges 1584, 1586 disposed on opposing lateral sides of the blade body 1550, the cutting edges 1584, 1586 diverging from the distal apex 1582 in a substantially symmetrical arrangement. This distal cutting end geometry is configured to enable bidirectional scraping or cutting of the trabecular meshwork in opposing circumferential directions. The curved distal apex 1582 transitions smoothly into the laterally extending cutting edges 1584, 1586 without forming a sharp angular point, such that the distal extremity of the blade presents a non-penetrating, blunted distal surface along the longitudinal axis Ω while maintaining sharpened lateral cutting edges on opposing sides thereof. This geometry forms a generally spatulate, ogival, or rounded-spade profile when viewed from above. The curved or rounded apex geometry is functionally significant: because the device is configured for lateral scraping or incising of the trabecular meshwork rather than longitudinal puncture thereof, the non-penetrating curved apex prevents unintended longitudinal penetration into or through the trabecular meshwork, Schlemm's canal, or deeper ocular structures when the blade is advanced to an extended position. Instead, the curved apex distributes contact force over a broader distal surface area, promoting controlled lateral engagement with the target tissue. This configuration provides a compact yet highly functional cutting geometry that is optimized for engaging and incising the fibrous, porous tissue of the trabecular meshwork in both circumferential directions without requiring withdrawal, rotation, or repositioning of the device.

In some embodiments, the distal cutting end 1580 comprises a distal apex 1582 positioned at the foremost point of the blade 1500 along the longitudinal axis Q, as illustrated in FIG. 22. The distal apex 1582 has a curved, rounded, or arcuate profile such that the foremost extremity of the blade presents a smoothly contoured, non-penetrating surface when viewed in plan. Extending laterally and proximally from the distal apex 1582 are a first cutting edge 1584 and a second cutting edge 1586, each disposed on an opposing lateral side of the blade body 1550. The first and second cutting edges 1584, 1586 are configured as sharpened margins that extend from the curved distal apex 1582, diverging laterally and proximally along the blade body 1550. The transition between the curved distal apex 1582 and each cutting edge 1584, 1586 is smooth and continuous, without an abrupt angular junction. In some embodiments, the first and second cutting edges 1584, 1586 are substantially mirror-symmetric relative to a central plane containing the longitudinal axis Q, such that the distal cutting end 1580 exhibits bilateral symmetry. This symmetrical configuration ensures that the cutting performance of the blade 1500 is substantially equivalent in both lateral directions, thereby enabling uniform bidirectional incision of the trabecular meshwork.

In some embodiments, the first cutting edge 1584 and the second cutting edge 1586 each have a length measured from the distal apex 1582 to a transition point where the cutting edge meets the main blade body 1550. The cutting edge length may be selected based on the desired incision depth and the anatomical dimensions of the trabecular meshwork. For example, each cutting edge may have a length in the range of about 50 microns to about 500 microns, including any values or subranges therein. In some embodiments, each cutting edge has a length of about 100 microns to about 300 microns. The cutting edges 1584, 1586 may be formed with a sharpened bevel having a bevel angle in the range of about 10 degrees to about 45 degrees relative to the upper or lower surface of the blade body 1550. The bevel may be a single-bevel configuration (ground on one side only) or a double-bevel configuration (ground symmetrically on both upper and lower surfaces). In some embodiments, a double-bevel configuration is preferred for bidirectional cutting applications, as it provides substantially equal cutting performance regardless of the direction of blade travel.

In some embodiments, the distal cutting end 1580 is configured for bidirectional scraping or cutting action while maintaining continuous engagement with the target tissue. The first cutting edge 1584 and the second cutting edge 1586 extend laterally on opposing sides of the blade body 1550, such that the aperture defined between the two cutting edges is oriented substantially transverse to the direction of lateral blade travel. When the blade 1500 is displaced laterally in a first direction (e.g., nasally), both the first cutting edge 1584 and the second cutting edge 1586 simultaneously engage the trabecular meshwork tissue along their respective lengths. Because the cutting edges are oriented transverse to the direction of lateral displacement, both edges cut or scrape the tissue equivalently as the blade travels across the trabecular meshwork. When the blade 1500 is subsequently displaced laterally in a second, opposing direction (e.g., temporally), both cutting edges again simultaneously engage the tissue in the same transverse orientation. This transverse cutting edge orientation enables the distal cutting end 1580 to scrape or cut the trabecular meshwork tissue in both lateral directions without requiring withdrawal, rotation, or repositioning of the device 1200 and while maintaining continuous engagement with the target tissue throughout the bidirectional cutting procedure. In this manner, the surgeon may perform a continuous or sequential incision of the trabecular meshwork in both the nasal and temporal directions from a single, fixed device position without withdrawing the blade 1500 from the anterior chamber angle. The bidirectional cutting capability of the distal cutting end 1580 reduces overall procedure time, minimizes the number of instrument insertions and manipulations within the eye, and decreases the risk of iatrogenic trauma to surrounding ocular structures.

In some embodiments, the distal cutting end 1580 comprises a bilateral cutting edge or cutting geometry configured to incise or excise trabecular meshwork in opposite circumferential directions while maintaining the device in the eye (i.e., without removing the device from the eye). The bilateral cutting geometry, comprising the first cutting edge 1584 and the second cutting edge 1586, enables the surgeon to perform bidirectional incision or excision of trabecular meshwork tissue from a single corneal entry site without requiring device withdrawal, reorientation, or repositioning between cutting passes in each circumferential direction.

In some embodiments, the distal cutting end 1580 is further configured to perform a scraping action in addition to or instead of a clean cutting action. The scraping action may be achieved by configuring the first and second cutting edges 1584, 1586 with a reduced sharpness, a serrated profile, a micro-textured surface, or a rake angle that is optimized for tissue abrasion rather than tissue incision. In some embodiments, the cutting edges 1584, 1586 include micro-serrations or teeth having a pitch in the range of about 10 microns to about 100 microns, which engage and abrade the trabecular meshwork tissue as the blade 1500 is displaced laterally. This scraping configuration may be advantageous in cases where complete excision of the trabecular meshwork strip is desired, as opposed to a simple linear incision. In other embodiments, the cutting edges 1584, 1586 are configured as smooth, sharpened margins optimized for clean incision with minimal tissue disruption.

In some embodiments, the distal cutting end 1580 may be formed integrally with the blade body 1550 as a unitary, monolithic component. In other embodiments, the distal cutting end 1580 may be formed as a separate cutting tip element that is attached, bonded, welded, press-fit, or otherwise secured to the distal end of the blade body 1550. The distal cutting end 1580 may be formed from the same material as the blade body 1550, or from a different material selected for enhanced cutting performance, wear resistance, or biocompatibility. In some embodiments, the distal cutting end 1580 may be formed from surgical-grade stainless steel (e.g., 440 C, 420, or 316L stainless steel), titanium or titanium alloys (e.g., Ti-6Al-4V), cobalt-chromium alloys, ceramic materials (e.g., zirconia, alumina), diamond, sapphire, tungsten carbide, or combinations thereof. In some embodiments, the distal cutting end 1580 is coated with a biocompatible coating, such as titanium nitride, diamond-like carbon (DLC), parylene, or a hydrophilic polymer coating, to enhance lubricity, reduce friction, or improve tissue compatibility.

In some embodiments, the distal cutting end 1580 is dimensioned to correspond to the anatomical dimensions of the trabecular meshwork and Schlemm's canal. The trabecular meshwork typically has a thickness in the range of about 80 microns to about 120 microns in adult patients, and Schlemm's canal has a meridional width in the range of about 196 microns to about 239 microns across various disease states. Accordingly, the distal cutting end 1580 may have a maximum width (measured perpendicular to the longitudinal axis Ω at the widest point of the cutting edges) in the range of about 200 microns to about 400 microns, including any values or subranges therein. In some embodiments, the maximum width may be about 250 microns, about 300 microns, or about 350 microns. In some embodiments, the maximum width is about 300 microns, which provides an overhang of about 30 microns per side relative to the average canal width, thereby accommodating anatomical variability and gonioscopic angulation without over-excising the trabecular meshwork. The distal cutting end 1580 may have a thickness (measured perpendicular to the upper and lower surfaces of the blade) in the range of about 50 microns to about 200 microns.

In some embodiments, the distal cutting end 1580 is configured to cooperate with the depth control system of the device 1200 to provide controlled, reproducible penetration depth during bidirectional cutting of the trabecular meshwork, as shown in FIG. 23 to FIG. 27. When the blade 1500 is advanced to a selected depth preset, the distal cutting end 1580 extends beyond the distal interface end 1420 of the delivery member 1400 by a corresponding predetermined distance. This predetermined distance is selected to ensure that the first and second cutting edges 1584, 1586 of the distal cutting end 1580 are positioned at an appropriate depth within the trabecular meshwork to effect the desired incision or scraping action.

In some embodiments, the indexed depth presets of the depth control system are specifically calibrated to position the distal cutting end 1580 at clinically relevant tissue depths. For example, a first depth preset of about 150 microns may position the distal cutting end 1580 to traverse the trabecular meshwork (approximately 80-100 microns thickness), the juxtacanalicular tissue (approximately 20 microns thickness), and the inner wall of Schlemm's canal, thereby enabling entry into the canal lumen without risk of scleral breach. A second depth preset of about 190 microns may accommodate average adult anatomy with age-related trabecular meshwork thickening. A third depth preset of about 220 microns may accommodate older adults or patients with thickened or fibrotic trabecular meshwork. A fourth depth preset of about 250 microns may represent a maximum penetration limit designed to prevent damage to the outer wall of Schlemm's canal, the ciliary body, or suprachoroidal structures. The cooperation between the distal cutting end 1580 and the depth control system thereby provides a dual-constraint depth control system that enhances procedural safety, consistency, and reproducibility.

In some embodiments, the distal cutting end 1580 further includes one or more tissue-engaging features configured to stabilize the blade 1500 within the trabecular meshwork during bidirectional cutting or scraping. Such tissue-engaging features may include serrations, micro-teeth, barbs, ridges, grooves, or textured surfaces disposed on or adjacent to the first and second cutting edges 1584, 1586 that resist lateral slippage of the blade relative to the tissue being cut. In some embodiments, the tissue-engaging features are configured to provide positive engagement with the trabecular meshwork tissue in both the nasal and temporal cutting directions, thereby ensuring consistent cutting performance during bidirectional operation. In other embodiments, the distal cutting end 1580 includes one or more relief surfaces, channels, or flutes configured to reduce friction, facilitate tissue separation, permit fluid flow around the blade, or evacuate cut tissue debris during cutting.

In some embodiments, the distal cutting end 1580 is configured with a specific rake angle for each of the first and second cutting edges 1584, 1586. The rake angle, as used herein, refers to the angle between the cutting edge and a plane perpendicular to the direction of cutting travel. A positive rake angle (wherein the cutting edge leans forward in the direction of travel) may provide more aggressive cutting with reduced cutting force, whereas a negative rake angle (wherein the cutting edge leans backward) may provide more controlled, less aggressive cutting with increased cutting force. In some embodiments, the first and second cutting edges 1584, 1586 each have a rake angle in the range of about −10 degrees to about +30 degrees. In some embodiments, a rake angle of about 0 degrees to about +15 degrees is preferred for trabecular meshwork cutting, as this provides efficient tissue incision with minimal tissue tearing or displacement. The rake angle may be the same for both cutting edges (symmetric configuration) or different for each cutting edge (asymmetric configuration) to accommodate specific procedural requirements or anatomical variations.

Referring now to FIGS. 23A through 27, in some embodiments, the device 1200 includes a depth control system operably coupled to the blade 1500 and configured to limit penetration of the blade 1500 into target tissue. The depth control system comprises a depth-limiting mechanism having a plurality of selectable depth presets, each depth preset corresponding to a predetermined blade extension distance measured from the distal interface end 1420 of the delivery member 1400. The depth-limiting mechanism is operative to constrain advancement of the blade to a corresponding penetration depth. This constraint ensures controlled, reproducible cutting depth regardless of variations in manual force applied by the user, physiological hand tremors, involuntary micro-movements, or patient movement during the surgical procedure. The structure and operation of the depth control system is described in further detail below in connection with the actuation assembly.

In some embodiments, the depth control system cooperates with the delivery member distal interface to mechanically decouple physiologic surgeon hand tremor from blade penetration depth, such that hand tremor does not substantially affect a final blade penetration depth during incision or excision of trabecular meshwork. For example, the distal interface of the delivery member can be configured to contact ocular tissue surface, e.g., sclera or limbus, at a defined position (e.g., 0.5-1.0 mm from the limbus).

In some embodiments, the plurality of indexed mechanical stops corresponds to a plurality of discrete, selectable positions, each position corresponding to a tissue-layer-specific cutting depth. For example, a first indexed mechanical stop may be configured to limit blade penetration to the trabecular meshwork without extending into Schlemm's canal, a second indexed mechanical stop may permit blade penetration through the trabecular meshwork and into or through Schlemm's canal, and one or more additional indexed mechanical stops may correspond to other anatomical targets or procedural requirements.

In some embodiments, the indexed mechanical stops span a range of blade extension distances from about 150 μm to about 250 μm, measured from the distal interface end 1420 of the delivery member 1400. Within this range, the depth control system may provide two, three, four, or more discrete indexed mechanical stops. In some embodiments, the indexed mechanical stops may include: a first mechanical stop at about 150 μm suitable for patients with thin, compliant trabecular meshwork (e.g., pediatric or congenital glaucoma patients); a second mechanical stop at about 190 μm representing an anatomically derived central preset for standard adult cases; a third mechanical stop at about 220 μm for patients with age-related trabecular meshwork thickening; and a fourth mechanical stop at about 250 μm representing a maximum mechanical penetration limit to prevent damage to deeper ocular structures.

Third Implementation—Dual-Directional Cutting Geometry

As described above with respect to the distal cutting end 1580, the blade 1500 comprises a dual-directional cutting tip geometry configured to cut tissue in opposing circumferential directions along the anterior chamber angle without requiring reorientation or repositioning of the device 1200 mid-procedure. This dual-directional capability addresses a significant limitation of conventional goniotomy and trabeculotomy devices, in which a surgeon must typically withdraw, reposition, reorient, or rotate the device to incise tissue in opposing directions. The dual-directional cutting tip geometry of the distal cutting end 1580 comprises a first cutting edge 1584 and a second cutting edge 1586 disposed on opposing lateral sides of the blade body 1550, extending laterally such that both cutting edges simultaneously engage the trabecular meshwork tissue when the blade 1500 is displaced in either circumferential direction.

In use, the dual-directional cutting tip geometry of the distal cutting end 1580 permits a surgeon to position the device 1200 within the anterior chamber angle at a single corneal entry site, deploy the blade 1500, and perform incision or excision of the trabecular meshwork in opposing circumferential directions (i.e., nasally and temporally) while maintaining the device in the anterior chamber of the eye without withdrawing, rotating, or otherwise repositioning the device between cutting passes. This capability reduces overall procedure time, minimizes the number of instrument insertions and manipulations within the eye, decreases the risk of iatrogenic trauma to surrounding ocular structures, and promotes a more uniform and complete goniotomy or trabeculotomy.

In some embodiments, the ophthalmic surgical device further includes a visualization aid or alignment feature configured to assist the surgeon in orienting the device and the blade within the anterior chamber angle. Such visualization or alignment features may include markings, indicators, color coding, or geometric references on the delivery member or blade that are visible through a goniolens or other intraoperative visualization system, thereby facilitating accurate placement of the blade relative to the target trabecular meshwork tissue.

Third Implementation—Actuation Assembly

In some embodiments, the device 1200 includes an actuation assembly configured to control advancement and retraction of the blade 1500 relative to the delivery member 1400, and to enable selection among the indexed mechanical stops of the depth control system, as shown in FIG. 23A to FIG. 27. The actuation assembly is housed within the body 3060 and is operably coupled to the blade 1500 such that user manipulation of one or more control points results in controlled longitudinal displacement of the blade 1500 along the longitudinal axis Q.

In some embodiments, the depth control system further comprises a depth selector 1095 disposed on the device and configured for manual actuation. The depth selector 1095 is configured to advance and retract the blade 1500 within the lumen of the delivery member 1400 and to select among the plurality of indexed mechanical stops. The depth selector 1095 is coupled to the actuator 1090 and is longitudinally displaceable along the drive rod 1300. The actuator 1090 may be disposed on an exterior surface of the body 3060 at a location accessible to the user during operation, such as a proximal portion of the body 3060 for ease of access with a finger or thumb. The actuator 1090 may comprise a slider, trigger, wheel, lever, push-button, or other suitable control element that can be engaged with one or more fingers while the user maintains a stable grip on the body 3060.

In some embodiments, the depth selector 1095 is coupled to the actuator 1090 such that longitudinal displacement of the actuator 1090 produces a corresponding and equal longitudinal displacement of the depth selector 1095 along the drive rod 1300. The depth selector 1095 advances longitudinally at the same distance as the actuator 1090, on the order of millimeters or centimeters, and this longitudinal input displacement is converted into micrometer-scale blade displacement through the two-stage motion reduction mechanism described above.

In some embodiments, the actuator 1090 functions as the cam follower pin that is received within the helical cam track 1085 of the drive rod 1300. The cam follower pin 1090 extends from the depth selector 1095 and is inserted radially into the helical cam track 1085 such that, as the depth selector 1095 is advanced longitudinally, the cam follower pin 1090 is constrained to follow the helical path defined by the helical cam track 1085. Because the depth selector 1095 is constrained against rotation within the body 3060, the axial advancement of the cam follower pin 1090 along the helical cam track 1085 applies a tangential force to the helical cam track 1085, causing the drive rod 1300 to rotate. The resulting angular displacement of the drive rod 1300 is proportional to the longitudinal displacement of the depth selector 1095, with the proportionality constant determined by the helix angle and pitch of the helical cam track 1085.

In some embodiments, the annular proximal end structure 1080 of the depth selector 1095 serves as a bearing that slidably supports the depth selector 1095 on the drive rod 1300 while decoupling the longitudinal sliding motion of the depth selector 1095 from the rotational motion of the drive rod 1300. The annular proximal end structure 1080 permits the depth selector 1095 to translate freely along the drive rod 1300 without imparting or receiving rotational motion except through the cam follower pin 1090 and helical cam track 1085 interface. In some embodiments, the annular proximal end structure 1080 comprises a low-friction polymeric bushing, a self-lubricating bearing surface, or a clearance fit bore that minimizes frictional resistance during longitudinal translation of the depth selector 1095.

In some embodiments, the rotary-to-linear conversion element 1060 is disposed distally of the depth selector 1095 along the drive rod 1300 and is operably coupled between the drive rod 1300 and the drive stem 1050. In response to rotation of the drive rod 1300 caused by the advancement of the depth selector 1095 and the interaction of the cam follower pin 1090 with the helical cam track 1085, the rotary-to-linear conversion element 1060 converts the rotational motion of the drive rod 1300 into longitudinal displacement of the drive stem 1050 and the blade 1500. The displacement produced by the rotary-to-linear conversion element 1060 is on the order of micrometers per revolution of the drive rod 1300, thereby achieving the fine-resolution blade depth adjustment required for microsurgical applications.

In some embodiments, the rotary-to-linear conversion element 1060 may comprise a fine-pitch lead screw arrangement in which the drive rod 1300 includes a threaded portion that engages a complementary internal thread in the rotary-to-linear conversion element 1060, or in which the rotary-to-linear conversion element 1060 includes a threaded bore that threadedly engages the drive rod 1300. In other embodiments, the rotary-to-linear conversion element 1060 may comprise a cam-follower arrangement, a ball screw mechanism, a differential screw mechanism, or other suitable rotary-to-linear conversion means. The pitch of the threaded or cam engagement within the rotary-to-linear conversion element 1060 is selected in combination with the helix angle of the helical cam track 1085 to achieve the desired overall reduction ratio of the motion reduction mechanism.

In some embodiments, the depth selector 1095 is configured to provide tactile and/or audible feedback when a depth preset is selected, such as a click, detent engagement, or change in resistance, thereby confirming to the user that the selected depth preset has been properly engaged. For example, detent features such as spring-loaded ball detents, elastomeric snap features, or interference-fit protrusions may be incorporated into the depth selector 1095 and/or the body 3060 at positions corresponding to each indexed depth preset. Alternatively or additionally, the helical cam track 1085 may include localized detent recesses at angular positions corresponding to each indexed depth preset, such that the cam follower pin 1090 seats into a respective recess with a perceptible click when a preset is reached.

FIG. 23A to FIG. 23E illustrate the depth control system and blade 1500 in a first indexed position (Position 1). As shown in FIG. 23A, the device 1200 is depicted with the actuator 1090 in an initial proximal position. FIG. 23B illustrates the delivery member 1400 and the distal cutting end 1580 at Position 1, showing the blade 1500 in the stowed configuration or at a first depth preset in which the distal cutting end 1580 is at or near the distal interface end 1420. FIG. 23C illustrates the engagement between the cam follower pin 1090 and the helical cam track 1085 on the drive rod 1300 at Position 1, showing the cam follower pin 1090 seated at a first angular position within the helical cam track 1085. FIG. 23D illustrates the annular proximal end structure 1080 of the depth selector 1095 disposed over the drive rod 1300 and shows the relative positions of the rotary-to-linear conversion element 1060 and the drive stem 1050 at Position 1. FIG. 23E provides an additional view of the drive rod 1300 at Position 1.

FIG. 24A to FIG. 24E illustrate the depth control system and blade 1500 in a second indexed position (Position 2). The depth selector 1095 has been advanced longitudinally in the distal direction relative to Position 1, causing the cam follower pin 1090 to traverse a further portion of the helical cam track 1085 and imparting additional rotation to the drive rod 1300. Because of this further rotation of the drive rod 1300, the rotary-to-linear conversion element 1060 has displaced the drive stem 1050 and blade 1500 distally by an incremental micrometer-scale distance corresponding to a second depth preset. As shown in FIG. 24B, the distal cutting end 1580 now extends beyond the distal interface end 1420 by a distance corresponding to the second depth preset, for example about 150 μm. FIG. 24C illustrates the cam follower pin 1090 at a second angular position within the helical cam track 1085, advanced from the first angular position shown in FIG. 23C. FIG. 24D illustrates the corresponding distal advancement of the drive stem 1050 relative to the rotary-to-linear conversion element 1060.

FIG. 25A to FIG. 25E illustrate the depth control system and blade 1500 in a third indexed position (Position 3). The depth selector 1095 has been further advanced longitudinally in the distal direction relative to Position 2, causing further traversal of the cam follower pin 1090 along the helical cam track 1085 and additional rotation of the drive rod 1300. The rotary-to-linear conversion element 1060 has further displaced the drive stem 1050 and blade 1500 distally to a third depth preset. As shown in FIG. 25B, the distal cutting end 1580 extends beyond the distal interface end 1420 by a distance corresponding to the third depth preset, for example about 190 μm or about 220 μm. FIG. 25C illustrates the cam follower pin 1090 at a third angular position within the helical cam track 1085, and FIG. 25D illustrates the corresponding distal advancement of the drive stem 1050. FIG. 25E is a perspective view of the delivery member 1400 and blade 1500 at Position 3, showing the distal cutting end 1580 extending beyond the distal interface end 1420 of the delivery member 1400. As shown, the curved distal apex 1582 protrudes distally from the distal interface end 1420, and the first and second cutting edges 1584, 1586 are visible extending laterally on opposing sides of the blade body 1550. The curved, non-penetrating profile of the distal apex 1582 is clearly depicted, confirming that the foremost extremity of the blade presents a smoothly contoured surface rather than a sharp angular point.

FIG. 26A to FIG. 26E illustrate the depth control system and blade 1500 in a fourth indexed position (Position 4). The depth selector 1095 has been advanced to its most distal longitudinal position relative to the preceding positions, causing maximal traversal of the cam follower pin 1090 along the helical cam track 1085 and maximal rotation of the drive rod 1300. The rotary-to-linear conversion element 1060 has displaced the drive stem 1050 and blade 1500 to a fourth depth preset, representing the maximum mechanical penetration limit. As shown in FIG. 26B, the distal cutting end 1580 extends beyond the distal interface end 1420 by a distance corresponding to the fourth depth preset, for example about 250 μm. FIG. 26C illustrates the cam follower pin 1090 at a fourth angular position within the helical cam track 1085, and FIG. 26D illustrates the drive stem 1050 at its most distally advanced position relative to the rotary-to-linear conversion element 1060. FIG. 26E is a perspective view of the delivery member 1400 and blade 1500 at Position 4, showing the distal cutting end 1580 extending beyond the distal interface end 1420 at the maximum depth preset. The greater blade extension at Position 4 relative to Position 3 is visible, with the distal apex 1582 and first and second cutting edges 1584, 1586 extending further beyond the distal interface end 1420. The curved profile of the distal apex 1582 remains clearly visible, and the increased exposure of the laterally extending cutting edges 1584, 1586 at this maximum depth preset is apparent.

By mechanically constraining the blade 1500 to specific, reproducible depth settings through the two-stage motion reduction mechanism, the depth control system enhances procedural safety and consistency, reducing the risk of inadvertent damage to non-target tissues such as the ciliary body, iris root, scleral spur, or collector channel ostia. The mechanical motion reduction further provides inherent resistance to unintended blade displacement caused by physiological hand tremors or involuntary user movements, because any such tremor at the actuator 1090 is attenuated by the cumulative reduction ratio of the helical cam track 1085 and the rotary-to-linear conversion element 1060 before reaching the blade 1500.

In some embodiments, the actuation assembly further comprises one or more biasing elements configured to provide a restoring force that returns the blade 1500 to the stowed configuration upon release of the actuator 1090. The biasing elements may comprise one or more compression springs, extension springs, torsion springs, leaf springs, elastomeric elements, or other resilient members. Alternatively, or additionally, the actuation assembly may be configured such that the blade 1500 remains at the deployed depth preset until affirmatively retracted by the user through reverse actuation of the actuator 1090 and depth selector 1095.

In some embodiments, the actuation assembly includes one or more safety features configured to prevent unintended blade deployment or inadvertent depth changes during use. Such safety features may include a locking mechanism that secures the depth selector 1095 in a selected position, a safety interlock that prevents blade advancement until a deliberate unlocking action is performed, or a motion resistance feature that requires intentional force to actuate the actuator 1090. These safety features reduce the risk of accidental blade deployment during device handling, insertion, or positioning.

In some embodiments, the actuator 1090 and/or the depth selector 1095 may include surface features configured to enhance grip and control, even when the user is wearing surgical gloves or when moisture is present. Such surface features may include teeth, knurling, ribs, grooves, textured surfaces, or elastomeric overmolds. These grip-enhancing features promote confident and precise actuation of the actuation assembly under surgical conditions.

In some embodiments, the actuation assembly is configured to provide visual indication of the selected depth preset and/or the current blade deployment state. In some embodiments, the device 1200 may include depth markings, color-coded indicators, or a graduated scale visible on an exterior surface of the body 3060 or adjacent to the depth selector 1095. Such visual indicators enable the user to confirm the selected depth preset at a glance during the surgical procedure.

FIG. 27 illustrates an exploded perspective view of the device 1200 with the first and second housing portions 1062, 1064 of the body 3060 separated to reveal the internal arrangement of the actuation assembly. As shown, the drive rod 1300 extends within the body 3060, with the depth selector 1095 slidably disposed thereon. The annular proximal end structure 1080 of the depth selector 1095 is visible surrounding the drive rod 1300, and the cam follower pin 1090 extends from the depth selector 1095 into the helical cam track 1085 of the drive rod 1300. The rotary-to-linear conversion element 1060 is disposed distally of the depth selector 1095, and the drive stem 1050 extends from the rotary-to-linear conversion element 1060 toward the delivery member 1400 and blade 1500. This exploded view illustrates the spatial relationship and operative coupling among the components of the two-stage motion reduction mechanism.

Third Implementation—Device in Use

Figure 28:
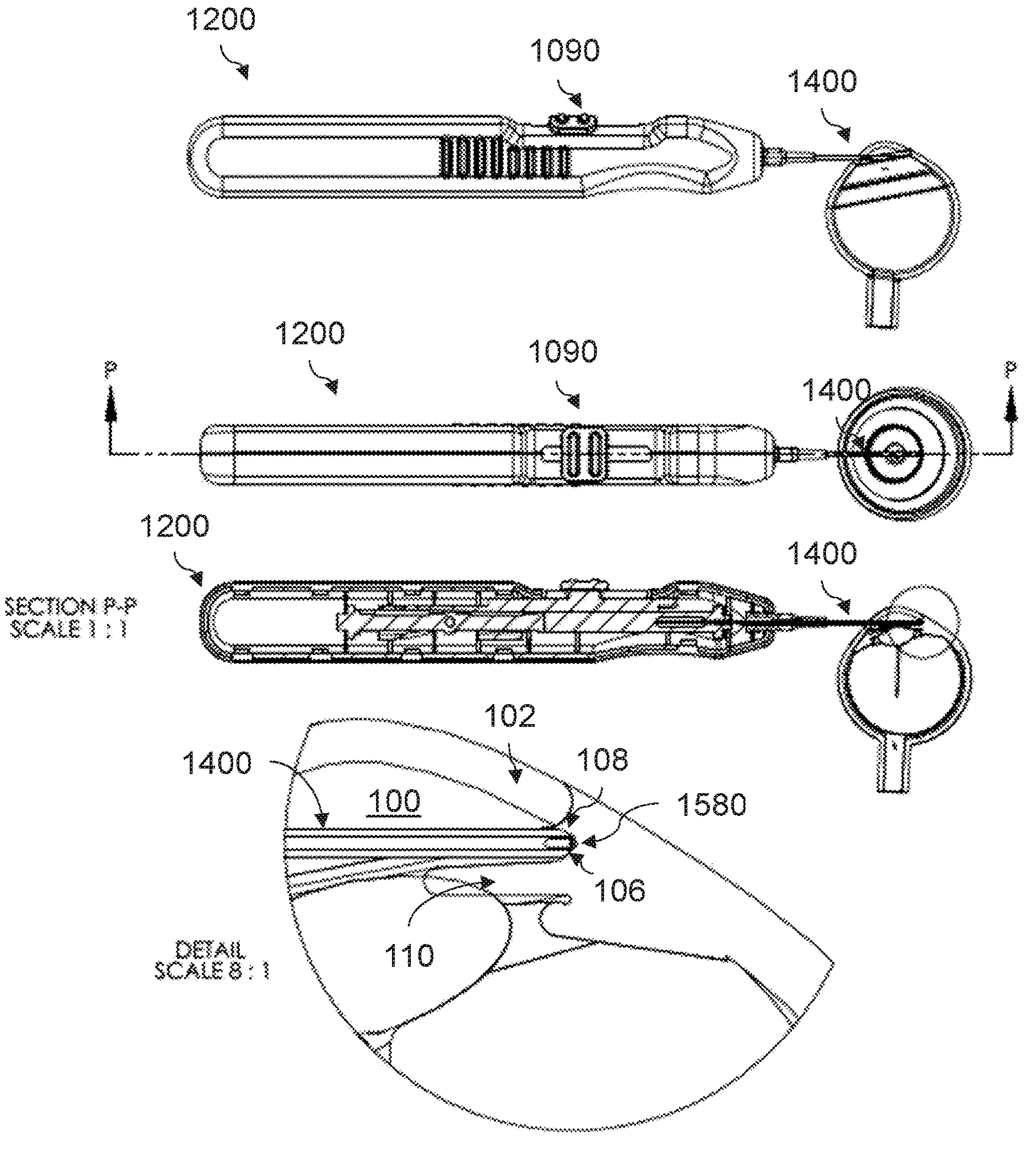
FIG. 28 are non-limiting views of the device of FIG. 21 in use on an eye to incise or excise trabecular meshwork tissue. The device is shown with the actuator in a first selectable position corresponding to a first selectable depth preset.
Figure 29:
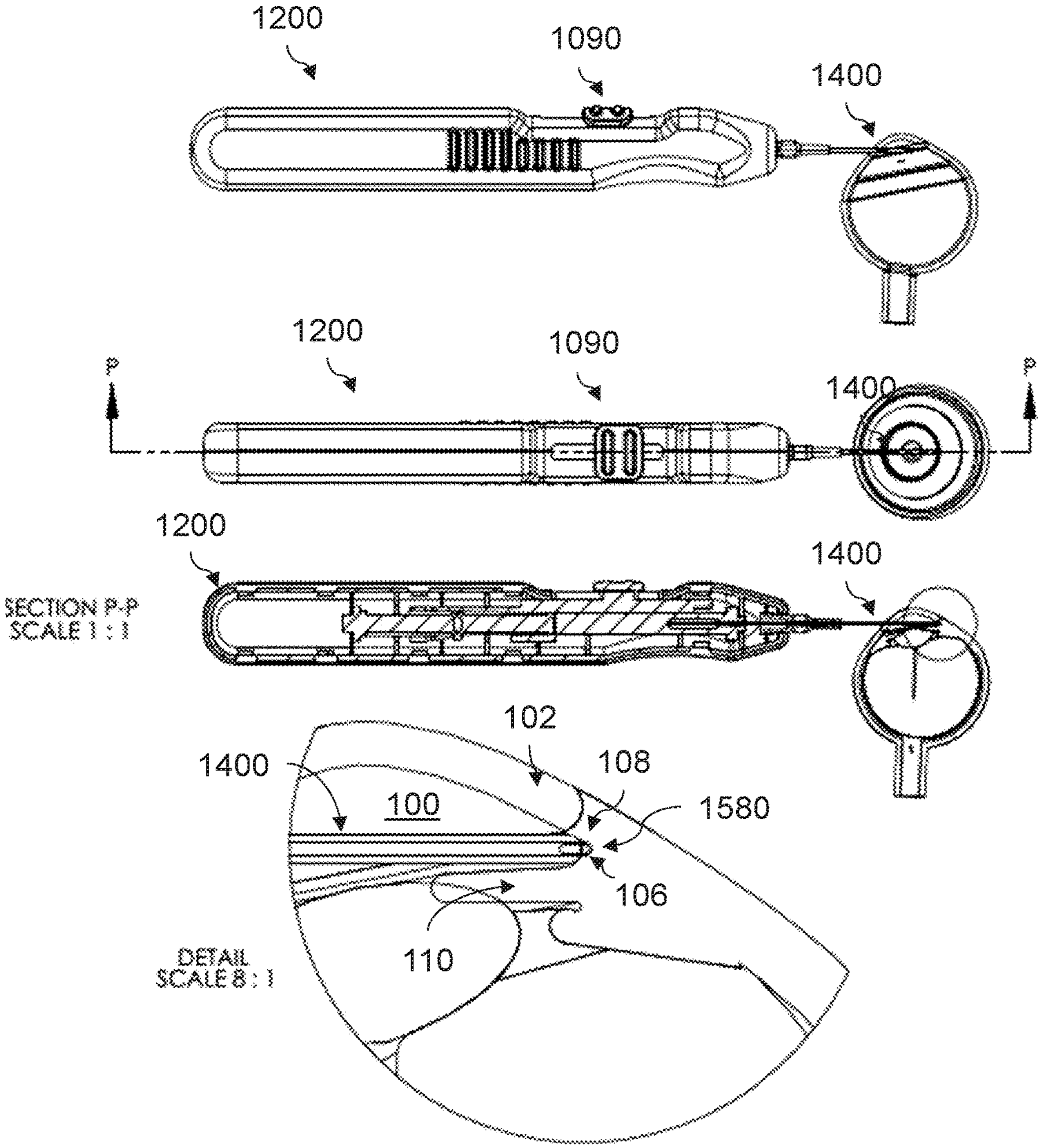
FIG. 29 are non-limiting views of FIG. 28 with the device shown with the actuator in a second selectable position corresponding to a second selectable depth preset.
Figure 30:
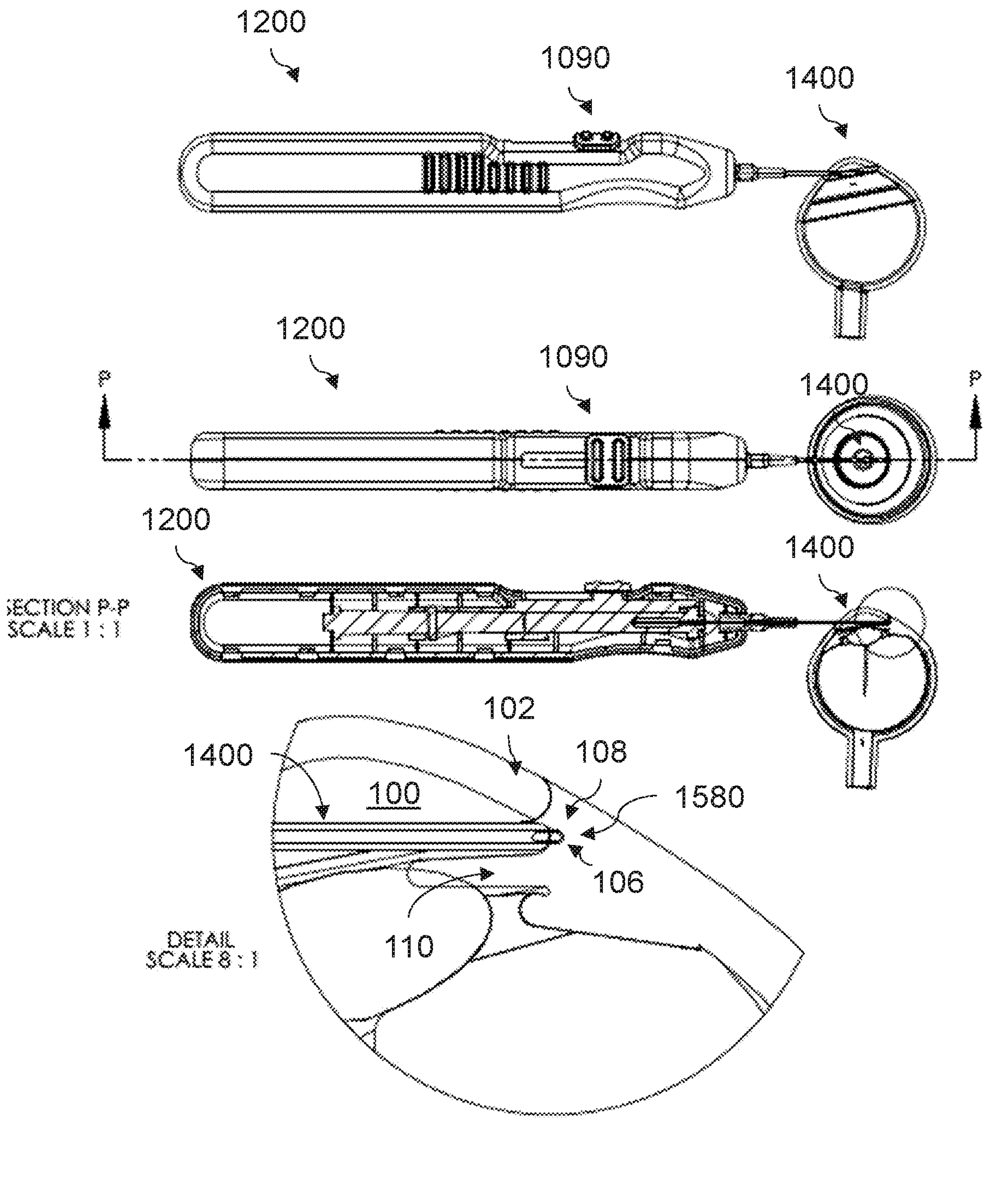
FIG. 30 are non-limiting views of FIG. 28 with the device shown with the actuator in a third selectable position corresponding to a third selectable depth preset.

Referring now to FIGS. 28, 29, and 30, non-limiting views of the device 1200 in use on an eye to incise or excise trabecular meshwork tissue are provided. These figures illustrate the operation of the depth control system and the selectable depth presets while the device 1200 is positioned within the anterior chamber of the eye. Advantageously, the surgeon may adjust the depth preset intraoperatively by manipulating the actuator 1090 while the device 1200 remains in the eye, without withdrawing or repositioning the device 1200.

As shown in FIG. 28, the device 1200 is depicted with the actuator 1090 in a first selectable position corresponding to a first selectable depth preset. In this configuration, the distal interface end 1420 of the delivery member 1400 is positioned against the sclera or other ocular tissue surface (e.g., limbus), establishing a stable tissue-referenced zero point. The blade 1500 extends beyond the distal interface end 1420 by a distance corresponding to the first depth preset, engaging the trabecular meshwork at a controlled penetration depth. The first selectable depth preset may correspond to a shallower blade extension suitable for patients with thinner trabecular meshwork tissue or for initial tissue engagement prior to deeper incision.

As shown in FIG. 29, the device 1200 is depicted with the actuator 1090 in a second selectable position corresponding to a second selectable depth preset. While the device 1200 remains in the anterior chamber of the eye, the surgeon has manipulated the actuator 1090 to advance the depth selector 1095 longitudinally, thereby causing the blade 1500 to extend further beyond the distal interface end 1420. The second depth preset provides an intermediate blade extension distance that may be suitable for standard adult trabecular meshwork anatomy. This intraoperative adjustment capability permits the surgeon to progressively increase blade penetration depth as needed during the procedure without removing or repositioning the device 1200.

As shown in FIG. 30, the device 1200 is depicted with the actuator 1090 in a third selectable position corresponding to a third selectable depth preset. In this configuration, the blade 1500 extends beyond the distal interface end 1420 by a greater distance than in the first or second selectable positions. The third depth preset may correspond to a blade extension suitable for patients with thicker or more fibrotic trabecular meshwork tissue, or for procedures requiring deeper incision or excision to adequately expose Schlemm's canal and the collector channel ostia. As with the transitions between the first and second selectable positions, the surgeon may advance the actuator 1090 to the third selectable position while the device 1200 remains in the anterior chamber of the eye, thereby enabling real-time depth adjustment in response to intraoperative tissue conditions.

The ability to select among the plurality of depth presets while the device 1200 remains positioned within the eye provides significant procedural advantages. The surgeon may begin the procedure at a shallower depth preset and progressively advance to deeper depth presets as the trabecular meshwork tissue is engaged and incised. This progressive approach permits the surgeon to optimize blade penetration depth for individual patient anatomy and tissue characteristics encountered during the procedure. Additionally, the intraoperative depth adjustment capability enables the surgeon to respond to real-time visualization of the surgical field, adjusting blade extension as needed to achieve the desired incision depth while minimizing the risk of damage to deeper structures such as the ciliary body or collector channels.

Optional Imaging System

In some embodiments, the device of the present invention is optionally further equipped with an imaging system including an imaging device configured to capture real-time images of a field of view proximate to the distal cutting end. The imaging system is configured to provide real-time images from a field of view corresponding to the incision path. Advantageously, the imaging system can be configured to generate real-time imaging of a field of view proximate to the blade, thereby enabling enhanced visualization during the surgical procedure.

In some embodiments, the imaging system provides the ability to determine in real-time the position of the blade while performing the incision on the tissue structure, such as on the trabecular meshwork.

In some embodiments, the imaging system includes a side-mounted camera on a guide or holder. In such embodiments, a micro-camera can be mounted on a thin guide or flexible arm that runs parallel to the piercing member 400 or delivery member 1400. Such configuration allows imaging without obstructing the blade 500, 1500 path. A non-limiting example may be an endoscopic camera with micro-LED illumination.

In some embodiments, the imaging system includes an integrated optical fiber system. In such embodiments, an optical fiber camera can run alongside the piercing member 400 or delivery member 1400, providing high-resolution images. Advantageously, optical fibers are thin and flexible, making them suitable for tight spaces. A non-limiting example may be optical coherence tomography (OCT) systems for ophthalmology.

In some embodiments the imaging system includes an external camera with augmented reality (AR) overlay. In such embodiments, a stationary or wearable external camera is configured to capture the procedure zone. Real-time AR overlays the blade path on a screen or AR glasses. This configuration advantageously avoids the need for miniaturization while still offering precision guidance. A non-limiting example may be Microsoft HoloLens™ which is used to enhance surgical procedures.

In some embodiments the imaging system includes a flexible arm with a mounted camera. In such embodiments, a flexible or articulated arm with a miniature camera is configured to follow the blade path. This configuration advantageously provides real-time tracking and imaging of the insertion point. A non-limiting example may be Da Vinci Surgical System (robotic-assisted surgery).

Figure 18:
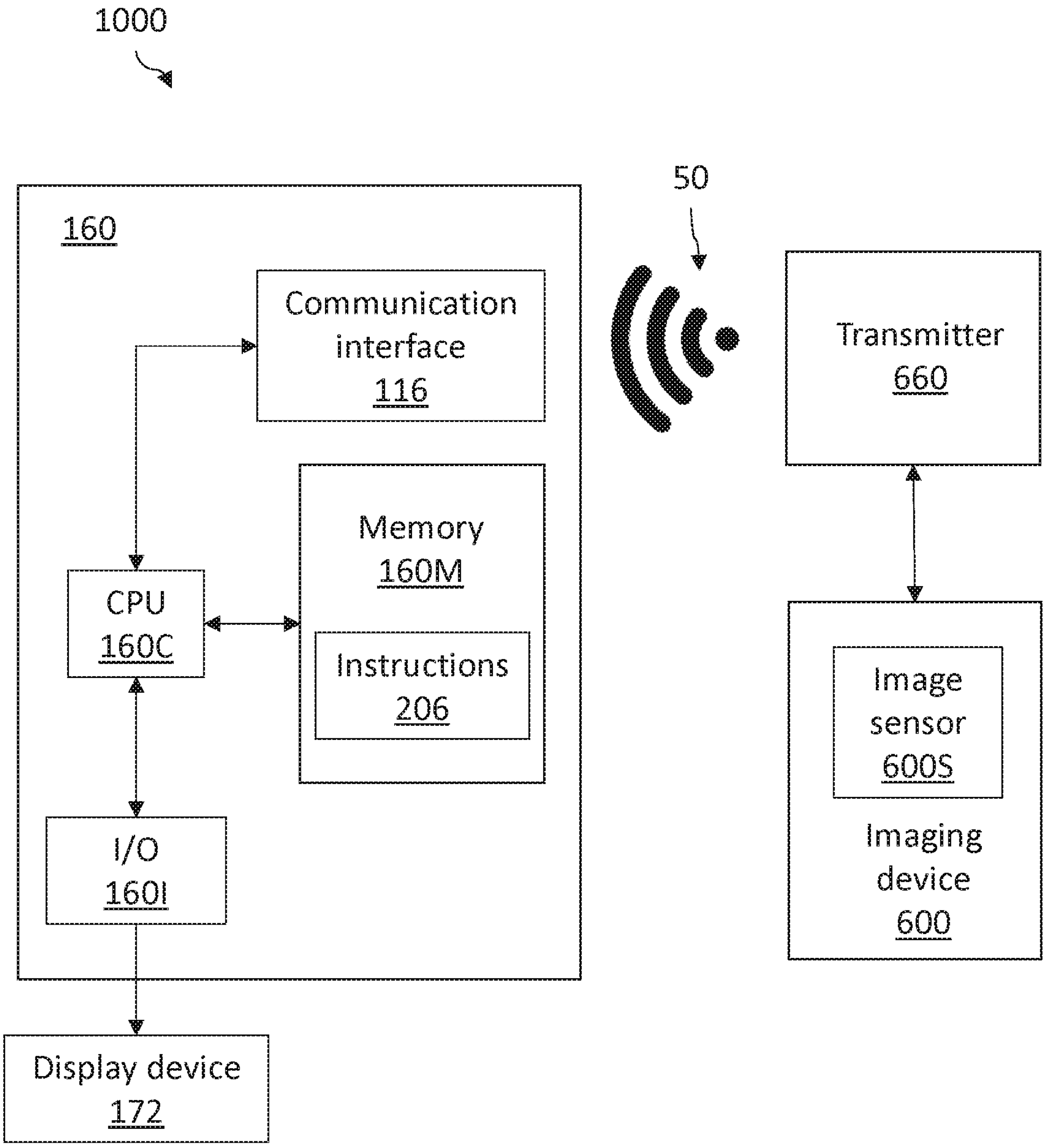
FIG. 18 is a non-limiting functional block diagram of various components of a imaging system for use with the device of FIG. 2A or FIG. 2B, in accordance with embodiments of the present disclosure.

With reference to the non-limiting practical implementation shown in FIG. 18, generally, the imaging system 1000 can include an imaging device 600 which is configured to acquire images of a surgical field to generate real-time imaging of a field of view proximate to the blade.

The imaging device 600 can be a digital imaging device. For example, a camera or video camera can be configured to acquire a series of still images or frames of the surgical field that together form a live, real-time view thereof. In that regard, the imaging device 600 can include an image sensor 600S, such as a charge coupled device (CCD) image sensor, complementary metal-oxide-semiconductor (CMOS) sensor, and/or other suitable image sensors. The imaging device 600 can be configured to receive light reflected from the surgical field. Preferably, the imaging device 600 can include an endoscopic camera with micro-LED illumination.

Advantageously, the imaging device 600 is capable of providing a minimum resolution of 720 HD, such as 1080p for clarity.

In some embodiments, the imaging device 600 can include a wide-angle camera, a fish-eye camera, or one camera that either moves side-to-side or records an image from a mirror that moves side-to-side.

Non-limiting examples of imaging devices that can be used for this purpose include cameras such as the Chip LED 0402 (ams-OSRAM AG, Austria), the CLM3C-WKW (CREE-LED, Penguin Solutions, USA), the KPG-0603 (Kingbright, France), the SMLP12WBDW (ROHM Semiconductor U.S.A. LLC), the NVSW219CT (Nichia Corporation, Japan), and the like.

In some embodiments the imaging system can include an alignment mechanism to ensure consistent pierce member-camera orientation. For example, a non-limiting example is described in US20240008895, which is herein incorporated by reference in its entirety.

With reference to FIG. 18, the imaging system 1000 can further include a computing device 160, such as a computer or a controller, configured to establish a communication link with the imaging device 600 directly or via wireless transmitter 660 which is configured to establish a data communication link with the imaging device 600. The computing device includes one or more processing units (CPU) 160C, a memory 160M in communication with the processing unit 1600, a communication interface 116 for communicating with the imaging device 600 and an input/output (I/O) interface 1601. The communication interface 116 may be configured to establish any suitable data communication link for communicating with the imaging device 600 directly or via wireless data communication link 50 through transmitter 660 which in turn is configured to establish a communication link with the imaging device 600, depending on application specifics. Such data communication link allows exchanging information between the imaging device 600 and the computing device 160, such as uploading/downloading data. Such data may relate for example to image or video data, battery status, etc.

The memory 160M is encoded with software instructions 206 for allowing the computing device 160 to perform the functions described herein. In some embodiments, the computing device 160 can receive and process the image or video data received from the imaging device 600. The memory 160M of the computing device 160 can store the pre-processed and/or post-processed image data. The computing device 160 can determine a surgeon's area of interest in the surgical field based on the images. The surgeon's area of interest can be determined in a variety of ways. In some embodiments, the computing device 160 can identify a portion of the device 200, such as a marker, a distal portion, or a tip, disposed in the surgical field. The computing device 160 can be configured to automatically identify target biological tissue, such as by executing image recognition software that detects various tissue structures in the procedure eye and compares them to known location, contours, and other anatomical features of the target biological tissue. In the example of trabecular meshwork surgery, the computing device 160 can determine the trabecular meshwork to be the area of interest and identify the trabecular meshwork in the images received from the imaging device 600. Yet other methods of determining the surgeon's area of interest are contemplated.

In some embodiments, the device described herein may be part of a surgical platform for trabecular meshwork incision or excision. The surgical platform may comprise: a tissue-cutting device with blade depth control and integrated imaging, and optionally adjustable geometry; and a computing device configured to record one or more parameters during each procedure. The recordable parameters may be selected from: (a) selected working angle from an articulation joint, when the device includes the adjustable geometry; (b) selected blade depth preset corresponding to a selected indexed mechanical stop; (c) duration of blade engagement with trabecular meshwork; (d) incision or excision arc length; (e) real-time imaging frames captured by the imaging system; (f) surgeon identifier; (g) patient identifier, optionally encrypted and HIPAA-compliant; and (h) post-operative IOP reduction and adverse events. This surgical platform enables systematic data collection for quality assurance, outcomes tracking, and procedural optimization.

The reader will understand that the computing device 160 is meant in its broadest sense and can include any electronic device with a processor including cellular telephones, smartphones, portable digital assistants, tablet devices, laptops, notebooks, and desktop computers.

In some embodiments, the imaging system can also include a display device 172 in communication with the computing device 160, for example through the I/O interface 1601. The display device 172 can be a projection device, such as a digital light processing (DLP) device, a liquid crystal display (LCD) device, a light emitting diode (LED) device, a liquid crystal on silicon (LCoS) device, other suitable devices, and/or combinations thereof. Such projection device can be in the operating room, the doctor's office, or remotely from a different location.

In some embodiments, the imaging device 600 may be connected to wireless transmitter 660, which can be located in a receiving cavity of proximal segment 65. The wireless transmitter 660 can be configured to transmit the images or videos being captured by the imaging device 600 to the computing device 160. The connection from the imaging device 600 to the wireless transmitter 660 may be over wire or other electrical connection 680. A non-limiting implementation of such configuration is shown in FIG. 5.

In some embodiments, the imaging device 600 may be powered via an independent power source, a light power source, or power source 640. In some embodiments, the power source 640 can be conveniently located in the receiving cavity of the body. For example, in the specific example of the first implementation, this can correspond to the receiving cavity of the proximal segment 65. The connection to power source 640 may be over wire or other electrical connection, which may be the same or different from wire or connection 680. The power source 640 may be any suitable power source, such as one or more battery. Alternatively, the power source 640 may be provided within the proximal segment 60 of the first implementation, or outside of the device body to provide power to the imaging device 600 without deviating from the scope of the disclosure. The device may include one or more batteries for powering the entire device or separately to each individual component.

In some embodiments, the imaging device 600 is coupled to, mounted to, or otherwise attached to probe (or stem) 650. In some embodiments, the imaging device 600 can be directly mounted to the probe 650.

In some embodiments, the probe 650 includes an elongate body that extends in an outwardly fashion, away from the device body. In some embodiments, the elongate body is flexible enough to move but sturdy enough to maintain alignment.

In some embodiments, the imaging device 600 is configured to generally face towards the space where the blade will be, or is being, utilized. In other embodiments, the orientation of the imaging device 600 may be customized/adjusted, and the corresponding calculations by the computing device 160 may consider the adjusted position of the imaging device 600. In some embodiments, the orientation of the imaging device 600 may be customized/adjusted with the use of a flexible probe 650.

In some embodiments, the device is further configured to move the probe 650 along its longitudinal axis, for example by engaging a control point to move the imaging device 600 closer or away from the tissue.

In some embodiments, the imaging device 600 may be sealed to the body of the probe 650 to prevent water ingress, and the housing of the imaging device 600 may be configured to satisfy tests of biocompatibility, cytotoxicity, sterilizability, and mechanical durability, among others.

Methods of Use—Incision Procedure

Figure 19:
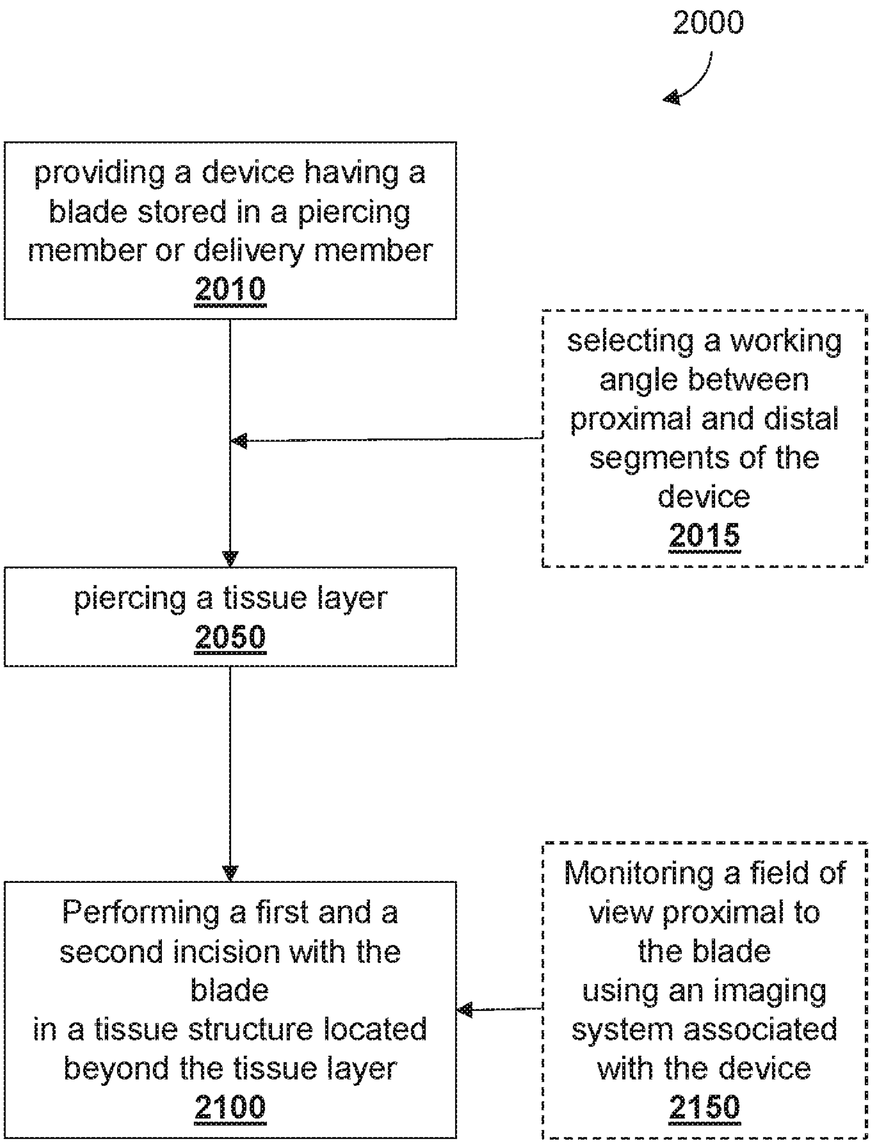
FIG. 19 is a non-limiting flowchart illustrating various method steps for using the device of FIG. 2A or FIG. 2B, in accordance with embodiments of the present disclosure.
Figure 20:
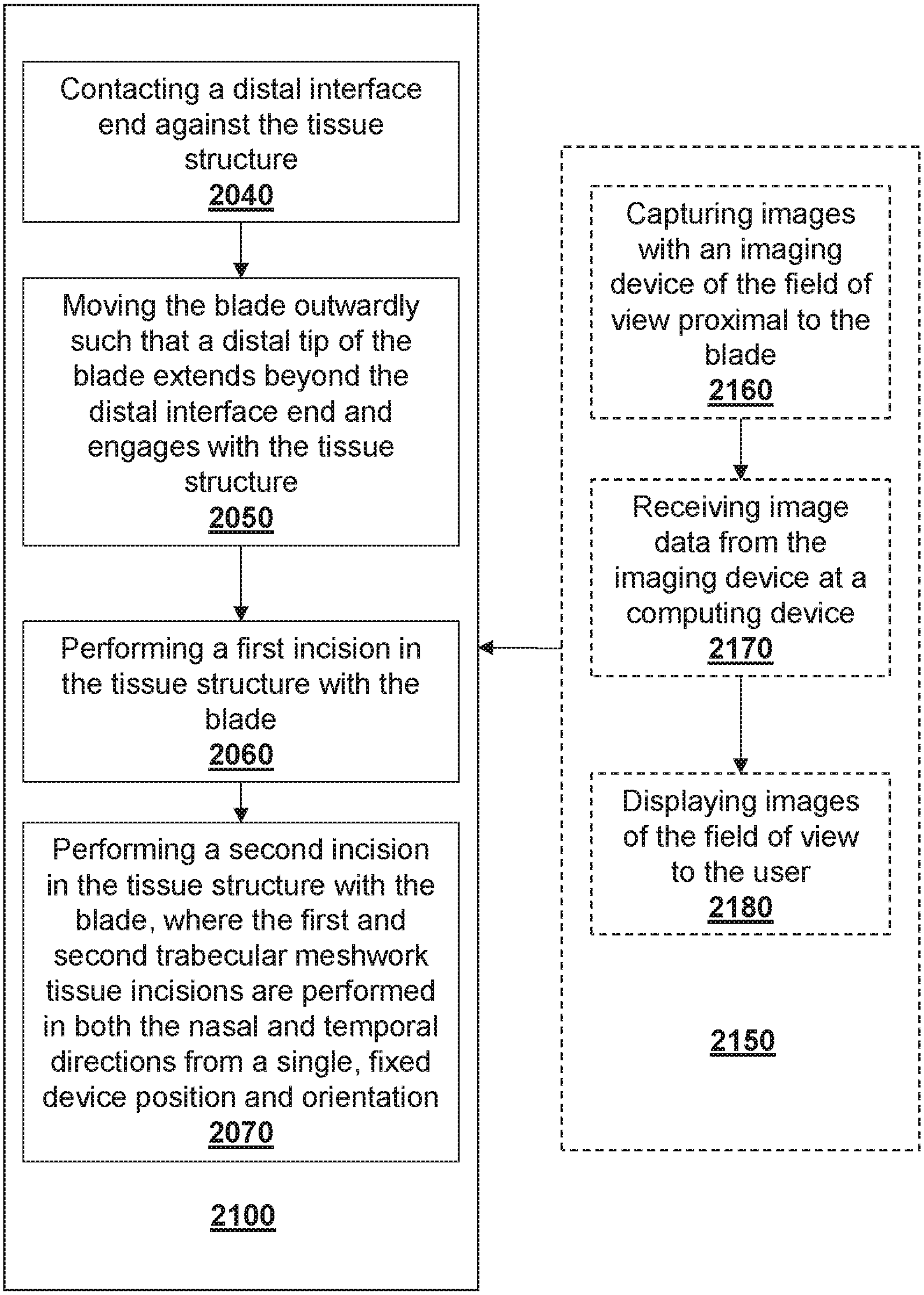
FIG. 20 is a non-limiting flowchart illustrating various additional steps for the method of FIG. 19, in accordance with embodiments of the present disclosure.

Referring now to FIGS. 19 and 20, flow diagrams illustrating methods of performing an incision in a tissue structure using the device described herein are provided. In some embodiments, the methods may be used to perform an incision in an eye tissue structure, such as in the trabecular meshwork.

As illustrated, method 1900 includes several enumerated steps, but embodiments of the method may include additional steps before, after, and in between the enumerated steps. In some embodiments, one or more of the enumerated steps may be combined, omitted, or performed in a different order, unless the context clearly indicates otherwise.

In a non-limiting implementation illustrated in FIG. 19, the method 1900 includes providing an ophthalmic surgical device having the herein described features, including a body, a delivery member having a body extending along a longitudinal axis and a distal interface end defining an aperture, the body defining a lumen extending therethrough in fluid communication with the aperture, a blade disposed at least partially within the lumen of the delivery member and movable relative to the delivery member along the longitudinal axis between a retracted position and an extended position, and a depth control system operably coupled to the blade, step 2010. Optionally, the method can include selecting a working angle between proximal segment and distal segment of the device if present, at step 2015.

The method 1900 can include piercing a tissue layer with the piercing member when operating the device of the first or second implementation, step 2050. For example, when performing an ab externo procedure on an eye, the tissue layer can be the eye sclera. Alternatively, when operating the device of the third implementation, the corneal incision/paracentesis is created with a separate (standard blade) instrument at step 2050.

The method 1900 then includes contacting a tissue structure located beyond the tissue layer with the blade and performing first and second incisions, step 2100. In some embodiments, the tissue structure can be the trabecular meshwork.

Optionally, the method 1900 can include monitoring a field of view proximate to the distal cutting end using an imaging device associated with the ophthalmic device, step 2150.

Specific steps that can be included in step 2100 will now be described with reference to FIG. 20.

The device is inserted into the eye until the distal interface end contacts and abuts against the eye tissue structure, step 2040. This step of positioning the tissue reference surface of the delivery member against the target tissue surface establishes a tissue-referenced zero point from which blade depth is measured, thereby reducing blade depth variability caused by physiological hand tremor during the procedure. At this stage, the user selects a depth preset by engaging the depth-limiting mechanism provided by the depth control system, and then operates a control point to cause displacement of the blade outwardly such that a distal tip of the blade extends beyond the distal interface end by a distance corresponding to the selected depth preset and engages with the eye tissue structure.

Once the blade has engaged with the eye tissue structure, the method includes performing an incision in the eye tissue structure by displacing the distal cutting end of the blade along a first incision path in a first circumferential direction on the surface of the eye tissue structure, at step 2060. In some embodiments, the first incision path can be along the nasal direction.

Upon completion of the first incision along the first incision path on the surface of the eye tissue structure, the method further includes performing a second incision along a second, distinct incision path in a second circumferential direction opposing the first circumferential direction, while maintaining the device in the anterior chamber of the eye, step 2070. In some embodiments, the second incision path can be along the temporal direction.

Advantageously, the first and second trabecular meshwork tissue incisions are performed in opposing circumferential directions (i.e., both nasally and temporally) from a single corneal entry site while maintaining the device in the anterior chamber of the eye. During depth preset selection, the user may receive tactile feedback indicative of engagement of the selected depth preset, and optionally audible feedback such as a click sound confirming that the selected depth preset has been properly engaged.

Specific steps included in optional step 2150 will now be described with reference to FIG. 20.

The imaging system can include an imaging device configured to capture images (e.g., still images or video) in a field of view proximate to the blade. Step 2160 can thus include capturing images with the imaging device of the field of view proximate to the blade. Image data from the imaging device are received at a computing device, step 2170.

As discussed elsewhere in this text, the computing device can process the image data for displaying on a graphical user interface, step 2180.

INDUSTRIAL APPLICABILITY

The ophthalmic surgical device and methods described herein are industrially applicable in the field of ophthalmic surgery, and in particular for the treatment of glaucoma and related conditions requiring reduction of intraocular pressure. The device is suitable for manufacture using conventional medical device manufacturing techniques, including precision machining, injection molding, and assembly of biocompatible materials. The device is particularly suited for use in clinical settings including hospitals, ambulatory surgical centers, and ophthalmic clinics, and may be employed by trained ophthalmologists, glaucoma specialists, and other qualified medical practitioners. The reproducible depth control afforded by the depth-limiting mechanism enables standardization of surgical outcomes across different operators and patient populations, thereby facilitating widespread clinical adoption.

Definitions

Unless otherwise defined, all technical and scientific terms used herein have the same meaning as commonly understood by a person of ordinary skill in the art to which the present invention pertains. As used herein, and unless stated otherwise or required otherwise by context, each of the following terms shall have the definition set forth below.

The following definitions are provided to assist in interpreting the specification and claims.

As used herein, the term "proximal" refers to the handle-end of a device held by a user, and the term "distal" refers to the opposite end.

As used herein, the user can be but without being limited to a medical practitioner, an eye surgeon, or an ophthalmologist.

As used herein, the term "tissue layer," as used herein, encompasses both a single tissue layer and a collection of layers, such as adjacent stacked layers (a multilayer) or distinct layers. However, the default interpretation typically refers to a single tissue layer. Additionally, when referring to a "tissue layer," it often pertains to a tissue wall characterized by a specific thickness and two sides (outer and inner, or proximal and distal). This application may be employed to address glaucoma by reducing intraocular pressure, achieved through facilitating fluid communication between the anterior chamber of the eye and the interface connecting the episclera and conjunctiva tissues, or subconjunctiva or subtenon area, for example.

Reference signs list

| Reference sign | Element |
|---|---|
| 10 | arrow (blade advancement direction) |
| 15 | arrow (return movement direction) |
| 25 | arrow (forward movement direction) |
| 50 | wireless data communication link |
| 60 | distal segment/body (third implementation: rotary-to-linear conversion element 1060) |
| 62 | first housing portion (distal segment) |
| 64 | second housing portion (distal segment) |
| 65 | proximal segment |
| 70 | piercing tip |
| 72 | first housing portion (proximal segment) |
| 74 | second housing portion (proximal segment) |
| 80 | locking mechanism |
| 85 | pivot point |
| 90 | first actuator |
| 92, 94 | extensions of first actuator |
| 95 | teeth |
| 100 | anterior chamber |
| 102 | cornea |
| 104 | sclera |
| 106 | trabecular meshwork |
| 108 | Schlemm's canal |
| 110 | iris/retention element |
| 112 | angle |
| 116 | communication interface |
| 125 | projection |
| 130 | second actuator |
| 135 | wheel gear |
| 140 | engaging elements (on projections) |
| 160 | computing device |
| 160C | processing unit (CPU) |
| 160I | I/O interface |
| 160M | memory |
| 172 | display device |
| 200 | device (first implementation) |
| 200' | device (second implementation) |
| 206 | software instructions |
| 300 | cannula |
| 310 | elongated body (cannula) |
| 320 | distal interface end (cannula) |
| 325 | distal aperture |
| 330 | distal segment (cannula) |
| 335 | bulbous structure |
| 400 | piercing member |
| 410 | elongated body (piercing member) |
| 450 | proximal portion (piercing member) |
| 500 | blade (first and second implementations) |
| 510 | shaft/body (blade) |

-continued

Reference signs list

| Reference sign | Element |
|---|---|
| 542 | slanted surfaces |
| 543 | edges |
| 545 | blade tip |
| 550 | distal cutting end (first and second implementations) |
| 580 | proximal end (blade) |
| 600 | imaging device |
| 600S | image sensor |
| 630 | internal cavity/receiving cavity |
| 640 | power source |
| 650 | probe/stem |
| 655 | retaining members |
| 660 | wireless transmitter |
| 680 | wire/electrical connection |
| 700 | release element |
| 710 | prongs |
| 720 | horizontal platform |
| 750 | actuating element |
| 800 | internal casing |
| 840 | engaging elements (on internal casing) |
| 850 | flexible lateral arms |
| 855 | distal end (flexible arms) |
| 860, 860A, 860B | apertures/superior surface |
| 900 | hub |
| 910 | engaging tab |
| 920 | interfering structure |
| 930 | proximal ring |
| 940 | distal end (hub) |
| 950 | distal orifice |
| 1000 | imaging system |
| 1050 | drive stem |
| 1060 | rotary-to-linear conversion element/body (third implementation) |
| 1062 | first housing portion (third implementation) |
| 1064 | second housing portion (third implementation) |
| 1080 | annular proximal end structure |
| 1085 | helical cam track |
| 1090 | actuator/cam follower pin (third implementation) |
| 1095 | depth selector |
| 1200 | device (third implementation) |
| 1300 | drive rod |
| 1400 | delivery member (third implementation) |
| 1410 | elongated body (delivery member) |
| 1420 | distal interface end (delivery member) |
| 1500 | blade (third implementation) |
| 1550 | blade body (third implementation) |
| 1580 | distal cutting end (third implementation) |
| 1582 | distal apex |
| 1584 | first cutting edge |
| 1586 | second cutting edge |
| 1900 | method |
| 2010 | elongated body (delivery member)/method step (providing device) |
| 2015 | method step (selecting working angle) |
| 2050 | method step (piercing tissue layer) |
| 2100 | method step (contacting tissue structure) |
| 2150 | method step (monitoring field of view) |
| 3060 | body (third implementation) |

Other examples of implementations will become apparent to the reader in view of the teachings of the present description and as such, will not be further described here.

All references cited throughout the specification are hereby incorporated by reference in their entirety for all purposes.

Note that titles or subtitles may be used throughout the present disclosure for convenience of a reader, but in no way should these limit the scope of the invention. Moreover, certain theories may be proposed and disclosed herein; however, in no way they, whether they are right or wrong, should limit the scope of the invention so long as the invention is practiced according to the present disclosure without regard for any theory or scheme of action.

As used herein, the wording "independently selected" in reference to a group of specified items refers to the fact that when more than one item is selected from the group of items, the decision of selecting a specific item is not influenced by the decision of selecting any of the previous or following item(s).

Reference throughout the specification to "some embodiments", and so forth, means that a particular element (e.g., feature, structure, and/or characteristic) described in connection with the invention is included in at least one embodiment described herein, and may or may not be present in other embodiments. In addition, it is to be understood that the inventive features described may be combined in any suitable manner in the various embodiments.

It will be understood by those of skill in the art that throughout the present specification, the term "a" used before a term encompasses embodiments containing one or more to what the term refers. It will also be understood by those of skill in the art that throughout the present specification, the term "comprising", which is synonymous with "including," "containing," or "characterized by," is inclusive or open-ended and does not exclude additional, un-recited elements or method steps.

Unless otherwise defined, all technical and scientific terms used herein have the same meaning as commonly understood by one of ordinary skill in the art to which this invention pertains. In the case of conflict, the present document, including definitions will control.

As used in the present disclosure, when the terms "around", "about" or "approximately" are before a quantitative value, the present disclosure also includes the specific quantitative value itself, unless specifically stated otherwise. As used herein, the terms "around", "about" or "approximately" refer to a ±10% variation from the nominal value unless otherwise indicated or inferred.

Unless otherwise noted, the expression "at least" or "at least one of" as used herein includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Unless otherwise noted, the order of steps or order for performing certain actions is immaterial so long as the present invention remain operable. Moreover, two or more steps or actions may be conducted simultaneously.

Unless otherwise noted, the use of any and all examples, or exemplary language herein, for example, "such as" or "including," is intended merely to illustrate better the present invention and does not pose a limitation on the scope of the invention. No language in the specification should be construed as indicating any non-claimed element as essential to the practice of the present invention.

Although various embodiments of the disclosure have been described and illustrated, it will be apparent to those skilled in the art considering the present description that numerous modifications and variations can be made without departing from the invention. The scope of the invention is defined more particularly in the appended claims, and all equivalents thereof are intended to be embraced therein.

The invention claimed is:

1. An ophthalmic surgical device configured to perform trabecular meshwork incision or excision in an eye, comprising a blade having adjustable penetration depth and a distal cutting end, and a tissue reference surface configured to contact the eye's sclera or limbus, and define a reference for the adjustable penetration depth, a distal interface end defining the tissue reference surface, the body defining a lumen extending therethrough, wherein the blade is disposed at least partially within the lumen" after, wherein the blade distal cutting end has a bidirectional cutting geometry configured to enable incision or excision of trabecular meshwork tissue in opposing circumferential directions while maintaining the device in the eye wherein the distal cutting end comprises a curved, rounded, or arcuate distal apex, wherein the distal apex being a smoothly contoured non-penetrating surface, and laterally extending cutting edges disposed on opposing lateral sides of the blade body, the cutting edges defining an aperture there between, extending from and diverging laterally from the distal apex.

2. The device of claim 1, wherein the blade is movable from a retracted position, in which the blade is contained within the lumen, to an extended position, in which the distal cutting end extends beyond the distal interface end.

3. The device of claim 1, further comprising a depth control system operably coupled to the blade and configured to limit penetration of the blade into the trabecular meshwork, the depth control system comprising a depth-limiting mechanism having a plurality of selectable depth presets, each depth preset corresponding to a predetermined maximum displacement of the distal cutting end relative to the tissue reference surface.

4. The device of claim 3, wherein the plurality of selectable depth presets corresponds to a plurality of discrete, selectable positions of a manual actuator operatively linked to the depth-limiting mechanism, each position corresponding to a predetermined extension distance of the distal cutting end measured from the distal interface end.

5. The device of claim 4, wherein the plurality of discrete, selectable positions corresponds to selectable depth presets in the range of from about 150 μm to about 250 μm.

6. The device of claim 4, wherein the plurality of discrete, selectable positions corresponds to selectable depth presets of about 150 μm, about 190 μm, about 220 μm, and about 250 μm.

7. The device of claim 3, wherein the depth control system comprises a mechanical indexing structure configured to provide tactile feedback when a depth preset is selected.

8. The device of claim 7, wherein the mechanical indexing structure is further configured to provide audible feedback when a depth preset is selected.

9. The device of claim 1, wherein a distal interface end and a depth control system cooperate to provide a dual-constraint depth control during incising.

10. The device of claim 1, wherein the tissue reference surface comprises a foot, flange, ledge, shoulder, or abutment surface configured to rest against or engage the eye's limbus or sclera.

11. The device of claim 1, wherein the laterally extending cutting edges are substantially mirror-symmetric relative to a central plane containing the longitudinal axis, such that cutting performance is substantially equivalent in both lateral directions.

12. The device of claim 1, wherein the distal cutting end has a width of about 300 microns.

13. The device of claim 1, wherein the tissue reference surface is configured to contact the eye's sclera or limbus, to reduce blade depth variability caused by physiological hand tremor during use.

14. The device of claim 1, further comprising an imaging system including an imaging device configured to capture real-time images of a field of view proximate to the distal cutting end.

15. The device of claim 14, wherein the imaging system is aligned with or proximate to the blade and configured to visualize trabecular meshwork during incision or excision.

16. The device of claim 1, wherein the blade further comprises a ramp or wedge geometry configured to elevate trabecular meshwork tissue prior to incision or excision.

* * * * *